(12) United States Patent
Birault et al.

(10) Patent No.: US 9,150,508 B2
(45) Date of Patent: Oct. 6, 2015

(54) SULFONAMIDE COMPOUNDS AND THEIR USE IN THE MODULATION RETINOID-RELATED ORPHAN RECEPTOR

(71) Applicant: Glaxo Group Limited, Brentford, Middlesex (GB)

(72) Inventors: Veronique Birault, Stevenage (GB); Amanda Jennifer Campbell, Stevenage (GB); Stephen Harrison, Stevenage (GB); Joelle Le, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/347,018

(22) PCT Filed: Sep. 25, 2012

(86) PCT No.: PCT/EP2012/068845
§ 371 (c)(1),
(2) Date: Mar. 25, 2014

(87) PCT Pub. No.: WO2013/045431
PCT Pub. Date: Apr. 4, 2013

(65) Prior Publication Data
US 2014/0243362 A1 Aug. 28, 2014

(30) Foreign Application Priority Data
Sep. 27, 2011 (GB) .................................. 1116641.0

(51) Int. Cl.
*C07D 261/08* (2006.01)
*C07D 261/10* (2006.01)
(Continued)

(52) U.S. Cl.
CPC ............. *C07C 311/29* (2013.01); *C07C 311/21* (2013.01); *C07C 311/44* (2013.01);
(Continued)

(58) Field of Classification Search
CPC ... C07D 261/08; C07D 261/10; C07D 261/14
See application file for complete search history.

(56) References Cited

FOREIGN PATENT DOCUMENTS

EP    1 657 238 A1    5/2006
WO   WO 2006/038594 A1   4/2006

OTHER PUBLICATIONS

Larsen, et al. Bioorganic & Medicinal Chemistry Letters, 16(24): 6173-6177 (2006).

(Continued)

*Primary Examiner* — Bruck Kifle
(74) *Attorney, Agent, or Firm* — Dara L. Dinner; Theodore R. Furman

(57) ABSTRACT

The present invention is directed to novel retinoid-related orphan receptor gamma (RORγ) modulators of formula (I), processes for their preparation, pharmaceutical compositions containing these modulators, and their use in the treatment of inflammatory, metabolic and autoimmune diseases mediated by RORγ

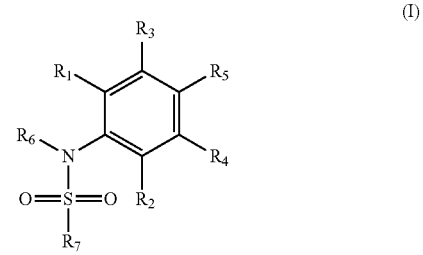

(I)

wherein
$R_1$ and $R_2$ are independently selected from the group consisting of H, $CF_3$, halo, $C_{1-3}$alkyl and $C_{1-3}$-alkoxy;
$R_3$ and $R_4$ are independently selected from the group consisting of H, $CF_3$, halo, $CH_3$ and $OCH_3$;
$R_5$ is selected from the group consisting of H, $CF_3$, halo, OH, $CH_2OH$, $C_{1-4}$alkyl, $CH_2$-cyclopropyl and $C_{1-4}$alkoxy, wherein $C_{1-4}$alkyl and $C_{1-4}$alkoxy, may be optionally substituted with one or two OH substituents;
$R_6$ is selected from the group consisting of $C_{3-5}$alkyl and $—CH_2—C_{3-4}$cycloalkyl;
$R_7$ is selected from the group consisting of

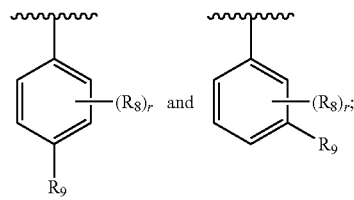

$R_8$ is selected from the group consisting of $C_{1-3}$alkyl, $C_{1-3}$alkoxy, $CH_2CN$, $CH_2OH$, OH, CN and halo;
$R_9$ is the group $—(CHR_{10})_s—(X)_t—(CHR_{10})_u—R_{11}$;
each $R_{10}$ is independently selected from the group consisting of H, OH or $CH_2OH$;
$R_{11}$ is an isoxazole, $—C(O)OH$, or a 5- or 6-membered heteroaryl group, wherein the isoxazole or the 5- or 6-membered heteroaryl group may be optionally substituted with one or two halo, $NH_2$ or $CH_3$ substituents;
X is $CH_2$, NH, O;
r is 0, 1 or 2;
s is 0, 1 or 2;
t is 0 or 1;\
u is 0, 1 or 2;
with the proviso that no more than two $R_{10}$ groups represent OH or $CH_2OH$.

18 Claims, No Drawings

(51) Int. Cl.
- *C07D 261/14* (2006.01)
- *C07C 311/29* (2006.01)
- *C07C 311/21* (2006.01)
- *C07C 311/44* (2006.01)
- *C07D 213/30* (2006.01)
- *C07D 213/38* (2006.01)
- *C07D 213/61* (2006.01)
- *C07D 213/65* (2006.01)
- *C07D 213/68* (2006.01)
- *C07D 213/75* (2006.01)
- *C07D 233/22* (2006.01)
- *C07D 239/28* (2006.01)
- *C07D 249/08* (2006.01)
- *C07D 257/04* (2006.01)
- *C07D 213/42* (2006.01)
- *C07D 231/12* (2006.01)
- *C07D 233/64* (2006.01)
- *C07D 239/26* (2006.01)
- *C07D 239/34* (2006.01)

(52) U.S. Cl.
CPC ............ *C07D213/30* (2013.01); *C07D 213/38* (2013.01); *C07D 213/42* (2013.01); *C07D 213/61* (2013.01); *C07D 213/65* (2013.01); *C07D 213/68* (2013.01); *C07D 213/75* (2013.01); *C07D 231/12* (2013.01); *C07D 233/22* (2013.01); *C07D 233/64* (2013.01); *C07D 239/26* (2013.01); *C07D 239/28* (2013.01); *C07D 239/34* (2013.01); *C07D 249/08* (2013.01); *C07D 257/04* (2013.01); *C07D 261/08* (2013.01)

(56) References Cited

OTHER PUBLICATIONS

Kumar, et al. Probe Reports from the NIH Molecular Libraries Program. Retrieved from the Internet: URL:http://www.ncbi.nlm.nih.gov/books/NBK56239/ (Mar. 11, 2011).

Di Nunno, et al. Journal of Medicinal Chemistry, 47(20): 4881-4890 (2004).

SULFONAMIDE COMPOUNDS AND THEIR USE IN THE MODULATION RETINOID-RELATED ORPHAN RECEPTOR

This application is a 371 of International Application No. PCT/EP2012/068845, filed 25 Sep. 2012, which claims the priority of GB 1116641.0, filed 27 Sep. 2011, which are incorporated herein in their entireties.

FIELD OF THE INVENTION

The present invention is directed to novel retinoid-related orphan receptor gamma (RORγ) modulators, processes for their preparation, pharmaceutical compositions containing these modulators, and their use in the treatment of inflammatory, metabolic and autoimmune diseases mediated by RORγ.

BACKGROUND OF THE INVENTION

Retinoid-related orphan receptors (RORs) are transcription factors that form a subgroup of the nuclear receptor superfamily (*Adv. Dev. Biol.* 2006, 16, 313-355). This subgroup consists of three members: ROR alpha (RORα), ROR beta (RORβ) and ROR gamma (RORγ). RORα and RORβ have approximately 55% homology in the ligand binding domains to RORγ. RORs contain four principal domains shared by the majority of nuclear receptors: an N-terminal A/B domain, a DNA-binding domain, a hinge domain and a ligand binding domain.

The RORα, RORβ and RORγ genes have been mapped to human chromosomes 15q22.2, 9q21.13 and 1q21.3, respectively. Each ROR gene generates several isoforms, which differ only in their N-terminal A/B domain. To date, five splice variants have been recorded for RORγ and two isoforms of this member of the ROR family have been identified: RORγ1 and RORγ2 (also known as RORγt). RORγ is a term used to describe RORγ1 and/or RORγt.

While RORγ1 is expressed in a variety of tissues including thymus, muscle, kidney and liver, RORγt is exclusively expressed in the cells of the immune system and has a critical role in thymopoiesis, development of several secondary lymphoid tissues and Th17 lineage specification.

RORγt has been identified as a key regulator of Th17 cell differentiation (A. Jetten, *Nuclear Receptor Signalling* 2009, 7, 1-32). Th17 cells are a recently discovered subset of T helper cells which preferentially produce cytokines IL-17A, IL-17F, IL-21 and IL-22. RORγt also induces transcription of the gene encoding IL-17A and IL-17F in naïve CD4$^+$ T helper cells, iNKT and NKT (*Mucosal Immunol.* 2009, 2(5), 383-392; *J. Immunol.* 2008, 180, 5167-5171), γδT cells (*Am. J. Respir. Crit. Care Med.* 2010, 182, 464-476), CD8$^+$ T cells (*J. Leukocyte Biol.* 2007, 82, 354-360) and finally CD4$^-$CD8$^-$ TCRαβ$^+$ T cells (*J. Immunol.* 2008, 181, 8761-8766). Additional immune cells such as eosinophils, neutrophils and macrophages can also be a source of IL-17A in allergic inflammation related to asthma (*J. Allergy Clin. Immunol.* 2001, 108, 430-438; *J. Immunol.* 2008, 181, 6117-6124; *Immunity* 2004, 21, 467-476).

Th17 cells and their products have been shown to be associated with the pathology of a number of human inflammatory and autoimmune disorders. IL-17A and IL-17F are implicated in numerous immune and inflammatory responses primarily as pro-inflammatory regulators inducing the expression of cytokines, chemokines, adhesion molecules, mucin genes and growth factors. There is emerging evidence that an increase in IL-17A level is closely associated with a range of chronic inflammatory diseases such as rheumatoid arthritis (*Curr. Opin. Investig. Drugs* 2009, 10, 452-462), multiple sclerosis (*Allergol. Int* 2008, 57(2), 115-120), inflammatory bowel diseases (*J. Inflamm. Res.* 2010, 3, 33-44), uveitis, psoriasis (*Sci. Transl. Med.* 2010, 2(52)) and lung diseases (*Prog. Respir. Res. Basel* 2010, 39, 141-149; *Resp. Research* 2010, 11 (78), 1-11).

There is considerable evidence suggesting that Th17 cells/IL-17 play a key role in the pathogenesis of asthma. In asthmatic patients, both RORγt and IL-17A expression levels have been shown to be increased in sputum (*Chin. Med. J.* 2005, 118, 953-956; *Resp. Res.* 2006, 7(135), 1-9), lung (*J. Allergy Clin. Immunol.* 2003, 111(6), 1293-1298), bronchoalveolar lavage (BAL) fluids and peripheral blood (*Immunol. Invest.* 2009, 38, 652-664; *Int. Arch. Allergy Immunol.* 2005, 137 (suppl. 1), 51-54) and levels directly correlate with disease severity (*Int. Arch. Allergy Immunol.* 2010, 151, 297-307). In addition to IL-17A, a recent study has shown that a further cytokine of the IL-17 family, IL-17F, may have a crucial role in allergic airway inflammation and hence have key implications in airway diseases, such as asthma. The overexpression of the IL-17F gene in mice airways was associated with airway neutrophilia, cytokine induction, an increase in airway hyperreactivity and mucus hypersecretion (*Inflamm. Allergy Drug Targets* 2009, 8, 383-389). Evidence of role of Th17 cells in allergens has been discussed in *Int. Immunopharmacol.* 2010, 10, 226-229.

The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (*J. Exp. Med.* 2008, 205, 1517-1522; *Cell. Mol. Immunol.* 2010, 7, 182-189). There is also evidence that Th17 cells are activated during the disease process and are responsible for recruiting other inflammatory cells types, especially neutrophils, to mediate pathology in the target tissues (*Anna. Rev. Immunol.* 2009, 27, 485-517). RORγt plays a critical role in the pathogenic responses of Th17 cells (*Cell* 2006, 126, 1121-1133). RORγt deficient mice show very few Th17 cells. Further support for the role of RORγt in the pathogensis of autoimmune or inflammatory diseases can be found in the following references: *Immunity* 2007, 26, 643-654; *Nat. Rev. Immunol* 2006, 6, 205-217; *J. Immunol.* 2009, 183, 7169-7177; *Brain Pathol.* 2004, 14, 164-174; *Brain* 2007, 130, 1089-1104; *Nat. Rev. Immunol.* 2008, 8, 183-192.

In light of the role RORγ plays in the pathogenesis of diseases, it is desirable to prepare compounds that modulate RORγ activity and hence have utility in the treatment of inflammatory, metabolic and autoimmune diseases mediated by RORγ, such as the respiratory diseases asthma, chronic obstructive pulmonary disease (COPD) and bronchitis, allergic diseases including allergic rhinitis and atopic dermatitis, cystic fibrosis and lung allograph rejection.

SUMMARY OF THE INVENTION

According to the invention, there is provided novel retinoid-related orphan receptor gamma (RORγ) modulators, processes for their preparation, pharmaceutical compositions comprising these modulators, and their use in the treatment of inflammatory, metabolic and autoimmune diseases mediated by RORγ. More specifically, the present invention is directed to compounds of formula (I), and to pharmaceutically acceptable salts thereof:

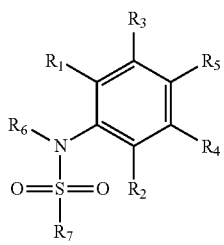

wherein
$R_1$ and $R_2$ are independently selected from the group consisting of H, $CF_3$, halo, $C_{1-3}$alkyl and $C_{1-3}$-alkoxy;
$R_3$ and $R_4$ are independently selected from the group consisting of H, $CF_3$, halo, $CH_3$ and $OCH_3$;
$R_5$ is selected from the group consisting of H, $CF_3$, halo, OH, $CH_2OH$, $C_{1-4}$alkyl, $CH_2$-cyclopropyl and $C_{1-4}$alkoxy, wherein $C_{1-4}$alkyl and $C_{1-4}$alkoxy, may be optionally substituted with one or two OH substituents;
$R_6$ is selected from the group consisting of $C_{3-5}$alkyl and —$CH_2$—$C_{3-4}$cycloalkyl;
$R_7$ is selected from the group consisting of

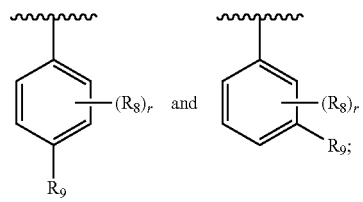

$R_8$ is selected from the group consisting of $C_{1-3}$alkyl, $C_{1-3}$alkoxy, $CH_2CN$, $CH_2OH$, OH, CN and halo;
$R_9$ is the group —$(CHR_{10})_s$—$(X)_t$—$(CHR_{10})_u$—$R_{11}$;
each $R_{10}$ is independently selected from the group consisting of H, OH or $CH_2OH$;
$R_{11}$ is an isoxazole, —C(O)OH, or a 5- or 6-membered heteroaryl group, wherein the isoxazole or the 5- or 6-membered heteroaryl group may be optionally substituted with one or two halo, $NH_2$ or $CH_3$ substituents;
X is $CH_2$, NH, O;
r is 0, 1 or 2;
s is 0, 1 or 2;
t is 0 or 1;
u is 0, 1 or 2;
with the proviso that no more than two $R_{10}$ groups represent OH or $CH_2OH$.

In one aspect, the present invention provides a pharmaceutical composition comprising a) a compound of formula (I), or a pharmaceutically acceptable salt thereof, and b) one or more pharmaceutically acceptable excipients.

In a further aspect, the present invention provides a compound of formula (I), or a pharmaceutically acceptable salt thereof, for use in therapy.

Compounds of formula (I), and pharmaceutically acceptable salts thereof, are modulators of RORγ and can be useful in the treatment of inflammatory, metabolic and autoimmune diseases mediated by RORγ, such as asthma, chronic obstructive pulmonary disease (COPD) and bronchitis, allergic diseases including allergic rhinitis and atopic dermatitis, cystic fibrosis, lung allograph rejection, multiple sclerosis, rheumatoid arthritis, juvenile rheumatoid arthritis, Osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBS), inflammatory bowel syndrome (IBD), Sjorgen's syndrome, optic neuritis, type I diabetes, neuromyelitis optica, Myastehnia Gravis, uveitis, Guillain-Barre syndrome, psoriatic arthritis, Graves' disease, scleritis.

In a further aspect, the present invention provides a compound of formula (I), or a pharmaceutically acceptable salt thereof, for use in the treatment of asthma or chronic obstructive pulmonary disease.

In a further aspect, the present invention is directed to a method of treatment of an inflammatory, metabolic or autoimmune disease mediated by RORγ, which comprises administering to a subject in need thereof, a safe and therapeutically effective amount of a compound of formula (I), or a pharmaceutically acceptable salt thereof.

In yet a further aspect, the present invention is directed to a method of treating chronic obstructive pulmonary disease or asthma, which comprises administering to a subject in need thereof, a safe and therapeutically effective amount of a compound of formula (I), or a pharmaceutically acceptable salt thereof.

DETAILED DESCRIPTION OF THE INVENTION

In a first aspect, the present invention is directed to a compound of formula (I), or a pharmaceutically acceptable salt thereof:

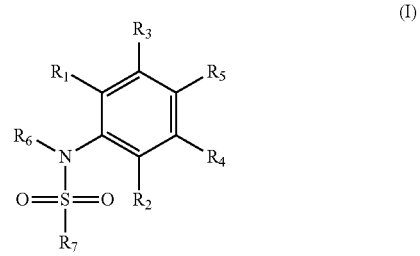

wherein
$R_1$ and $R_2$ are independently selected from the group consisting of H, $CF_3$, halo, $C_{1-3}$alkyl and $C_{1-3}$-alkoxy;
$R_3$ and $R_4$ are independently selected from the group consisting of H, $CF_3$, halo, $CH_3$ and $OCH_3$;
$R_5$ is selected from the group consisting of H, $CF_3$, halo, OH, $CH_2OH$, $C_{1-4}$alkyl, $CH_2$-cyclopropyl and $C_{1-4}$alkoxy, wherein $C_{1-4}$alkyl and $C_{1-4}$alkoxy, may be optionally substituted with one or two OH substituents;
$R_6$ is selected from the group consisting of $C_{3-5}$alkyl and —$CH_2$—$C_{3-4}$cycloalkyl;
$R_7$ is selected from the group consisting of

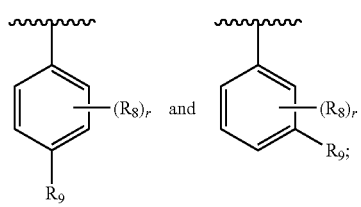

$R_8$ is selected from the group consisting of $C_{1-3}$alkyl, $C_{1-3}$alkoxy, $CH_2CN$, $CH_2OH$, OH, CN and halo;

$R_9$ is the group —$(CHR_{10})_s$—$(X)_t$—$(CHR_{10})_u$—$R_{11}$;

each $R_{10}$ is independently selected from the group consisting of H, OH or $CH_2OH$;

$R_{11}$ is an isoxazole, —C(O)OH, or a 5- or 6-membered heteroaryl group, wherein the isoxazole or the 5- or 6-membered heteroaryl group may be optionally substituted with one or two halo, $NH_2$ or $CH_3$ substituents;

X is $CH_2$, NH, O;

r is 0, 1 or 2;

s is 0, 1 or 2;

t is 0 or 1;

u is 0, 1 or 2;

with the proviso that no more than two $R_{10}$ groups represent OH or $CH_2OH$.

In a further aspect, the present invention provides subsets of the compounds of formula (I), of formula (Ia-Ig), or a pharmaceutically acceptable salt thereof:

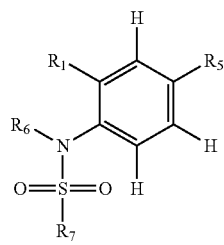
(Ia)

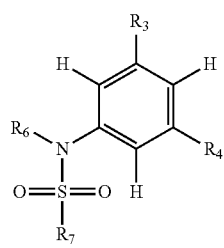
(Ib)

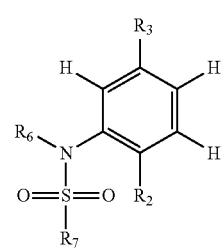
(Ic)

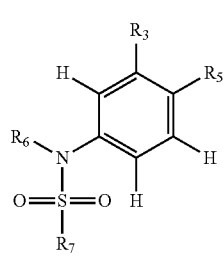
(Id)

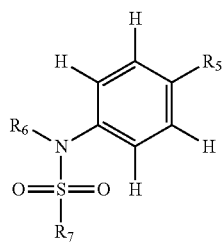
(Ie)

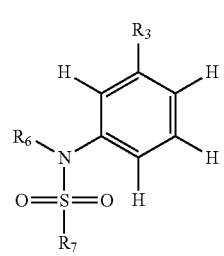
(If)

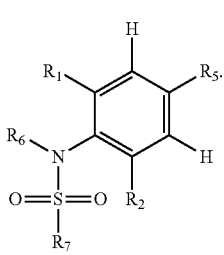
(Ig)

In a further aspect, the present invention provides subsets of the compounds of formula (I), of formula (Ia-Ic), or a pharmaceutically acceptable salt thereof:

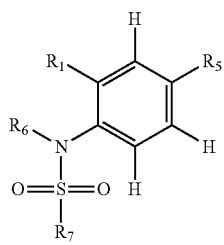
(Ia)

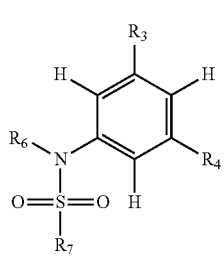
(Ib)

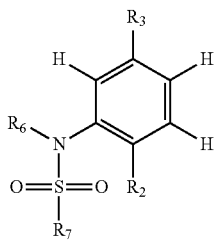

(Ic)

In a further aspect, the present invention provides a subset of compounds of formula (I), of formula (Ia), or a pharmaceutically acceptable salt thereof:

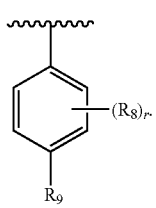

(Ia)

In a further aspect, the present invention provides a subset of compounds of formula (I), of formula (Ia) above, or a pharmaceutically acceptable salt thereof, wherein $R_1$ and $R_5$ are each independently $CH_3$ or halo.

In a further aspect, the present invention provides a subset of compounds of formula (I), of formula (Ia) above, or a pharmaceutically acceptable salt thereof, wherein $R_1$ and $R_5$ are $CH_3$.

In yet a further aspect of the present invention, $R_6$ is selected from the group consisting of propyl, isobutyl and —$CH_2$cyclopropyl.

In yet a further aspect of the present invention, $R_6$ is isobutyl.

In a further aspect of the present invention, $R_7$ is:

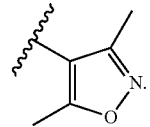 [SMILES: *c1c(C)noc1C]

In a further aspect of the present invention, r is 0.
In a further aspect of the present invention, r is 1 and $R_8$ is $C_{1-3}$alkyl or $C_{1-3}$alkoxy.
In a further aspect of the present invention, r is 1 and $R_8$ is $CH_3$ or —$OCH_3$.
In a further aspect of the present invention, r is 1 and $R_8$ is $CH_2OH$.
In a further aspect of the present invention, s is 0.
In a further aspect of the present invention, s is 1.
In a further aspect of the present invention, u is 1.
In a further aspect of the present invention, u is 0.
In a further aspect of the present invention, t is 1 and X is O.
In a further aspect of the present invention, each $R_{10}$ is H.

In a further aspect of the present invention, $R_{11}$ is 3,5-dimethylisoxazole, of formula:

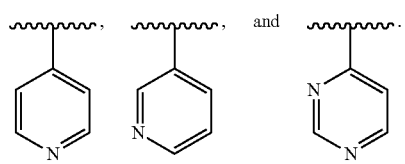

In a further aspect of the present invention, $R_{11}$ is selected from the group consisting of:

In a further aspect of the present invention, $R_{11}$ is selected from the group consisting of:

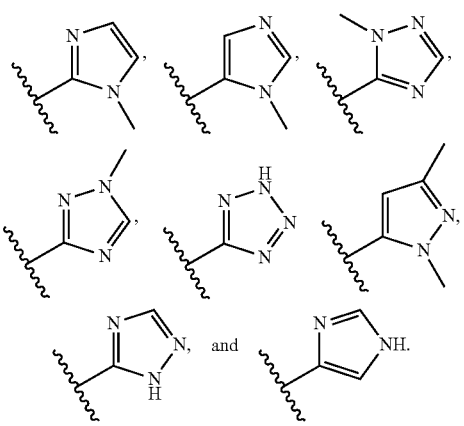

In a further aspect of the present invention, the $R_{11}$ group is unsubstituted.

It is understood that the present invention covers all combinations of substituent groups referred to herein above.

Specific examples of compounds of formula (I) are:
N-(4-butyl-2-methylphenyl)-N-isobutyl-4-(pyridin-4-yloxy)benzenesulfonamide;
N-(4-butyl-2-methylphenyl)-4-{[(3,5-dimethyl-4-isoxazolyl)methyl]oxy}-N-(2-methylpropyl)benzenesulfonamide;
4-((3,5-dimethylisoxazol-4-yl)methoxy)-N-(2,4-dimethylphenyl)-N-isobutylbenzenesulfonamide;
4-{[(3,5-dimethyl-4-isoxazolyl)methyl]oxy}-N-(4-fluoro-2-methylphenyl)-N-(2-methylpropyl)benzenesulfonamide;
N-(2,4-difluorophenyl)-4-{[(3,5-dimethyl-4-isoxazolyl)methyl]oxy}-N-(2-methylpropyl)benzenesulfonamide;
N-(4-butylphenyl)-4-{[(3,5-dimethyl-4-isoxazolyl)methyl]oxy}-N-(2-methylpropyl)benzenesulfonamide;
4-{[(3,5-dimethyl-4-isoxazolypmethyl]oxy}-N-[4-(1-methylethyl)phenyl]-N-(2-methylpropyl)benzenesulfonamide;
4-{[(3,5-dimethyl-4-isoxazolypmethyl]oxy}-N-(2-fluoro-4-methylphenyl)-N-(2-methylpropyl)benzenesulfonamide;
N-(4-chlorophenyl)-4-((3,5-dimethylisoxazol-4-yl)methoxy)-N-isobutylbenzenesulfonamide;

4-((3,5-dimethylisoxazol-4-yl)methoxy)-N-isobutyl-N-(4-propylphenyl)benzenesulfonamide;
4-((3,5-dimethylisoxazol-4-yl)methoxy)-N-isobutyl-N-(3-(trifluoromethyl)phenyl)benzenesulfonamide;
4-((3,5-dimethylisoxazol-4-yl)methoxy)-N-isobutyl-N-(2-methyl-5-(trifluoromethyl)phenyl)benzenesulfonamide;
4-((3,5-dimethylisoxazol-4-yl)methoxy)-N-isobutyl-N-phenylbenzenesulfonamide;
4-((3,5-dimethylisoxazol-4-yl)methoxy)-N-(2-ethylphenyl)-N-propylbenzenesulfonamide;
4-{[(3,5-dimethyl-4-isoxazolyl)methyl]oxy}-N-(3-methylphenyl)-N-(2-methylpropyl)benzenesulfonamide;
4-{[(3,5-dimethyl-4-isoxazolyl)methyl]oxy}-N-(2,5-dimethyl phenyl)-N-(2-methylpropyl)benzenesulfonamide;
4-{[(3,5-dimethyl-4-isoxazolyl)methyl]oxy}-N-(3-ethyl phenyl)-N-(2-methylpropyl)benzenesulfonamide;
N-(5-chloro-2-fluorophenyl)-4-{[(3,5-dimethyl-4-isoxazolyl)methyl]oxy}-N-(2-methylpropyl)benzenesulfonamide;
N-(2-chloro-5-fluorophenyl)-4-{[(3,5-dimethyl-4-isoxazolyl)methyl]oxy}-N-(2-methylpropyl)benzenesulfonamide;
4-{[(3,5-dimethyl-4-isoxazolyl)methyl]oxy}-N-(4-methyl phenyl)-N-(2-methylpropyl)benzenesulfonamide;
N-(cyclopropylmethyl)-4-{[(3,5-dimethyl-4-isoxazolyl)methyl]oxy}-N-(2,4-dimethylphenyl)benzenesulfonamide;
4-((3,5-dimethylisoxazol-4-yl)methoxy)-N-(4-hydroxy-2-methylphenyl)-N-isobutylbenzenesulfonamide;
4-((3,5-dimethylisoxazol-4-yl)methoxy)-N-phenyl-N-propylbenzenesulfonamide;
N-(4-butyl-2-methylphenyl)-N-isobutyl-4-(pyridin-3-yloxy)benzenesulfonamide;
4-{[(3,5-dimethyl-4-isoxazolypmethyl]oxy}-N-[3-(methyloxy)phenyl]-N-(2-methylpropyl)benzenesulfonamide;
N-(2,4-dimethylphenyl)-4-hydroxy-N-isobutylbenzenesulfonamide;
N-(2,4-dimethylphenyl)-N-(2-methylpropyl)-4-[(4-pyridinylmethyl)oxy]benzenesulfonamide;
N-(5-chloro-2-fluorophenyl)-N-isobutyl-4-(pyridin-4-ylmethoxy)benzenesulfonamide;
N-(3-fluoro-5-methylphenyl)-N-isobutyl-4-(pyridin-4-ylmethoxy)benzenesulfonamide;
N-(3,5-dimethylphenyl)-N-isobutyl-4-(pyridin-4-ylmethoxy)benzenesulfonamide;
N-isobutyl-N-(5-methoxy-2-methylphenyl)-4-(pyridin-4-ylmethoxy)benzenesulfonamide;
N-(2,5-difluorophenyl)-N-isobutyl-4-(pyridin-4-ylmethoxy)benzenesulfonamide;
N-(5-fluoro-2-methylphenyl)-N-isobutyl-4-(pyridin-4-ylmethoxy)benzenesulfonamide;
N-(2,5-dimethylphenyl)-N-isobutyl-4-(pyridin-4-ylmethoxy)benzenesulfonamide;
N-(3-ethylphenyl)-N-isobutyl-4-(pyridin-4-ylmethoxy)benzenesulfonamide;
N-isobutyl-N-(3-methoxyphenyl)-4-(pyridin-4-ylmethoxy)benzenesulfonamide;
N-isobutyl-4-(pyridin-4-ylmethoxy)-N-(m-tolyl)benzenesulfonamide;
N-[4-(cyclopropylmethyl)-2,6-dimethyl phenyl]-4-{[(3,5-dimethyl-4-isoxazolyl)methyl]oxy}-N-(2-methylpropyl)benzenesulfonamide;
N-(3,5-difluorophenyl)-N-(2-methylpropyl)-4-[(phenylmethyl)oxy]benzenesulfonamide;
N-(2,5-difluorophenyl)-4-{[(3,5-dimethyl-4-isoxazolyl)methyl]oxy}-N-(2-methylpropyl)benzenesulfonamide;
N-(3,5-dichlorophenyl)-4-{[(3,5-dimethyl-4-isoxazolyl)methyl]oxy}benzenesulfonamide;
N-(2,5-dichlorophenyl)-4-{[(3,5-dimethyl-4-isoxazolyl)methyl]oxy}-N-(2-methylpropyl)benzenesulfonamide;
N-(3,4-dichlorophenyl)-4-{[(3,5-dimethyl-4-isoxazolyl)methyl]oxy}-N-(2-methylpropyl)benzenesulfonamide;
N-(3,5-difluorophenyl)-4-{[(3,5-dimethyl-4-isoxazolyl)methyl]oxy}-N-(2-methylpropyl)benzenesulfonamide;
4-{[(3,5-dimethyl-4-isoxazolyl)methyl]oxy}-N-(3,4-dimethyl phenyl)-N-(2-methylpropyl)benzenesulfonamide;
4-{[(3,5-dimethyl-4-isoxazolypmethyl]oxy}-N-(3-fluoro-5-methylphenyl)-N-(2-methylpropyl)benzenesulfonamide;
4-{[(3,5-dimethyl-4-isoxazolyl)methyl]oxy}-N-(3,5-dimethyl phenyl)-N-(2-methylpropyl)benzenesulfonamide;
4-{[(3,5-dimethyl-4-isoxazolyl)methyl]oxy}-N-[2-methyl-5-(methyloxy)phenyl]-N-(2-methylpropyl)benzenesulfonamide;
4-{[(3,5-dimethyl-4-isoxazolyl)methyl]oxy}-N-(5-fluoro-2-methylphenyl)-N-(2-methylpropyl)benzenesulfonamide;
N-(3-chlorophenyl)-4-{[(3,5-dimethyl-4-isoxazolyl)methyl]oxy}-N-(2-methylpropyl)benzenesulfonamide;
4-((1H-imidazol-2-yl)methoxy)-N-(2,4-dimethylphenyl)-N-isobutylbenzenesulfonamide;
N-(2,4-dimethylphenyl)-N-isobutyl-4-(pyridin-4-ylmethoxy)benzenesulfonamide;
4-((1,3-dimethyl-1H-pyrazol-5-yl)methoxy)-N-(2,4-dimethylphenyl)-N-isobutylbenzenesulfonamide;
N-(2,4-dimethylphenyl)-N-isobutyl-4-((5-methylisoxazol-3-yl)methoxy)benzenesulfonamide;
N-(2,4-dimethylphenyl)-N-isobutyl-4-((pyridin-4-yloxy)methyl)benzenesulfonamide;
N-(2,4-dimethylphenyl)-N-isobutyl-4-((pyrimidin-4-yloxy)methyl)benzenesulfonamide;
N-(2,4-dimethylphenyl)-N-isobutyl-4-((pyridin-4-ylmethoxy)methyl)benzenesulfonamide;
3-(((3,5-dimethylisoxazol-4-yl)methoxy)methyl)-N-(2,4-dimethylphenyl)-N-isobutylbenzenesulfonamide;
N-(2,4-dimethylphenyl)-N-isobutyl-3-((pyridin-4-ylmethoxy)methyl)benzenesulfonamide;
N-(2,4-dimethylphenyl)-N-isobutyl-4-((4-methyl-1H-imidazol-5-yl)methoxy)benzenesulfonamide;
N-(2,4-dimethylphenyl)-N-isobutyl-4-((1-methyl-1H-1,2,4-triazol-3-yl)methoxy)benzenesulfonamide;
N-(2,4-dimethylphenyl)-N-isobutyl-4-((1-methyl-1H-imidazol-2-yl)methoxy)benzenesulfonamide;
4-((1H-imidazol-4-yl)methoxy)-N-(2,4-dimethylphenyl)-N-isobutylbenzenesulfonamide;
4-((3,5-dimethylisoxazol-4-yl)methoxy)-N-isobutyl-N-(5-isopropyl-2-methylphenyl)-benzenesulfonamide;
3-((3,5-dimethylisoxazol-4-yl)methoxy)-N-(2,4-dimethylphenyl)-N-isobutylbenzenesulfonamide;
4-((3,5-dimethylisoxazol-4-yl)methoxy)-N-isobutyl-N-(o-tolyl)-benzenesulfonamide;
N-(2,4-dimethylphenyl)-N-isobutyl-3-(pyridin-4-ylmethoxy)benzenesulfonamide;
N-(2,4-dimethylphenyl)-N-isobutyl-3-((pyrimidin-4-ylmethoxy)methyl)benzenesulfonamide;
N-(2,4-dimethylphenyl)-N-isobutyl-4-(pyridin-4-ylmethoxy)benzenesulfonamide;
N-(2,4-dimethylphenyl)-N-isobutyl-4-(2-(pyridin-4-yl)ethoxy)benzenesulfonamide;
4-(2-(3,5-dimethylisoxazol-4-yl)ethoxy)-N-(2,4-dimethylphenyl)-N-isobutylbenzenesulfonamide;
N-(2,4-dimethylphenyl)-N-isobutyl-4-(pyrimidin-4-ylmethoxy)benzenesulfonamide;
N-(4-bromo-2-methylphenyl)-4-((3,5-dimethylisoxazol-4-yl)methoxy)-N-isobutylbenzenesulfonamide;
N-(2,4-dimethylphenyl)-4-((2-fluoropyridin-4-yl)methoxy)-N-isobutylbenzenesulfonamide;

N-(2,4-dimethylphenyl)-N-isobutyl-4-((1-methyl-1H-imidazol-5-yl)methoxy)benzenesulfonamide;
N-(2,4-dimethylphenyl)-N-isobutyl-4-((1-methyl-1H-1,2,4-triazol-5-yl)methoxy)benzenesulfonamide;
4-((3,5-dimethylisoxazol-4-yl)methoxy)-N-(2,4-dimethylphenyl)-N-isobutyl-3-methoxybenzenesulfonamide;
N-(2,4-dimethylphenyl)-4-(2-hydroxy-2-(pyridin-4-yl)ethoxy)-N-isobutylbenzenesulfonamide;
4-((2-aminopyridin-4-yl)methoxy)-N-(2,4-dimethylphenyl)-N-isobutylbenzenesulfonamide;
[(4-{[(2,4-dimethylphenyl)(2-methylpropyl)amino]sulfonyl]-2,3-dimethylphenyl)oxy}acetic acid;
N-(2,4-dimethylphenyl)-4-(1-hydroxy-2-((pyridin-3-ylmethyl)amino)ethyl)-N-isobutylbenzenesulfonamide;
3-[(4-{[(4-butyl-2-methylphenyl)(2-methylpropyl)amino]sulfonyl]-2-methylphenyl)oxy}propanoic acid;
N-(2,4-dimethylphenyl)-4-(1-hydroxy-2-((pyridin-4-ylmethyl)amino)ethyl)-N-isobutylbenzenesulfonamide;
4-((3,5-dimethylisoxazol-4-yl)methoxy)-N-(4-(2-hydroxypropan-2-yl)-2-methylphenyl)-N-isobutylbenzenesulfonamide;
4-((3,5-dimethylisoxazol-4-yl)methoxy)-N-(4-(2-hydroxyethoxy)-2-methylphenyl)-N-isobutylbenzenesulfonamide;
4-((3,5-dimethylisoxazol-4-yl)methoxy)-N-(4-(hydroxymethyl)-2-methylphenyl)-N-isobutylbenzenesulfonamide;
4-((3,5-dimethylisoxazol-4-yl)methoxy)-N-(4-(3-hydroxypropyl)phenyl)-N-isobutylbenzenesulfonamide;
4-(4-(N-(2,4-dimethylphenyl)-N-isobutylsulfamoyl)phenyl)butanoic acid;
4-((3,5-dimethylisoxazol-4-yl)methoxy)-N-(4-ethylphenyl)-N-isobutylbenzenesulfonamide;
(R)-3-((4-(N-(2,4-dimethylphenyl)-N-isobutylsulfamoyl)-2-methylphenyl)amino)-4-hydroxybutanoic acid;
(S)-2-((4-(N-(2,4-dimethylphenyl)-N-isobutylsulfamoyl)phenyl)amino)-3-hydroxypropanoic acid;
(S)-3-((4-(N-(2,4-dimethylphenyl)-N-isobutylsulfamoyl)phenyl)amino)-4-hydroxybutanoic acid;
N-(2,4-dimethylphenyl)-N-isobutyl-4-(2H-tetrazol-5-yl)benzenesulfonamide;
(R)-3-((4-(N-(2,4-dimethylphenyl)-N-isobutylsulfamoyl)phenyl)amino)-4-hydroxybutanoic acid;
3-(4-(N-isobutyl-N-(2-methyl-5-(trifluoromethyl)phenyl)sulfamoyl)phenyl)propanoic acid;
3-(4-(N-isobutyl-N-(2-methyl-5-(trifluoromethyl)phenyl)sulfamoyl)phenyl)-2,2-dimethylpropanoic acid;
5-(N-(2,4-dimethylphenyl)-N-isobutylsulfamoyl)-2-methoxybenzoic acid;
2-((4-(N-(2,4-dimethylphenyl)-N-isobutylsulfamoyl)phenyl)amino)-3-hydroxypropanoic acid;
N-(2,6-difluorophenyl)-4-{[(3,5-dimethyl-4-isoxazolyl)methyl]oxy}-N-(2-methylpropyl)benzenesulfonamide;
2-bromo-5-(N-(4-ethylphenyl)-N-isobutylsulfamoyl)benzoic acid;
2-(4-(N-(4-butyl-2-methylphenyl)-N-isobutylsulfamoyl)-2-methylphenoxy)acetic acid;
4-((2-(dideuterioamino)pyridin-4-yl)methoxy)-N-(2,4-dimethylphenyl)-N-isobutylbenzenesulfonamide;
N-(2,4-dimethylphenyl)-4-(1-hydroxy-3-(2H-tetrazol-5-yl)propyl)-N-isobutylbenzenesulfonamide;
N-(2,4-dimethylphenyl)-4-(1-hydroxy-2-(2H-tetrazol-5-yl)ethyl)-N-isobutylbenzenesulfonamide;
N-(2,4-dimethylphenyl)-4-(2-hydroxy-1-(2H-tetrazol-5-yl)propan-2-yl)-N-isobutylbenzenesulfonamide;
N-(4-(1,3-dihydroxypropan-2-yl)phenyl)-4-(((3,5-dimethylisoxazol-4-yl)oxy)methyl)-N-isobutylbenzenesulfonamide;
2-(4-(N-(2,4-dimethylphenyl)-N-isobutylsulfamoyl)phenyl)acetic acid;
4-(N-(2,4-dimethylphenyl)-N-isobutylsulfamoyl)benzoic acid;
4-(N-(2,4-dimethylphenyl)-N-isobutylsulfamoyl)benzoic acid; and
3-(N-(2,4-dimethylphenyl)-N-isobutylsulfamoyl)benzoic acid.

As used herein, the term "alkyl" refers to a saturated hydrocarbon chain having the specified number of member atoms. For example, $C_{1-4}$ alkyl refers to an alkyl group having from 1 to 4 member atoms. Unless otherwise stated, alkyl groups are unsubstituted. Alkyl groups may be straight chain or branched. The term "alkyl" includes, but is not limited to, methyl, ethyl, propyl (n-propyl and isopropyl), butyl (n-butyl, sec-butyl, isobutyl and tert-butyl).

As used herein, the term "alkoxy" refers to an —O-alkyl group wherein "alkyl" is defined above.

As used herein, the term "halo" refers to the halogen radicals fluoro, chloro, bromo and iodo.

As used herein, the phrase "5- or 6-membered heteroaryl" indicates an aromatic ring containing 5 or 6 member atoms, wherein the member atoms are either carbon or nitrogen. The 5- or 6-membered heteroaryl group may contain one, two, three or four nitrogen atoms as member atoms of the ring.

As used herein, the phrase "optionally substituted" indicates that a group may be unsubstituted or substituted with one or two substituents as defined herein. "Substituted" in reference to a group indicates that a hydrogen atom attached to a member atom with a group is replaced.

As used herein, the term "RORγ" refers to all isoforms of this member of the ROR family, including RORγ1 and RORγt.

As used herein, the term "RORγ modulator" refers to a chemical compound of formula (I) that inhibits, either directly or indirectly, the activity of RORγ. RORγ modulators include antagonists and inverse agonists of RORγ.

The compounds of formula (I) and pharmaceutically acceptable salts thereof may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a compound of formula (I), or in any chemical structure illustrated herein, is not specified the structure is intended to encompass all individual stereoisomers and all mixtures thereof. Thus, compounds of formula (I) and pharmaceutically acceptable salts thereof containing one or more chiral center may be used as racemic mixtures, enantiomerically enriched mixtures, or as enantiomerically pure individual stereoisomers.

Individual stereoisomers of a compound of formula (I), or a pharmaceutically acceptable salt thereof, which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

In certain aspects, compounds of formula (I) may contain an acidic functional group. In certain other embodiments, compounds of formula (I) may contain a basic functional group. Thus, the skilled artisan will appreciate that pharmaceutically-acceptable salts of the compounds of formula (I) may be prepared. Indeed, in certain embodiments of the invention, pharmaceutically-acceptable salts of the compounds of formula (I) may be preferred over the respective free base or free acid because such salts may impart greater stability or solubility to the molecule thereby facilitating formulation into a dosage form.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopaedia of Pharmaceutical Technology, Marcel Dekker Inc, New York 1996, Volume 13, page 453-497. Other salts that are not deemed pharmaceutically acceptable may be useful in the preparation of compounds of formula (I) and are included within the scope of the invention, such as ammonia and trifluoroacetic acid. The present invention encompasses all possible stoichiometric and non-stoichiometric forms of the salts of the compounds of formula (I).

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

The invention also includes all suitable isotopic variations of a compound of formula (I) or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^2$H, $^3$H, $^{13}$C, $^{14}$C, $^{15}$N, $^{17}$O, $^{18}$O, $^{18}$F and $^{36}$Cl, respectively. Certain isotopic variations of a compound of formula (I) or a salt or solvate thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

A compound of formula (I), or a pharmaceutically acceptable salt thereof, may be in amorphous or crystalline form. Moreover, a compound of formula (I), or a pharmaceutically acceptable salt thereof, may exist in one or more crystalline forms. Consequently, the present invention includes within its scope all forms of a compound of formula (I), or a pharmaceutically acceptable salt thereof.

The person skilled in the art will appreciate that many organic compounds can form complexes with solvents in which they are reacted or from which they are precipitated or crystallised. These complexes are known as "solvates". Where the solvent is water the complex is known as a "hydrate". The present invention encompasses all solvates of the compounds of formula (I). In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

EXPERIMENTAL

Compounds of the invention may be prepared by methods known in the art of organic synthesis as set forth in part by the following synthesis schemes. In the following reaction schemes and hereafter, unless otherwise stated, all the groups are defined in the first aspect. It is also recognised that in all of the schemes described below, it is well understood that protecting groups for sensitive or reactive groups are employed where necessary in accordance with general principles of organic synthesis (T. W. Greene and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of the invention.

General Reaction Schemes

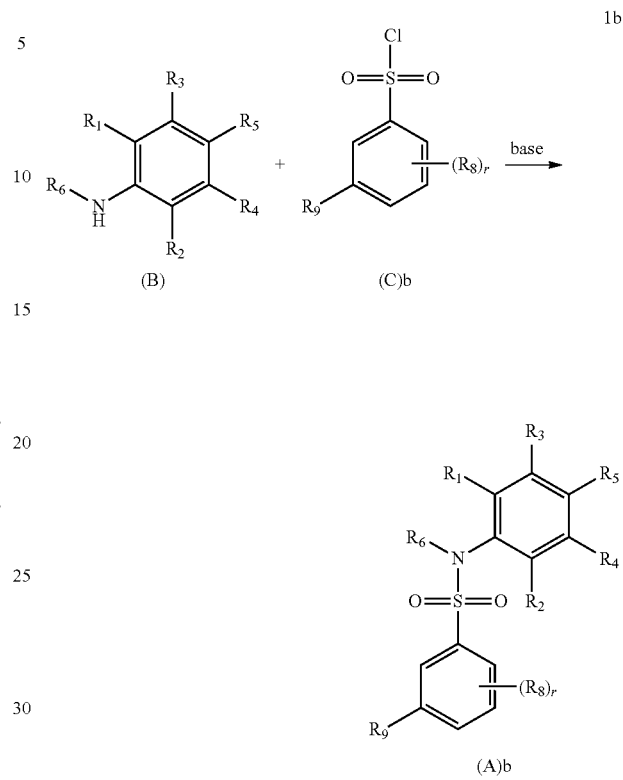

Compounds of formula (A)a and (A)b may be prepared from sulfonyl chlorides of formula (C)a and (C)b respectively, by reaction with an aniline of formula (B), according to Scheme 1a and 1b. Typical reaction conditions comprise mixing together a sulfonyl chloride of formula (C)a or (C)b with the appropriate aniline (B), in a basic solvent such as pyridine, for a suitable time, such as 16 hours, at a suitable temperature, such as ambient.

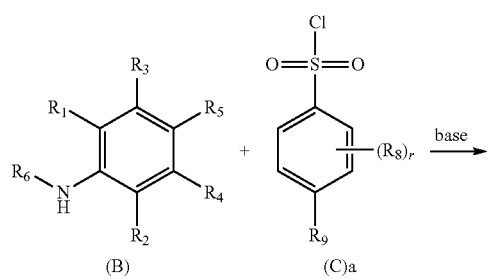

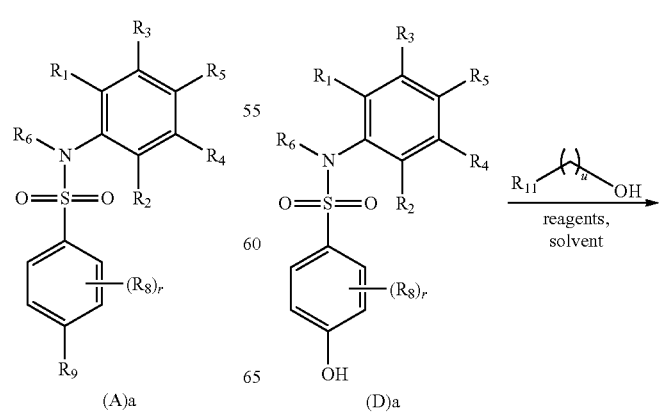

Scheme 3a and 3b

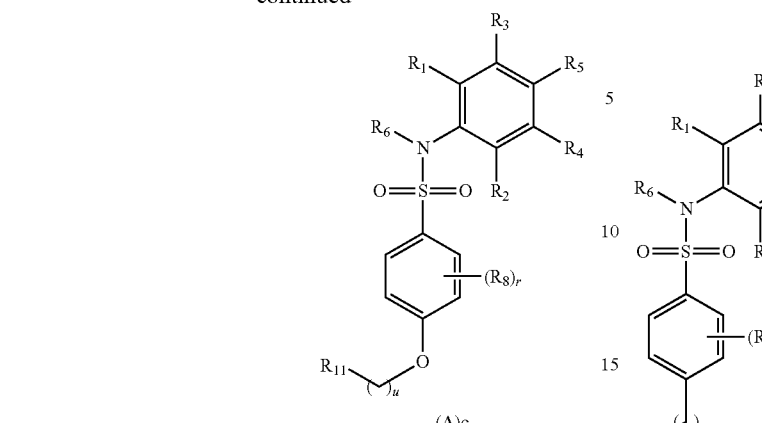

(A)c
u = 1, 2

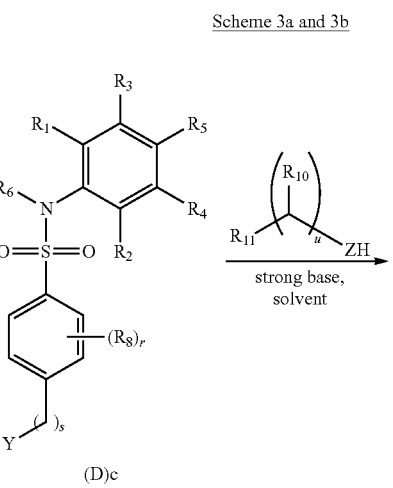

3a

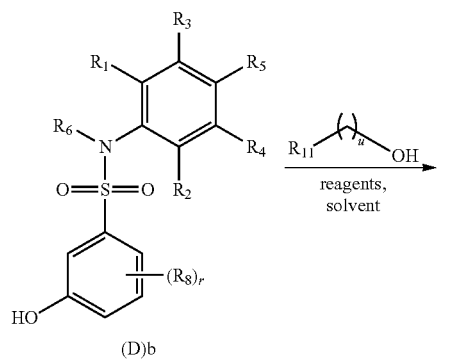

(D)b

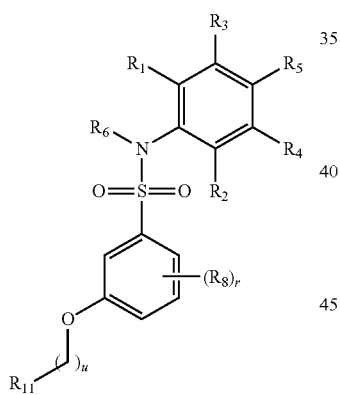

(A)d
u = 1, 2

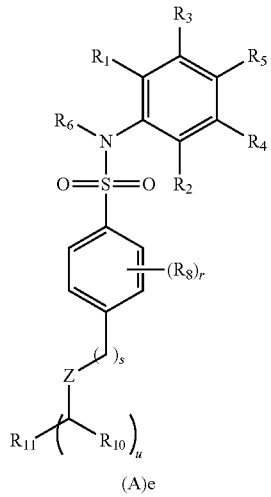

(A)e

Y = leaving group eg. Br, I, Cl, F, OTs
Z = O, NH
s = 0, 1, 2
u = 0, 1, 2

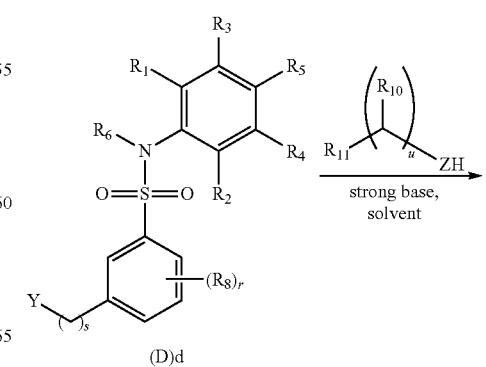

3b

Compounds of formula (A)c and (A)d may be prepared from intermediate compounds of formula (D)a and (D)b respectively, by coupling with an appropriately substituted alcohol according to Scheme 2a and 2b. Typical coupling conditions would include the 'Mitsunobu reaction' and comprise mixing the alcohol together with an intermediate compound of formula (D)a or (D)b and triphenylphosphine, in a suitable solvent, such as tetrahydrofuran. The mixture is then treated with a suitable coupling reagent, such as diisopropyl azodicarboxylate, and the reaction stirred for a suitable time, such as 16 hours, at a suitable temperature, such as ambient.

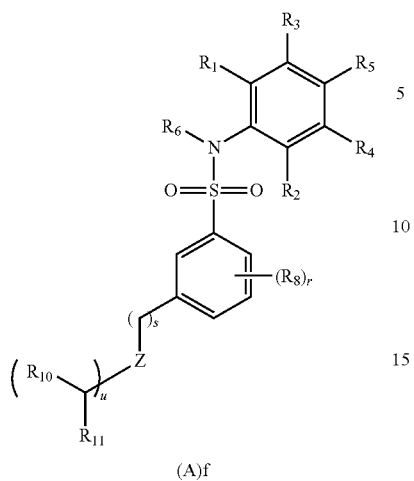

(A)f

Y = leaving group eg. Br, I, Cl, F, OTs
Z = O, NH
s = 0, 1, 2
u = 0, 1, 2

Compounds of formula (A)e and (A)f may be prepared from intermediate compounds of formula (D)c and (D)d respectively, by reaction with an appropriately substituted alkyl or heteroaromatic alcohol or amine according to Scheme 3a and 3b. Typical reaction conditions comprise mixing the alcohol or amine together with an intermediate compound of formula (D)c or (D)d, with a strong base such as sodium hydride, in a suitable solvent such as 2-methyltetrahydrofuran, under nitrogen at a suitable temperature, such as ambient for a suitable time, such as 3 hours.

Scheme 4a and 4b

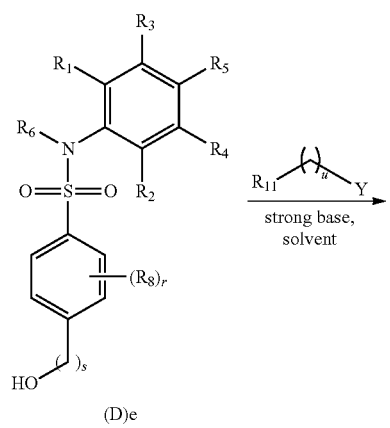

(D)e

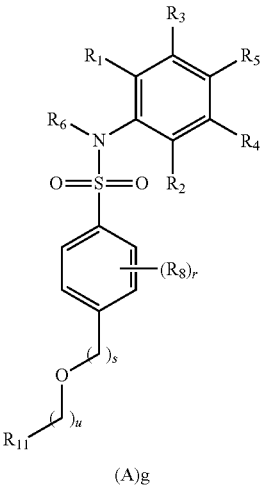

(A)g

Y = leaving group eg. Br, I, Cl, F, OTs
s = 0, 1, 2
u = 0, 1, 2

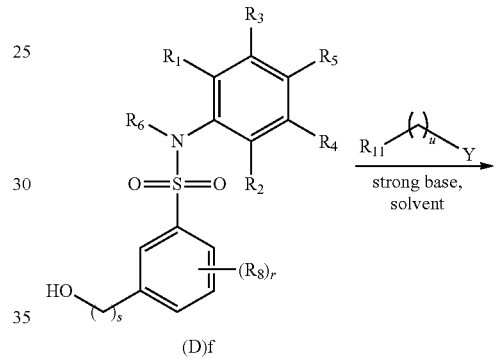

(D)f

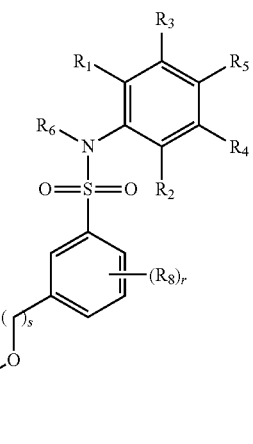

(A)h

Y = leaving group eg. Br, I, Cl, F, OTs
s = 0, 1, 2
u = 0, 1, 2

Compounds of formula (A)g and (A)h may be prepared from intermediate compounds of formula (D)e and (D)f respectively, by reaction with an appropriate alkylating agent according to Scheme 4a and 4b. Typical reaction conditions comprise mixing an intermediate compound of formula (D)e or (D)f, with a strong base such as sodium hydride in a suitable solvent, such as dimethylsulfoxide, for a suitable time, such as 5 minutes, under nitrogen. The mixture is then treated with the alkylating agent and stirred at a suitable temperature such as ambient for a suitable time, such as 18 hours.

Scheme 5a and 5b. Typical reaction conditions comprise mixing together a sulfonyl chloride of formula (E)a or (E)b with the appropriate aniline (B) in a basic solvent such as pyridine, for a suitable time, such as 16 hours, at a suitable temperature such as ambient.

$R_{12}$ may include functionality (which can be protected/masked) that is inert to reaction under the above conditions and may then be converted to $R_9$ in subsequent step(s). Suitable examples for $R_{12}$ can include -halo, —$(CHR_{10})_s$-halo, —OMe/ —OBn, —$CO_2Me$/ —$CO_2Et$, —CN, —NHAc (the latter four which may then be deprotected or transformed to —OH, —$CH_2OH$, —$CH_2NH_2$ and —$NH_2$ respectively using methods known to those skilled in the art of organic synthesis).

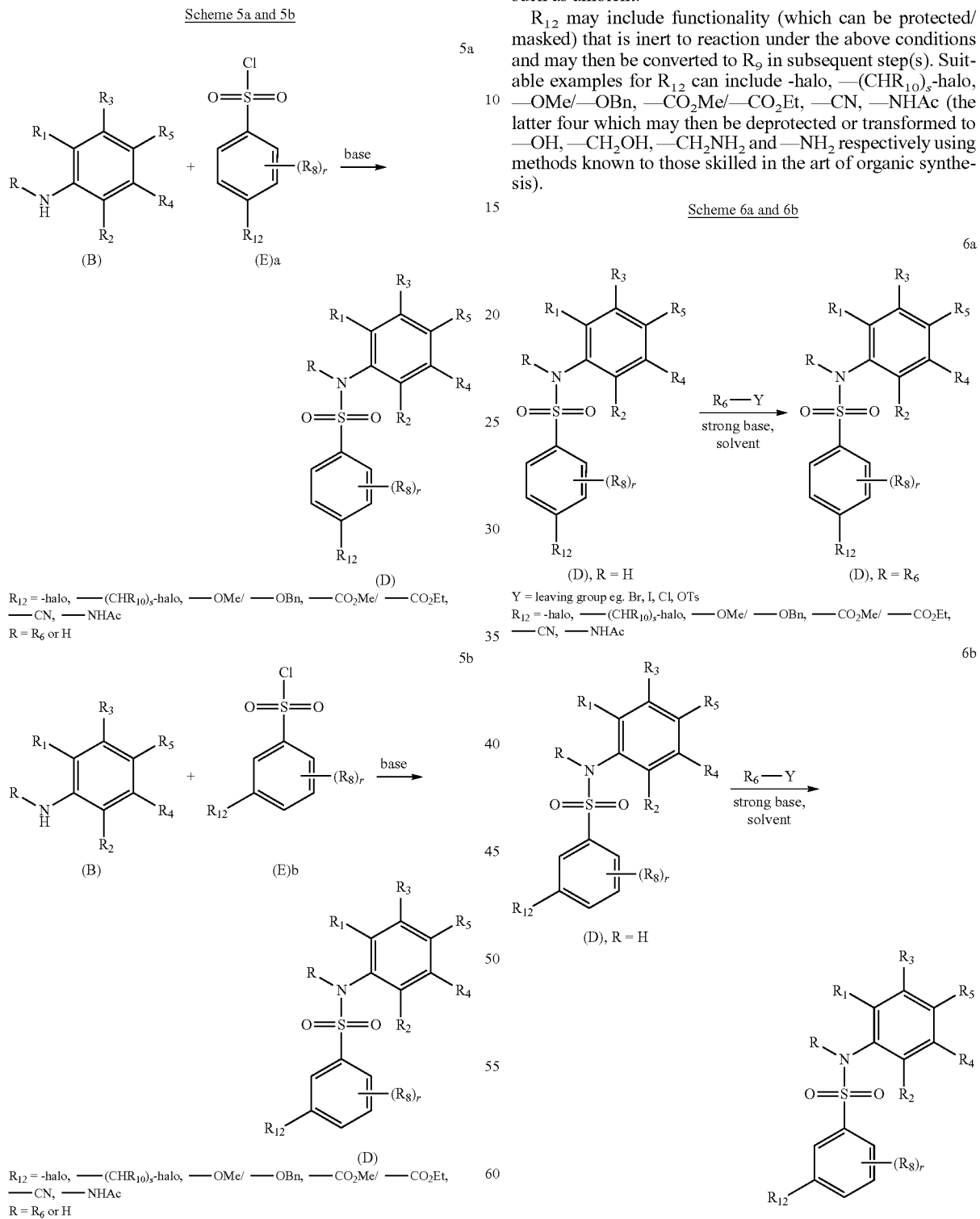

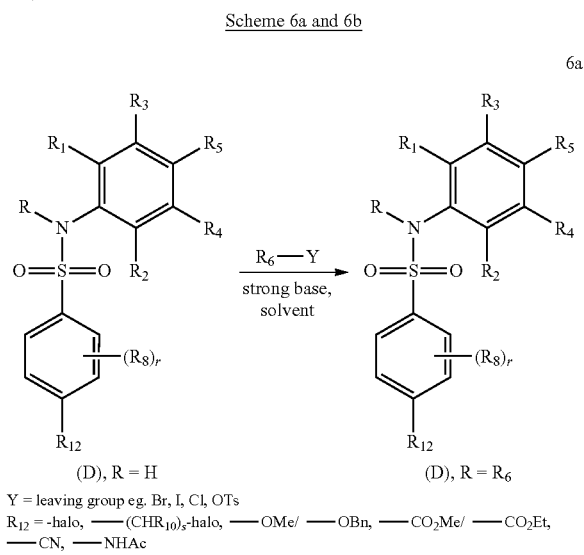

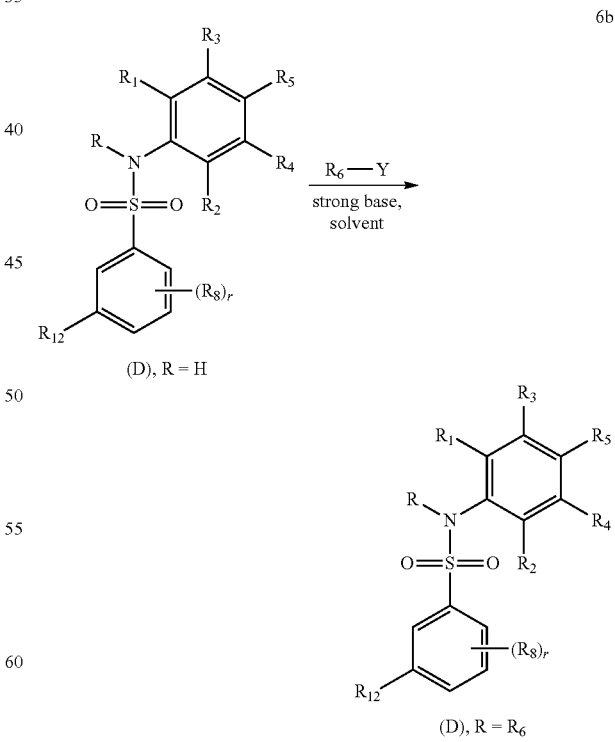

Key intermediate compounds of formula (D), where $R_{12}$ is a suitable functional group for later transformation into $R_9$; may be prepared from sulfonyl chlorides of formula (E)a and (E)b, by reaction with an aniline of formula (B) according to Compounds of formula (D) where R=$R_6$, may be prepared from intermediate compounds of formula (D), where R=H, by reaction with a suitable alkylating agent according to Scheme 6a and 6b. Typical reaction conditions comprise mixing together a compound of formula (D), where R=H, with a strong base, such as Barton's base, in a suitable solvent such as acetonitrile, for a suitable time, such as 1 hour, at a suitable temperature such as ambient. The mixture is then treated with the appropriate alkylating agent and heated in a sealed vessel to a suitable temperature, for example 150° C., by microwaves, for a suitable time, such as 25 minutes.

Secondary sulfonamide compounds of formula (F)a and (F)b may be prepared from sulfonyl chlorides of formula (C)a and (C)b respectively, by reaction with a primary aniline of formula (B), R=H, according to Scheme 7a and 7b. Typical reaction conditions comprise mixing together a sulfonyl chloride of formula (C)a or (C)b with the appropriate aniline (B), R=H, in a basic solvent such as pyridine, for a suitable time, such as 16 hours, at a suitable temperature such as ambient.

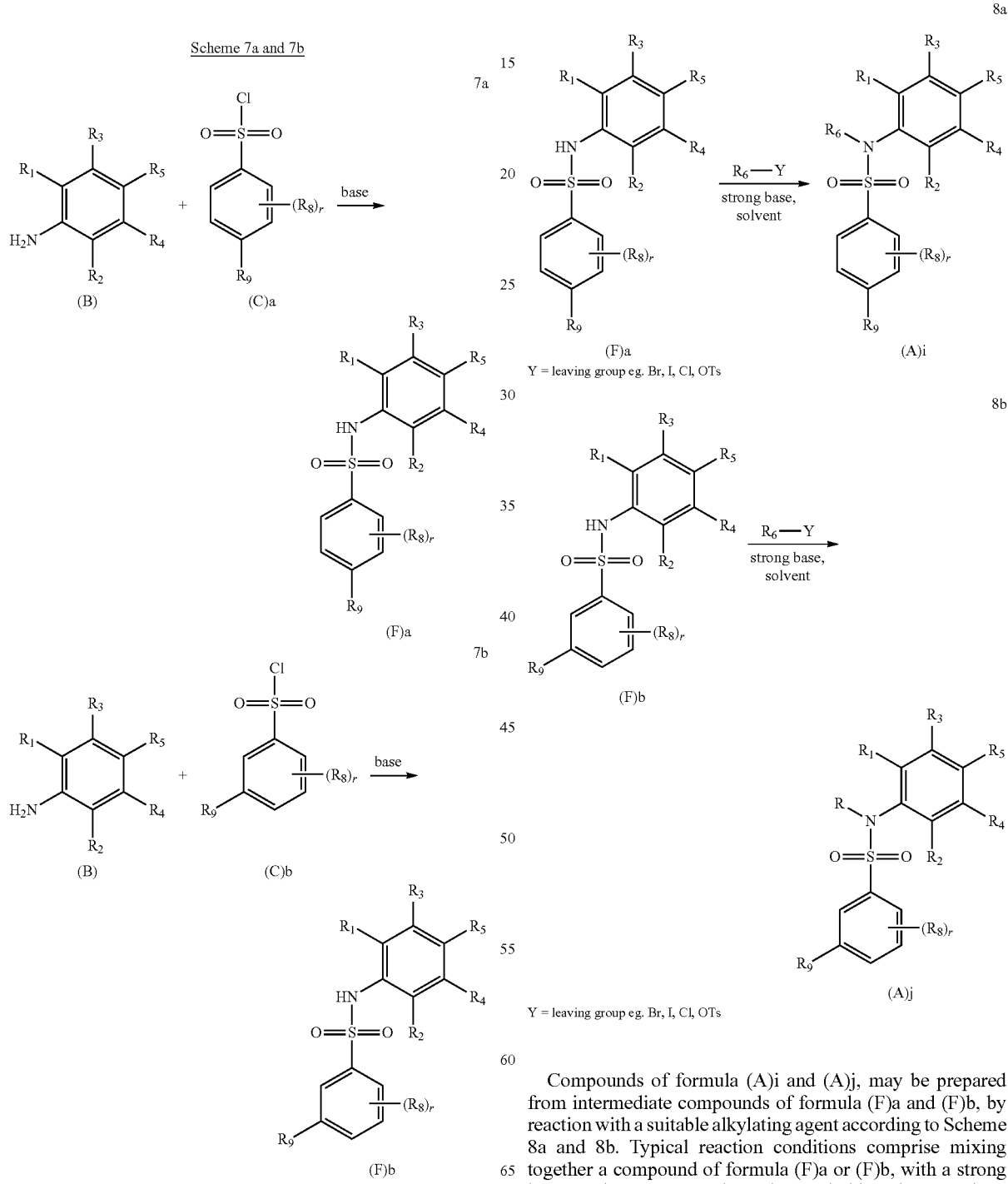

Compounds of formula (A)i and (A)j, may be prepared from intermediate compounds of formula (F)a and (F)b, by reaction with a suitable alkylating agent according to Scheme 8a and 8b. Typical reaction conditions comprise mixing together a compound of formula (F)a or (F)b, with a strong base, such as Barton's base, in a suitable solvent such as acetonitrile, for a suitable time, such as 1 hour, at a suitable temperature such as ambient. The mixture is then treated with the appropriate alkylating agent and heated in a sealed vessel to a suitable temperature, for example 150° C., by microwaves, for a suitable time, such as 25 minutes.

Scheme 9

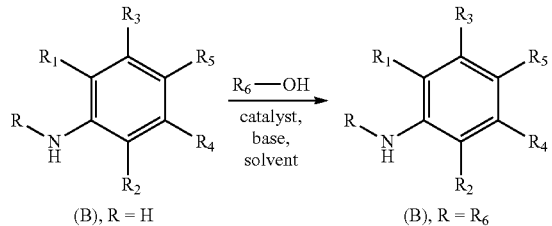

(B), R = H → (B), R = $R_6$

Secondary anilines of formula (B), R=$R_6$ may be prepared from primary anilines of formula (B), R=H, by reaction with an appropriate primary alcohol according to Scheme 9. Typical reaction conditions comprise mixing together a primary aniline (B), R=H, with the appropriate alcohol, a suitable base such as potassium iodide and a suitable catalyst such as pentamethylcyclopentadienyliridium(III) chloride in a suitable solvent, such as water. The mixture is then heated in a sealed vessel to a suitable temperature, for example 170° C., by microwaves, for a suitable time, such as 1 hour.

Scheme 10

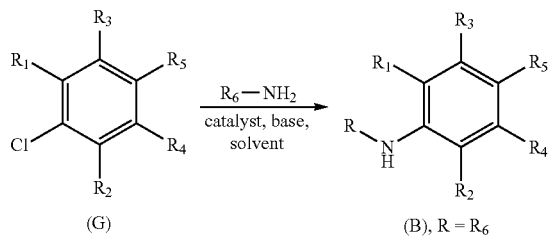

(G) → (B), R = $R_6$

Where $R_1$-$R_5$ should not be reactive towards palladium cross-coupling

Secondary anilines of formula (B), R=$R_6$ may be prepared from aryl chlorides of formula (G), by reaction with an appropriate primary alkylamine according to Scheme 10. Typical reaction conditions comprise mixing together an aryl chloride (G), with the appropriate primary alkyl amine, a suitable catalyst such as {1,3-bis[2,6-bis(1-methylethyl)phenyl]-2-imidazolidinyl}(chloro)(2-methyl-2-propen-1-yl)palladium and a suitable base such as lithium hexamethyldisilizide, in a suitable solvent, such as tetrahydrofuran. The mixture is then heated in a sealed vessel to a suitable temperature, for example 70° C., by microwaves, for a suitable time, such as 45 minutes.

Scheme 11

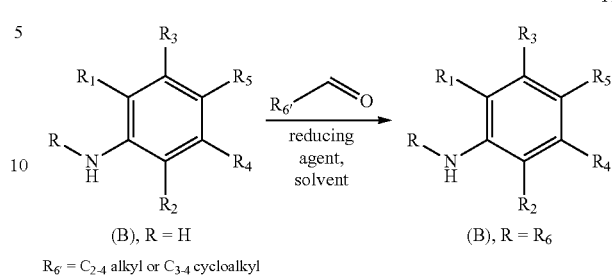

(B), R = H → (B), R = $R_6$ $R_{6'}$ = $C_{2-4}$ alkyl or $C_{3-4}$ cycloalkyl

A secondary aniline of formula (B), R=$R_6$ may be prepared from a primary aniline of formula (B), R=H, by reaction with an appropriate aldehyde according to Scheme 11. Typical reaction conditions comprise mixing together a primary aniline (B), R=H, with the appropriate aldehyde, in a suitable solvent such as tetrahydrofuran, for a suitable time, such as 20 minutes. The mixture is then treated with a suitable reducing agent, such as sodium triacetoxyborohydride and stirred for a suitable time, such as 18 hours, at a suitable temperature, such as ambient.

Scheme 12

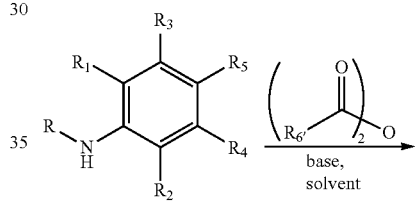

(B), R = H

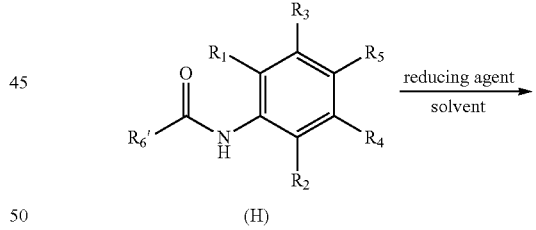

(H)

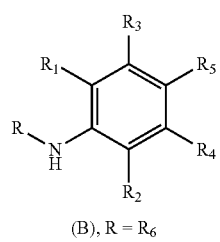

(B), R = $R_6$ $R_{6'}$ = $C_{2-4}$ alkyl or $C_{3-4}$ cycloalkyl

A secondary aniline of formula (B), R=$R_6$ may be prepared from a primary aniline (B), in a two step process, via an intermediate primary amide of formula (H), according to Scheme 12. Intermediate (H) may be prepared from a primary aniline (B) by reaction with a suitable anhydride. Typical reaction conditions comprise mixing together a primary aniline of formula (B) with the appropriate anhydride in a suitable solvent, such as dichloromethane, with a suitable base such as triethylamine, under nitrogen, for a suitable time, such as 20 hours, at a suitable temperature, such as ambient.

Secondary aniline (B), R=$R_6$ may then be prepared from intermediate (H), by reduction of the amide. Typical reaction conditions comprise mixing together an intermediate primary amide (H), with a suitable reducing agent, such as a solution of borane-tetrahydrofuran complex in tetrahydrofuran, in a suitable solvent such as tetrahydrofuran, under nitrogen. The mixture is then warmed to a suitable temperature, such as 60° C., and stirred for a suitable time, such as 2 hours.

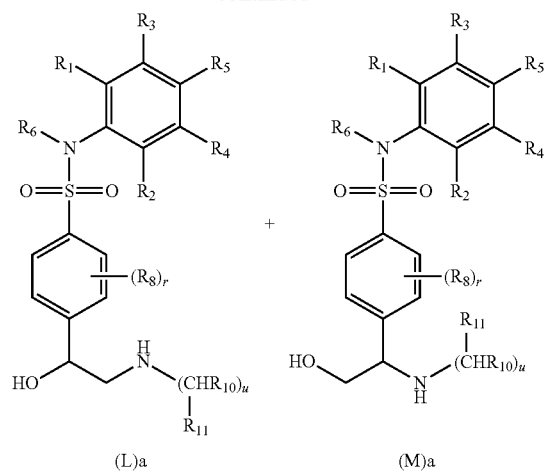

Secondary anilines of formula (B), R=$R_6$ may be prepared from primary anilines of formula (B), R=H, by reaction with an appropriate dialkylamine according to Scheme 13. Typical reaction conditions comprise mixing together a primary aniline (B), R=H, with the appropriate dialkylamine, a suitable base such as potassium iodide and a suitable catalyst such as pentamethylcyclopentadienyliridium(III) chloride in a suitable solvent such as xylene. The mixture is then heated in a sealed vessel to a suitable temperature, for example 190° C., by microwaves, for a suitable time, such as 2 hours.

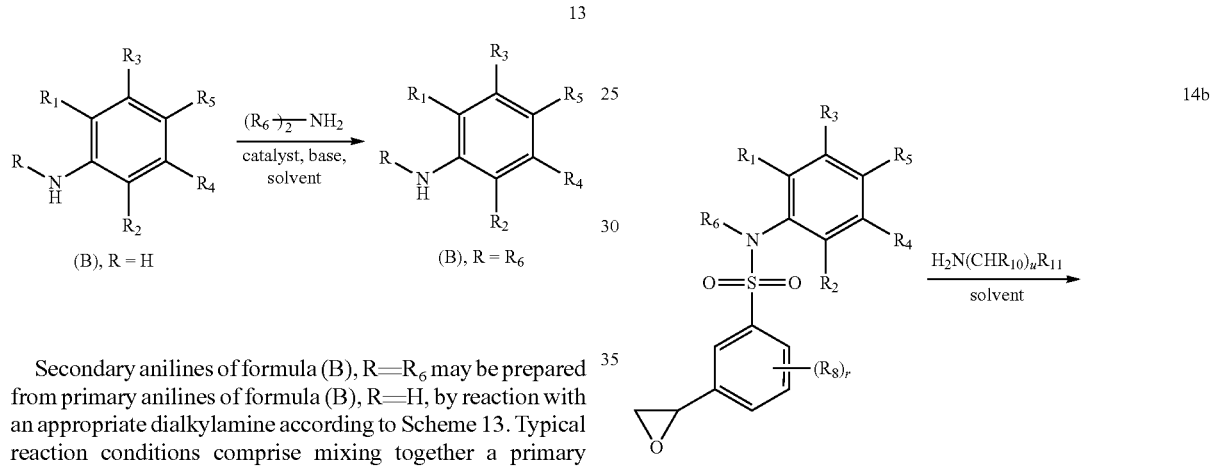

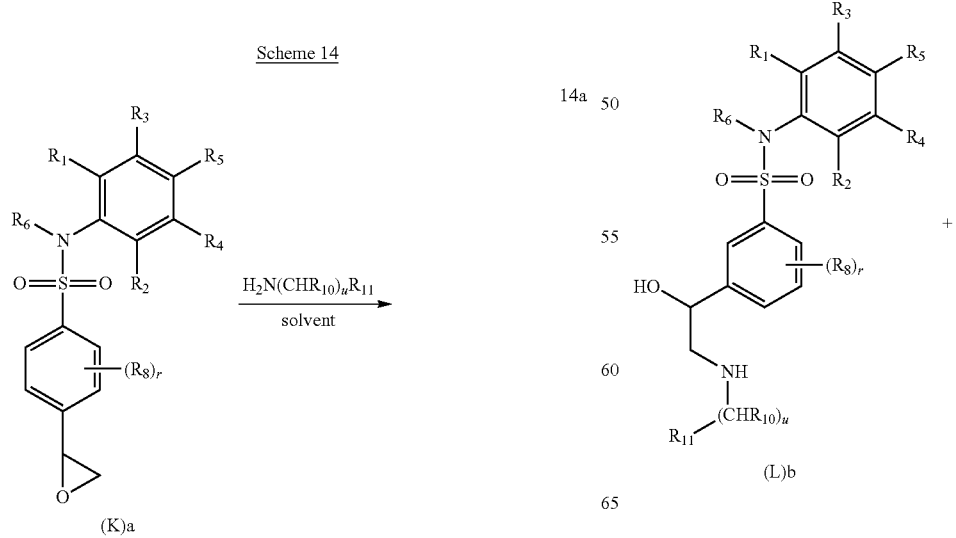

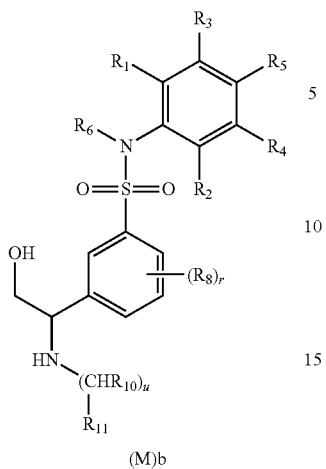

(M)b

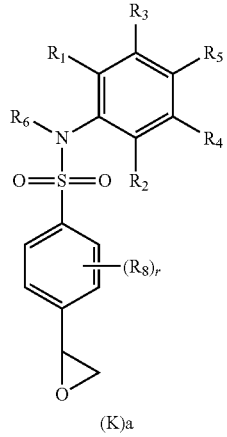

(K)a

Y = suitable cross-coupling group, eg. halogen, OTf

Compounds of formula (L)a/(M)a and (L)b/(M)b may be prepared from epoxide-containing intermediate compounds of formula (K)a and (K)b respectively, by reaction with an appropriate amine, according to Scheme 14a and 14b. Typical reaction conditions comprise mixing together epoxide-containing intermediate compound (K)a or (K)b with an appropriate amine, in a suitable solvent, such as ethanol, with a suitable base, such as triethylamine, at a suitable temperature, such as 50° C., for a suitable time, such as overnight. The ratio of products (L) to (M) may vary with selection of amine, and where a mixture of products results, separation may be achieved using a suitable purification system, such as preparative HPLC.

Scheme 15

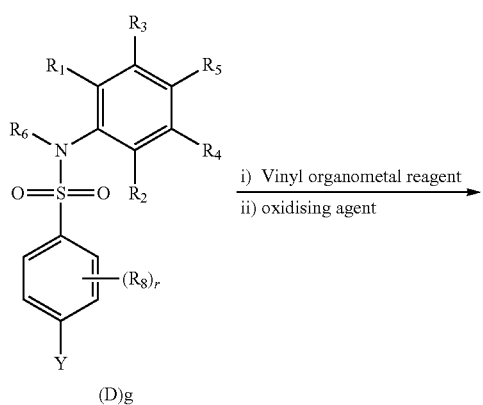

(D)g

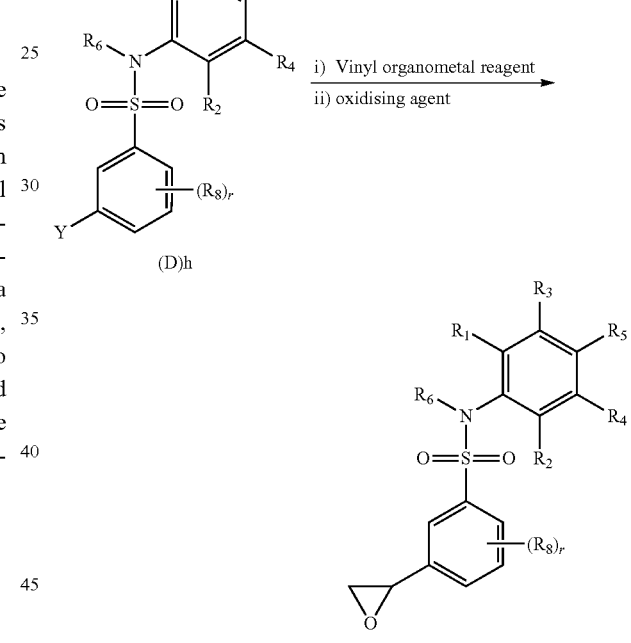

(D)h (K)b

Y = suitable cross-coupling group, eg. halogen, OTf

Epoxide-containing intermediate compounds of formula (K)a and (K)b, may be prepared from intermediate compounds of formula (D)g and (D)h respectively, by reaction with a vinyl organometal reagent, then oxidation of the vinyl group, according to Scheme 15. Typical reaction conditions for step (i) comprise mixing together intermediate compound (D)g or (D)h with a suitable vinyl organometal reagent, such as potassium trifluoro(vinyl)borate, an appropriate base such as cesium carbonate and a suitable catalyst such as palladium (II)chloride with a suitable ligand, such as triphenylphosphine. A suitable solvent, such as tetrahydrofuran/water mixture is then added and the reaction heated in a sealed vessel to a suitable temperature, for example 140° C., by microwaves, for a suitable time, such as 1 hour.

The resulting vinyl intermediate can then be oxidised to the epoxide-containing intermediate (K)a or (K)b by treating with a suitable oxidising agent, such as m-chloroperbenzoic acid in an appropriate solvent such as dichloromethane, for a suitable time, such as 16 hours, at a suitable temperature, such as 0° C. to ambient.

Example RORγ Modulators

The present invention is further illustrated by the following non-limiting examples of RORγ modulators, which have been prepared by a number of different methods.

Preparation of Products P1a to P21

The secondary anilines (P1a to P21—see Table 1) were prepared by one of six different routes (R1 to R6 below). The particular route used for the preparation of each secondary aniline product is outlined in Table 1

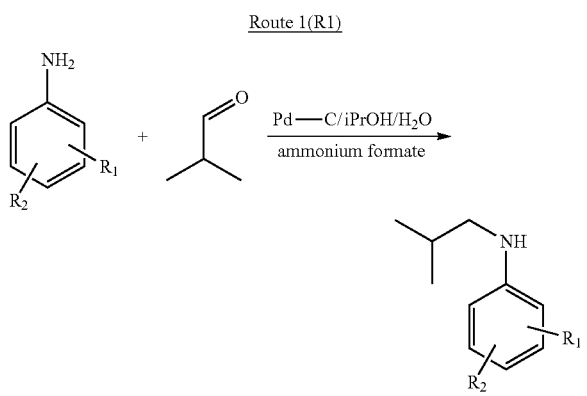

Generic Route

An aqueous solution of ammonium formate (5 equivalents, 0.2 mL/mmol) was diluted with isopropanol (1.6 mL) and added to palladium on carbon 10% wet (1 equivalent) under nitrogen. A solution of an aniline (1 equivalent, see Table 1 for specific aniline used) and isobutyraldehyde (1.1 equivalents) in isopropanol (0.3 mL/mmol) was added to the suspension and the mixture was stirred for 1 h. The mixture was filtered through celite, the celite cake washed with isopropanol. The combined liquid phases were concentrated in vacuo. The residue was purified using a pre-conditioned aminopropyl solid phase extraction cartridge (NH$_2$ SPE) (20 g) using methanol as an eluent. The methanolic organic phase was concentrated in vacuo to give a second residue which was further purified on a Biotage Flashmaster II using silica (Si) 10 g/mmol using a 0-100% dichloromethane-cyclohexane gradient. The fractions containing the expected product were combined and concentrated in vacuo to give the desired product.

Specific Example of Route 1 (R1)

Preparation of (2,4-dimethylphenyl)(2-methylpropyl)amine

An aqueous solution of ammonium formate (3.15 g, 50.0 mmol, 10 mL) was diluted with isopropanol (80 mL) and added to palladium on carbon 10% wet (1.064 g, 10.00 mmol) under nitrogen. A solution of 2,4-dimethylaniline (1.212 g, 10 mmol) and isobutyraldehyde (1.004 mL, 11.00 mmol) in isopropanol (3 mL) was added and the mixture was stirred for 1 h. The mixture was filtered through celite, the celite cake washed with isopropanol and combined liquid phases concentrated in vacuo. The residue (1.8 g) was purified using a pre-conditioned aminopropyl solid phase extraction cartridge (NH$_2$ SPE) (20 g) using methanol as an eluent. The methanolic organic phase was concentrated under vacuo to give a second residue which was further purified on a Biotage Flashmaster II using silica (Si) 10 g/mmol using a 0-100% dichloromethane-cyclohexane gradient over 40 mins. The fractions containing the expected product were combined and concentrated in vacuo to give the desired product 1.5 g as a yellow oil.

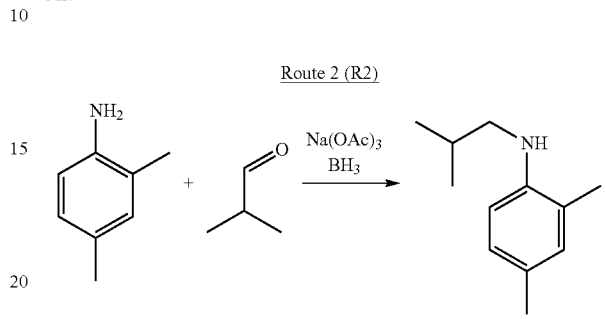

Specific Example of Route 2 (R2)

Preparation of (2,4-dimethylphenyl)(2-methylpropyl)amine

Isobutyraldehyde (5 mL, 55.1 mmol) was added to (2,4-dimethylphenyl)amine (7.01 g, 57.8 mmol) in Tetrahydrofuran (50 mL) to give a brown solution. The solution was stirred for 20 mins at room temperature before sodium triacetoxy borohydride (16.34 g, 77 mmol) was added. The reaction mixture was stirred at room temperature for 18 hours and the reaction was analysed by LCMS to confirm conversion to the desired product. The solution was diluted with ethyl acetate (100 mL) and the organic phase washed with water (100 mL). The organic phase was separated from the aqueous phase using a separating funnel. The organic phase was concentrated in vacuo to give the product as a brown oil.

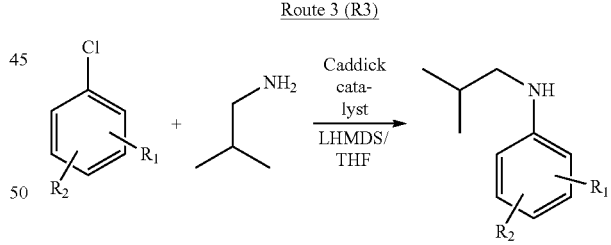

Generic Route

A mixture of an aryl chloride (1 equivalent, see Table 1 for specific aryl chloride used), isobutylamine (2 equivalents), and {1,3-bis[2,6-bis(1-methylethyl)phenyl]-2-imidazolidinyl}(chloro)(2-methyl-2-propen-1-yl)palladium 'Caddick catalyst' (prepared according to reference: Org. Biomol. Chem., 2008, 6, 2820-2825) (0.02 equivalents) was treated with lithium hexamethyl disilizide in tetrahydrofuran (1M in THF) (1.25 equivalents, 1.25 mL/mmol) under nitrogen. The reaction mixture was heated to 70° C. for 45 min in a septum-sealed vessel. The cooled mixture was concentrated in vacuo and the residue was partitioned between a solution of citric acid in water (4 mL/mmol) and tert butyl methyl ether (2×4 mL/mmol). The organic phase was treated with dried MgSO$_4$, the solid removed by filtration and the organic phase was concentrated in vacuo to give the product.

Specific Example of Route 3 (R3)

Preparation of (2,4-dimethylphenyl)(2-methylpropyl)amine

A mixture of 1-chloro-2,4-dimethylbenzene (1687 mg, 12 mmol), isobutylamine (1755 mg, 24.00 mmol), and Caddick catalyst (140 mg, 0.238 mmol) was treated with lithium hexamethyl disilizide in tetrahydrofuran (1M LHMDS in THF, 15 mL, 15.00 mmol) under nitrogen. The reaction mixture was heated to 70° C. for 45 min in a septum-sealed vessel. The cooled mixture was concentrated in vacuo and the residue was partitioned between aqueous citric acid (50 mL) and tert butyl methyl ether (TBME) (2×50 mL). The organic phase was treated with dried $MgSO_4$, the solid removed by filtration and the organic phase was concentrated in vacuo to give (2,4-dimethylphenyl)(2-methylpropyl)amine (2.05 g, 11.56 mmol, 96% yield) as an orange oil.

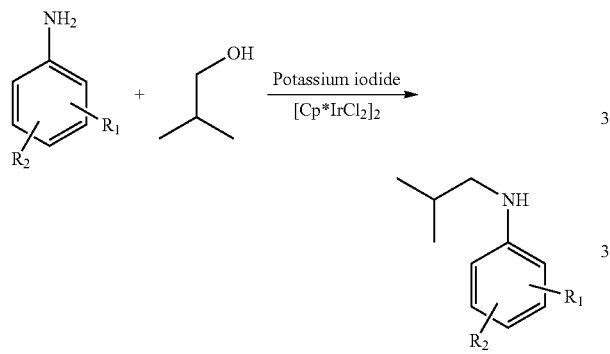

Generic Route 2-methyl-1-propanol (2 equivalents), an aniline (1 equivalent, see Table 1 for specific aniline used), potassium iodide (2 equivalents) and pentamethylcyclopentadienyliridium (III) chloride (obtainable from, for example, Sigma Aldrich), [Cp*IrCl$_2$]$_2$ (0.01 equivalents) were dissolved in water (0.6 mL/mmol). The resulting mixture was irradiated under microwaves (CEM microwave) at 170° C. for 1 hour. To the reaction mixture was added dichloromethane (1.5 mL/mmol) and the crude material organic was purified by mass directed autoprep using a formic acid modifier. Relevant fractions were combined and concentrated in vacuo to give the product.

Specific Example of Route 4 (R4)

Preparation of 2-methyl-N-(2-methylpropyl)-5-trifluoromethyl)aniline 2-methyl-1-propanol (0.556 mL, 6.00 mmol), 2-methyl-5-(trifluoromethyl)aniline (525 mg, 3 mmol), potassium iodide (996 mg, 6.00 mmol) and [Cp*IrCl$_2$]$_2$ (33.1 mg, 0.030 mmol) were dissolved in water (2 mL). The resulting mixture was irradiated under microwaves (CEM microwave) at 170° C. for 1 hour. To the reaction mixture was added dichloromethane (5 mL) and the crude material was purified by mass directed autoprep (250 mg scale ×3, Method C, formic acid modifier). Relevant fractions were combined and evaporated to give 2-methyl-N-(2-methylpropyl)-5-(trifluoromethyl)aniline (260 mg, 1.102 mmol, 36.7% yield) as a dark yellow oil.

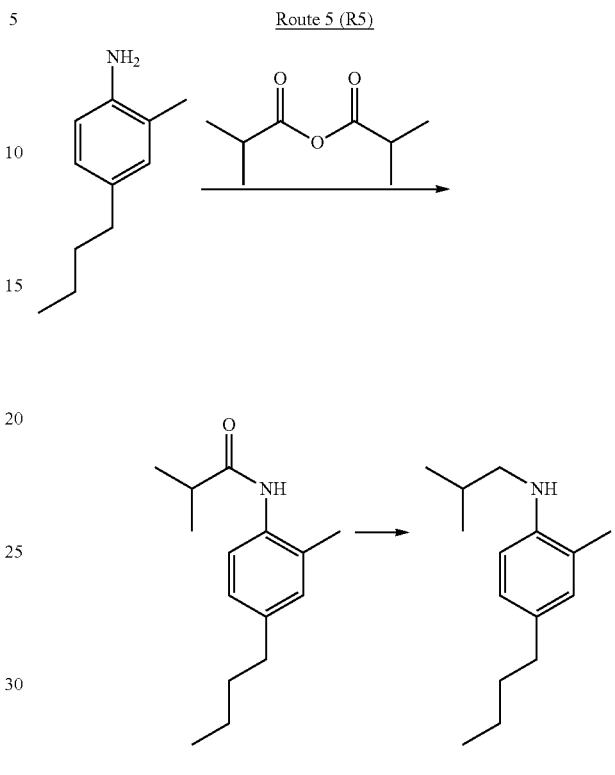

Specific Example of Route 5 (R5)

Preparation of 4-butyl-N-(2-methylpropyl)aniline

Isobutyric anhydride (2.034 mL, 12.25 mmol) was added dropwise to a stirred solution of 4-butyl-2-methylaniline (2 g, 12.25 mmol) and triethylamine (3.41 mL, 24.50 mmol) in dichloromethane (DCM) (20 mL) under nitrogen. The solution was stirred for 20 hours and then treated with 2M HCl (75 mL) and stirred for 5 minutes. The reaction mixture was extracted with DCM and the combined organic layers were dried over magnesium sulfate. The magnesium sulfate was filtered and the DCM phase concentrated in vacuo to gave N-(4-butyl-2-methylphenyl)-2-methylpropanamide (2.402 g, 10.29 mmol, 84% yield). A stirred solution of N-(4-butyl-2-methylphenyl)-2-methylpropanamide (2.402 g, 10.29 mmol) in tetrahydrofuran (30 mL) under nitrogen was treated dropwise with 1M borane in tetrahydrofuran (BH$_3$ in THF, 30.9 mL, 30.9 mmol; obtainable from, for example, Aldrich). The solution was heated at 60° C. for 2 hours before being quenched with 2M HCl (18 mL) and stirred for a further 15 minutes. It was then basified with aqueous Na$_2$CO$_3$ and extracted with DCM (2×150 mL). The combined organic phases were then dried over magnesium sulfate and concentrated in vacuo. The sample was loaded in dichloromethane and purified on Biotage Flashmaster II on silica (Si) 100 g using a 0-100% dichloromethane-cyclohexane over 60 mins. The appropriate fractions were combined and evaporated in vacuo to give 1.66 g of the title compound as a colourless liquid.

Route 6 (R6)

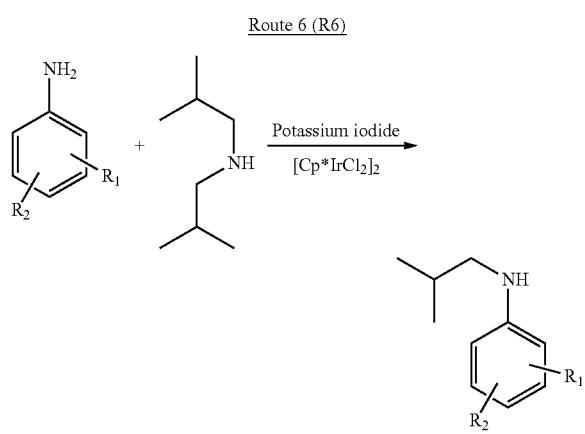

Generic Route

Pentamethylcyclopentadienylindium(III) chloride, [Cp*IrCl₂]₂ (0.01 equivalents), an aniline (1 equivalent, see Table 1 for specific aniline used), potassium iodide (2 equivalents) and diisobutylamine (3 equivalents) were dissolved in xylene (1 mL/mmol). The mixture was irradiated under microwaves (CEM microwave) for 2 hours at 190° C. To the mixture was added dichloromethane (1.5 mL/mmol) and water (1.5 mL/mmol). The organic fraction were separated and concentrated in vacuo. The crude material was purified on a Biotage Flashmaster II using silica (7 g/mmol, eluting with 0-100% DCM in cyclohexane). The relevant fractions were combined and concentrated to give the desired product.

Specific Example of Route 6 (R6)

Preparation of 4-(1-methylethyl)-N-(2-methylpropyl)aniline

[Cp*IrCl₂]₂ (33.1 mg, 0.030 mmol), 4-isopropylaniline (406 mg, 3 mmol), potassium iodide (996 mg, 6.00 mmol) and diisobutylamine (1.572 mL, 9.00 mmol) were dissolved in xylene (3 mL). The mixture was irradiated under microwaves (CEM microwave) for 2 hours at 190° C. To the mixture was added Dichloromethane (DCM) (1.5 mL/mmol) and water (1.5 mL/mmol). The organic fraction were separated and concentrated in vacuo. The crude material was purified by silica chromatography (20 g, eluting with 0-100% DCM in cyclohexane). The relevant fractions were combined and concentrated to leave the title compound (201 mg, 1.040 mmol, 34.7% yield) as a yellow oil.

TABLE 1

Preparation Details for Products P1a to P21 by Routes 1 to 6

| Product ID | Route | SM1 ID | Source | SM2 ID | Source | Scale (mmol) | Yield (%) | Work-up | Purification | RT | Base ion (M + 1) |
|---|---|---|---|---|---|---|---|---|---|---|---|
| P1a | R1 | A1 | Aldrich | B1 | Aldrich | 10 | 88 | S | D2 | 1.04 | 178 |
| P1b | R2 | A1 | Aldrich | B1 | Aldrich | 55.1 | 100 | A | None | 1.34 | 178 |
| P1c | R3 | A2 | Avocado Research Chemicals | B2 | Aldrich | 12 | 96 | A | None | 1.03 | 178 |
| P1d | R4 | A1 | Aldrich | B3 | Aldrich | 16.92 | 63 | A | D3 | 1.02 | 178 |
| P2a | R1 | A3 | ABCR Gelest (UK) Ltd | B1 | Aldrich | 4 | 57 | A | D1 | 1.49 | 220 |
| P2b | R4 | A3 | ABCR Gelest (UK) Ltd | B3 | Aldrich | 6 | 85 | A | D3 | 1.5 | 220 |
| P2c | R5 | A3 | ABCR Gelest (UK) Ltd | B4 | Aldrich | 2.45 | 47 | A | D2 | 3.8 | 220 |
| P3 | R4 | A4 | Aldrich | B3 | Aldrich | 6 | 62 | A | D2 | 1.18 | 182 |
| P4 | R4 | A5 | Aldrich | B3 | Aldrich | 6 | 70 | A | D2 | 1.25 | 184 |
| P5 | R4 | A6 | Apollo Scientific Ltd | B3 | Aldrich | 3 | 49 | A | D2 | 1.3 | 182 |
| P6 | R4 | A7 | Aldrich | B3 | Aldrich | 3 | 53 | A | D2 | 1.27 | 186 |
| P7 | R6 | A8 | Aldrich | B5 | Sigma Aldrich | 6 | 45 | A | D2 | 1.26 | 206 |
| P8 | R6 | A9 | Aldrich | B5 | Sigma Aldrich | 6 | 34 | A | D2 | 1.1 | 192 |
| P9 | R6 | A10 | Aldrich | B5 | Sigma Aldrich | 6 | 34 | A | D1 | 1.31 | 218 |
| P10 | R6 | A11 | Aldrich | B5 | Sigma Aldrich | 6 | 26 | A | N3 | 1.13 | 192 |
| P11 | R4 | A12 | Avocado Research Chemicals | B3 | Aldrich | 3 | 37 | A | F | 1.42 | 232 |
| P12 | R4 | A13 | Aldrich | B3 | Aldrich | 3 | 80 | A | D2 | 0.98 | 164 |
| P13 | R4 | A14 | Fluorochem | B3 | Aldrich | 3 | 10 | A | D5 | 1.37 | 202 |
| P14 | R4 | A15 | Avocado Research Chemicals | B3 | Aldrich | 3 | 27 | A | D2 | 1.35 | 202 |
| P15 | R4 | A16 | Acros Organics | B3 | Aldrich | 6 | 46 | A | D3 | 1.02 | 180 |
| P16 | R4 | A17 | Aldrich | B3 | Aldrich | 3 | 74 | A | D3 | 1.12 | 178 |
| P17 | R4 | A1 | Aldrich | B3 | Aldrich | 3 | 56 | A | D3 | 1.24 | 178 |
| P18 | R4 | A18 | Aldrich | B3 | Aldrich | 3 | 85 | A | None | 0.77 | 164 |
| P19 | R4 | A1 | Aldrich | B6 | Sigma Aldrich | 12.38 | 33 | A | N2 | 1.32 | 176 |

TABLE 1-continued

Preparation Details for Products P1a to P21 by Routes 1 to 6

| Product ID | Route | SM1 ID | Source | SM2 ID | Source | Scale (mmol) | Yield (%) | Work-up | Purification | RT | Base ion (M + 1) |
|---|---|---|---|---|---|---|---|---|---|---|---|
| P20 | R3 | A19 | Aldrich | B2 | Aldrich | 2 | 34 | A | None | 1.03 | 180 |
| P21 | R4 | A20 | Refer to Additional Experimental Section | B3 | Aldrich | 0.802 | 63 | A | D2 | 1.07 | 322 |

Preparation of Products P22 to P82

The secondary and tertiary sulfonamide products P21 to P82 (see Table 2) were prepared by either Route 7 or Route 8 described below. The particular route used for the preparation of each secondary of tertiary sulfonamide product is outlined in Table 2.

Route 7 (R7)

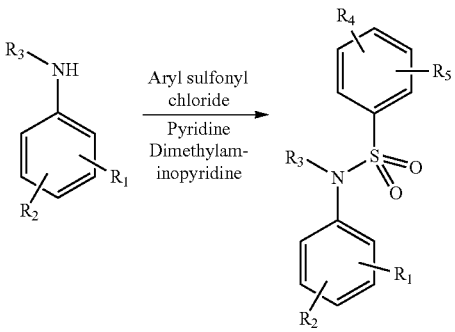

$R_3$ = alkyl or H

Generic Route

To a solution of an aniline (1 equivalent, See Table 2 for specific aniline used) in pyridine (4 mL/mmol) was added a sulfonyl chloride (1 equivalent, See Table 2 for specific sulfonyl chloride used) in one charge at room temperature. In some cases 4-dimethylaminopyridine (0.02 equivalents) was also added to reaction mixture (see Table 2 for further details). The reaction mixture was left to stand at 20° C. for 16 hr. In some cases, the reaction solution was heated (80 or 95° C.) for 1 h before being left at room temperature overnight. The solvent was evaporated in vacuo (Biotage V10 evaporator) to give a crude material. The crude material was treated in one of the following ways: 1. Purification on SPE cartridges; 2. aqueous work up, evaporation of the organic phase followed by purification by mass directed autoprep.

Specific Example of Route 7 (R7)

Preparation of N-(4-chlorophenyl)-4-((3,5-dimethylisoxazol-4-yl)methoxy)-N-isobutylbenzenesulfonamide N-(4-chlorophenyl)-4-((3,5-dimethylisoxazol-4-yl)methoxy)-N-isobutylbenzenesulfonamide was prepared in an array format. 4-chloro-N-isobutylaniline (1.493 mg, 0.099 mmol) was pre-weighed into a 2 mL vial, and 4-((3,5-dimethylisoxazol-4-yl)methoxy)benzene-1-sulfonyl chloride (30 mg, 0.099 mmol) then added, followed by 4-DMAP (approx 2 mg). Pyridine (0.3 mL) was added last. The reaction solution was capped and stood at RT for 3 days. After this time the reaction was not complete and the reaction were warmed to 80° C. for 2 hours. The pyridine was removed to almost dryness. DMSO (1 mL) was added to the residues which were then purified by mass directed autoPrep on a Sunfire C18 column using Acetonitrile Water with a Formic acid modifier. The solvent was dried under a stream of nitrogen in the Radleys blowdown apparatus to give the required products.

Route 8 (R8)

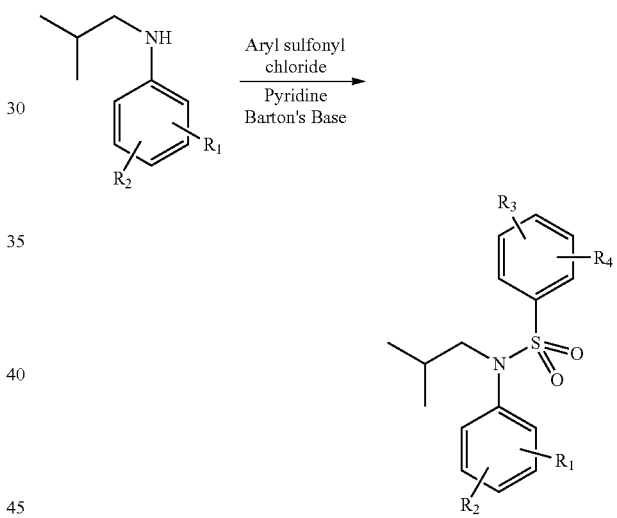

Generic Route

To a solution of an amine (1 equivalent, see Table 2 for specific amine used) and sulfonyl chloride (1.1 equivalents, see Table 2 for specific sulfonyl chloride used) in pyridine (2 mL/mmol) was added neat Barton's base (2-(tert-butyl)-1,1,3,3-tetramethylguanidine) (1 equivalent). The reaction vessel was sealed and heated in Emrys Optimiser using initial high absorbance to 100° C. for 30 min. After cooling the reaction was analysed and product presence confirmed. The solvent was evaporated in vacuo using the Vaportec V10 to give the crude product. The sample was loaded in methanol and purified by SPE on aminopropyl ($NH_2$) 10 g/mmol using methanol. The appropriate fractions were concentrated and further purified on SPE on sulfonic acid (SCX) 4 g/mmol using methanol. The appropriate fractions were combined and dried under a stream of nitrogen in the Radley's blowdown apparatus to give the crude product. The samples were dissolved in 1:1 MeOH:DMSO 1 mL and purified by mass directed autoPrep on Sunfire C18 column using Acetonitrile Water with a Formic acid modifier. The fractions containing the product were combined and solvent removed under a stream of nitrogen in the Radleys blowdown apparatus to give the required products.

Specific Example of Route 8 (R8)

Preparation of N-[4-(cyclopropylmethyl)-2,6-dimethylphenyl]-4-{[(3,5-dimethyl-4-isoxazolyl)methyl]oxy}benzenesulfonamide To a solution of [4-(cyclopropylmethyl)-2,6-dimethylphenyl]amine hydrochloride (100 mg, 0.472 mmol) and 4-{[(3,5-dimethyl-4-isoxazolyl)methyl]oxy}benzenesulfonyl chloride (157 mg, 0.520 mmol) in Pyridine (1 mL) was added neat Barton's base (2-(tert-butyl)-1,1,3,3-tetramethylguanidine) (0.095 mL, 0.472 mmol). The reaction vessel was sealed and heated in Emrys Optimiser using initial high absorbance to 100° C. for 30 min. After cooling the reaction was analysed and product presence confirmed. The solvent was evaporated in vacuo using the Vaportec V10 to give the crude product. The sample was loaded in methanol and purified by SPE on aminopropyl ($NH_2$) 5 g using methanol. The appropriate fractions were concentrated and the crude material further purified by SPE on sulfonic acid (SCX) 2 g using methanol. The appropriate fractions were combined and dried under a stream of nitrogen in the Radleys blowdown apparatus to give the crude product. The samples were dissolved in 1:1 MeOH:DMSO 1 mL and purified by mass directed autoPrep on Sunfire C18 column using Acetonitrile Water with a Formic acid modifier. The solvent was dried under a stream of nitrogen in the Radleys blowdown apparatus to give the required products (7.4 mg, 0.017 mmol, 3.56% yield)

TABLE 2

Preparation of Products P22 to P82 by Route 7 or 8

| Product ID | Route | SM1 ID | Source | SM2 ID | Source | Scale (mmol) | DMAP | °C. | Yield (%) | Work up | Purification | RT | Base ion (M + 1) |
|---|---|---|---|---|---|---|---|---|---|---|---|---|---|
| P22 | R7 | P2c | See Table 1 | B7 | Apollo Scientific Ltd | 0.1 | yes | 95 | 3 | E | F | 1.25 | 453 |
| P23 | R7 | P2c | See Table 1 | B8 | Manchester Organics | 0.1 | yes | 95 | 15 | E | F | 1.55 | 485 |
| P24 | R7 | P1a | See Table 1 | B8 | ACB Blocks Ltd | 0.2 | no | 20 | 19 | E | F | 1.4 | 443 |
| P25 | R7 | P3 | See Table 1 | B8 | Manchester Organics | 0.3 | no | 20 | 16 | S | F | 1.36 | 447 |
| P26 | R7 | P6 | See Table 1 | B8 | ACB Blocks Ltd | 0.27 | no | 20 | 18 | S | F | 1.3 | 451 |
| P27 | R7 | P7 | See Table 1 | B8 | Manchester Organics | 0.24 | no | 20 | 13 | S | N1 | 1.51 | 471 |
| P28 | R7 | P8 | See Table 1 | B8 | Manchester Organics | 0.26 | no | 20 | 23 | S | F & ED1 | 1.44 | 457 |
| P29 | R7 | P5 | See Table 1 | B8 | ACB Blocks Ltd | 0.276 | no | 20 | 5 | S | F | 1.34 | 447 |
| P30 | R7 | P4 | See Table 1 | B8 | Manchester Organics | 0.1 | yes | 80 | 13 | E | F | 1.45 | 449 |
| P31 | R7 | P10 | See Table 1 | B8 | Manchester Organics | 0.1 | yes | 80 | 47 | E | F | 1.53 | 457 |
| P32 | R7 | P9 | See Table 1 | B8 | Manchester Organics | 0.1 | yes | 80 | 43 | E | F | 1.43 | 483 |
| P33 | R7 | P11 | See Table 1 | B8 | Manchester Organics | 0.1 | yes | 80 | 3 | E | F | 1.47 | 497 |
| P34 | R7 | A21 | Otava Building Blocks | B8 | Manchester Organics | 0.099 | yes | 20 | 26 | E | F | 1.27 | 415 |
| P35 | R7 | A22 | UkrOrgSynthesis Ltd | B8 | Manchester Organics | 0.1 | yes | 20 | 15 | E | A | 1.3 | 429 |
| P36 | R7 | P12 | See Table 1 | B8 | ACB Blocks Ltd | 0.184 | no | 20 | 66 | S | F | 1.36 | 429 |
| P37 | R7 | P17 | See Table 1 | B8 | ACB Blocks Ltd | 0.169 | no | 20 | 48 | E | F | 1.41 | 443 |
| P38 | R7 | P16 | See Table 1 | B8 | ACB Blocks Ltd | 0.186 | no | 20 | 61 | E | F | 1.41 | 443 |
| P39 | R7 | P14 | See Table 1 | B8 | ACB Blocks Ltd | 0.149 | no | 20 | 27 | E | F | 1.33 | 467 |
| P40 | R8 | P13 | See Table 1 | B8 | ACB Blocks Ltd | 0.297 | no | 150 | 4 | E | F | 1.32 | 467 |
| P41 | R7 | P15 | See Table 1 | B9 | Enamine Ltd | 1 | no | 20 | 50 | A & S | none | 1.41 | 426 |
| P42 | R7 | P18 | See Table 1 | B8 | Manchester Organics | 0.306 | no | 20 | 52 | S | F | 1.35 | 429 |
| P43 | R7 | P19 | See Table 1 | B8 | Manchester Organics | 0.1 | no | 20 | 40 | E | F | 1.36 | 441 |
| P44 | R7 | P20 | See Table 1 | B8 | Manchester Organics | 0.575 | no | 20 | 64 | A | none | 1.16 | 445 |
| P45 | R7 | A23 | ABCR | B8 | Manchester Organics | 0.370 | no | 20 | 50 | S | F | 3.22 | 401 |
| P46 | R7 | P1c | See Table 1 | B9 | Enamine Ltd | 5.6 | no | 20 | 41 | A | R | 1.54 | 424 |

TABLE 2-continued

Preparation of Products P22 to P82 by Route 7 or 8

| Product ID | Route | SM1 ID | Source | SM2 ID | Source | Scale (mmol) | DMAP | °C. | Yield (%) | Work up | Purification | RT | Base ion (M + 1) |
|---|---|---|---|---|---|---|---|---|---|---|---|---|---|
| P47 | R7 | P1d | See Table 1 | B11 | Aldrich | 5.64 | no | 20 | 92 | A | none | 1.42 | 336 |
| P48 | R7 | A24 | ABCR | B9 | Enamine Ltd | 1 | no | 20 | 54 | A | E3 | 1.23 | 375 |
| P49 | R7 | A25 | Aldrich | B8 | Manchester Organics | 0.3 | no | 20 | 51 | S | none | 1.04 | 395 |
| P50 | R7 | A26 | SigmaAldrich | B8 | Manchester Organics | 0.9 | no | 20 | 91 | S | none | 1.21 | 427 |
| P51 | R7 | A27 | Aldrich | B8 | Manchester Organics | 0.9 | no | 20 | 36 | S | none | 1.17 | 427 |
| P52 | R7 | A28 | Aldrich | B8 | Manchester Organics | 0.321 | no | 20 | 25 | S | none | 1.18 | 427 |
| P53 | R7 | A24 | ABCR | B8 | Manchester Organics | 0.194 | no | 20 | 81 | E | F | 1.09 | 395 |
| P54 | R7 | A29 | Aldrich | B8 | Manchester Organics | 0.3 | no | 20 | 98 | S | none | 1.12 | 387 |
| P55 | R7 | A30 | Apollo Scientific Ltd | B8 | Manchester Organics | 0.3 | no | 20 | 96 | S | none | 1.1 | 391 |
| P56 | R7 | A25 | Aldrich | B8 | Manchester Organics | 0.3 | no | 20 | 100 | S | none | 1.14 | 387 |
| P57 | R7 | A31 | Sigma Aldrich | B8 | Manchester Organics | 0.3 | no | 20 | 44 | S | none | 1.05 | 403 |
| P58 | R7 | A32 | Aldrich | B8 | Manchester Organics | 0.3 | no | 20 | 98 | S | none | 1.08 | 391 |
| P59 | R7 | A33 | Aldrich | B8 | Manchester Organics | 0.3 | no | 20 | 75 | S | none | 1.11 | 393 |
| P60 | R7 | P12 | See Table 1 | B9 | Enamine Ltd | 1 | no | 20 | 78 | A | none | 1.5 | 410 |
| P61 | R7 | P16 | See Table 1 | B9 | Enamine Ltd | 1 | no | 20 | 62 | A | none | 1.54 | 424 |
| P62 | R7 | P17 | See Table 1 | B9 | Enamine Ltd | 1 | no | 20 | 57 | A | none | 1.51 | 424 |
| P41 | R7 | P15 | See Table 1 | B9 | Enamine Ltd | 1 | no | 20 | 50 | A & S | none | 1.41 | 426 |
| P63 | R7 | A31 | Sigma Aldrich | B11 | Aldrich | 1 | no | 20 | 63 | S | none | 1.02 | 296 |
| P64 | R7 | A34 | Acros Organics | B11 | Aldrich | 1 | no | 20 | 91 | S | none | 1.1 | 280 |
| P65 | R7 | A30 | Apollo Scientific Ltd | B11 | Aldrich | 1 | no | 20 | 76 | S | none | 1.06 | 284 |
| P66 | R7 | A25 | Aldrich | B11 | Aldrich | 1 | no | 40 | 31 | E | E2 | 1.01 | 288 |
| P67 | R7 | A32 | Aldrich | B9 | Enamine Ltd | 1 | no | 40 | 71 | A | E3 | 1.23 | 372 |
| P68 | R7 | A15 | Avocado | B11 | Aldrich | 0.687 | no | 40 | 96 | A | none | 1.09 | 303 |
| P69 | R7 | A35 | TCI UK Ltd | B8 | Manchester Organics | 0.67 | no | 20 | 90 | S | none | 1.23 | 415 |
| P70 | R7 | P1d | See Table 1 | B12 | Alfa Aesar | 2.096 | no | 20 | 59 | A | E3 | 1.44 | 348 |
| P71 | R7 | P1d | See Table 1 | B13 | Apollo Scientific Ltd | 1.918 | no | 20 | 61 | A | D3 | 1.41 | 179 |
| P72 | R7 | A36 | Fluka | B8 | Manchester Organics | 0.467 | no | 20 | 42 | A | none | 1.07 | 373 |
| P73 | R7 | P1d | See Table 1 | B14 | Sigma Aldrich | 0.564 | no | 20 | 58 | A | E1 | 1.47 | 366 |
| P74 | R7 | A37 | Sigma Aldrich | B8 | Manchester Organics | 1.29 | no | 20 | 98 | A | none | 1.17 | 451 |
| P75 | R7 | P1d | See Table 1 | B15 | ChemCollect GmbH | 0.6 | no | 20 | 49 | E | F | 1.26 | 364 |
| P76 | R8 | A38 | WO 2009 045830 | B8 | Manchester Organics | 0.472 | no | 100 | 4 | S | T | 1.28 | 441 |
| P77 | R7 | P2a | See Table 1 | B16 | ABCR | 0.1 | yes | 95 | 38 | E | F | 1.52 | 352 |
| P78 | R7 | P1d | See Table 1 | B17 | Aldrich | 2.82 | no | 20 | 67 | S | none | 1.51 | 336 |
| P79 | R7 | P1d | See Table 1 | B18 | Apollo international | 2.8 | no | 20 | 98 | A | E3 | 1.56 | 340 |
| P80 | R7 | P21 | See Table 1 | B8 | Manchester Organics | 0.506 | no | 20 | 93 | A | none | 1.69 | 344 |
| P81 | R7 | P15 | See Table 1 | B8 | Manchester Organics | 0.167 | no | 20 | 70 | E | F | 1.28 | 338 |
| P82 | R7 | A39 | Fluorochem | B8 | Manchester Organics | 1 | no | 20 | 94 | A | none | 1.11 | 428 |

Preparation of Products P83 to P97

The tertiary sulfonamide products P83 to P97 were prepared by a number of routes as described below. The particular route used for the preparation of each tertiary sulfonamide product is outlined in Table 3.

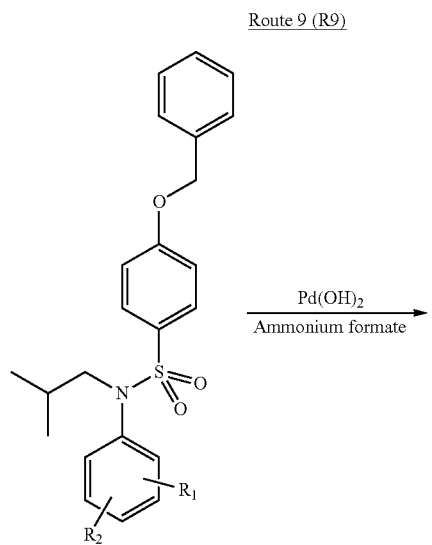

Route 9 (R9)

Generic Route

To a round bottomed flask was added a sulfonamide (1 equivalent, see Table 3 for specific sulfonamide used), ammonium formate (5 equivalents), palladium(II) hydroxide (20% on carbon) (0.1 equivalents) and ethanol (28 mL/mmol). The reaction mixture was stirred and left to reflux under nitrogen overnight at 90° C. An LCMS was taken, and showed full conversion into the product, and then reaction mixture was left to cool. To remove the palladium (II) hydroxide, the reaction mixture was then passed through a celite column (10 g/mmol). The residue remaining on the celite was thoroughly dampened with water, and then deactivated with a sodium metabisulfite solution. The crude mixture was concentrated in vacuo, diluted with ethyl acetate and washed with water, then brine. An LCMS confirmed the presence of the product in the organic phase, which was then dried down under a stream of nitrogen.

Specific Example of Route 9

N-(2,4-dimethylphenyl)-4-hydroxy-N-(2-methylpropyl)benzenesulfonamide

To a round bottomed flask was added a stirrer bar, N-(2,4-dimethylphenyl)-N-(2-methylpropyl)-4-[(phenylmethyl)oxy]benzenesulfonamide (974 mg, 2.300 mmol), ammonium formate (725 mg, 11.50 mmol), palladium(II) hydroxide (20% on carbon) (164 mg, 0.230 mmol) and Ethanol (65 mL). A reflux condenser was placed on the top of the flask and the reaction mixture was heated to 90° C. under reflux with stirring overnight. A product peak was observed by LCMS analysis, but only partial conversion had been seen overnight. White crystals thought to be ammonium formate were observed on the side of the reflux condenser and consequently a further 5 equivalents of ammonium formate (725 mg, 11.50 mmol) were added to the reaction mixture. The temperature of the heater was raised to 95° C. after which the reaction mixture had reached boiling point. After a further 30 minutes of heating, another LCMS sample was taken, showing no change in the ratio of starting material:product. The reaction mixture was cooled for 5 minutes before the addition of another measure of palladium(II) hydroxide (20% on carbon) (164 mg, 0.230 mmol). The reaction mixture was then reheated to 95° C. for another 30 minutes after which full conversion to the product was observed. The reaction mixture was filtered through a 10 g Celite cartridge before concentrating in vacuo to give 727 mg of crude product. The crude mixture was diluted with ethyl acetate and washed with water, then brine. The organic phase was then concentrated in vacuo to give 663 mg of the title compound.

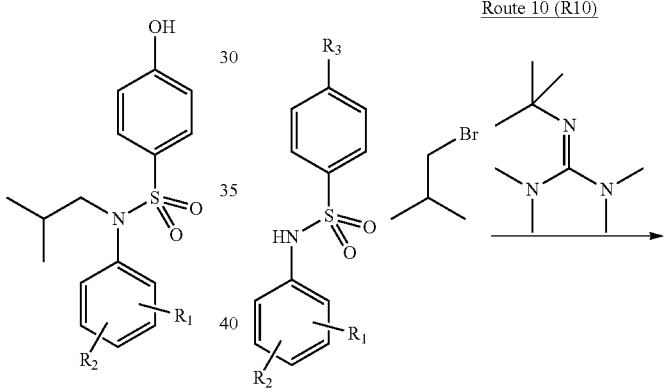

Route 10 (R10)

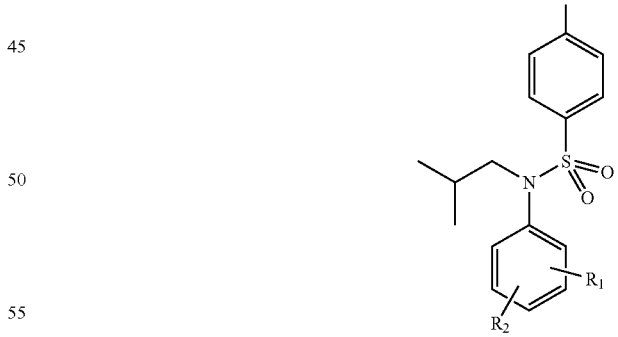

Generic Route

To a solution of a sulfonamide (1 equivalent, see Table 4 for specific sulfonamide used) in Acetonitrile (8 mL/mmol) was added neat Barton's base (2-(tert-butyl)-1,1,3,3-tetramethylguanidine)(1 equivalent). The reaction mixture was stirred at room temperature for 1 hour. 1-bromo-2-methylpropane (2 equivalents) was then added. The reaction vessel was sealed and heated in Biotage Initiator microwave using initial high absorbance power setting to 150° C. for 25 min. The solvent was dried under a stream of nitrogen in the Radleys blowdown apparatus. The sample was loaded in dichloromethane and purified on automated normal chromatograph on silica (Si) 80 g/mmol using a 0-50% ethyl acetate-cyclohexane. The appropriate fractions were combined and evaporated to give the required product.

Specific Example of Route 10 (R10)

4-fluoro-N-[2-methyl-5-(methyloxy)phenyl]-N-(2-methylpropyl)benzenesulfonamide

To a solution of 4-fluoro-N-[2-methyl-5-(methyloxy)phenyl]benzenesulfonamide (185.8 mg, 0.629 mmol) in Acetonitrile (5 mL) was added neat Barton's base (2-(tert-butyl)-1,1,3,3-tetramethylguanidine) (0.131 mL, 0.629 mmol). The reaction mixture was stirred at room temperature for 1 hour. 1-bromo-2-methylpropane (0.137 mL, 1.258 mmol) was then added. The reaction vessel was sealed and heated in Biotage Initiator microwave using initial high absorbance power setting to 150° C. for 25 min. The solvent was dried under a stream of nitrogen in the Radleys blowdown apparatus. The sample was loaded in dichloromethane and purified on automated normal chromatograph on silica (Si) 50 g using a 0-50% ethyl acetate-cyclohexane over 40 mins. The appropriate fractions were combined and dried under a stream of nitrogen in the Radleys blowdown apparatus to give the required product 171 mg as a white solid.

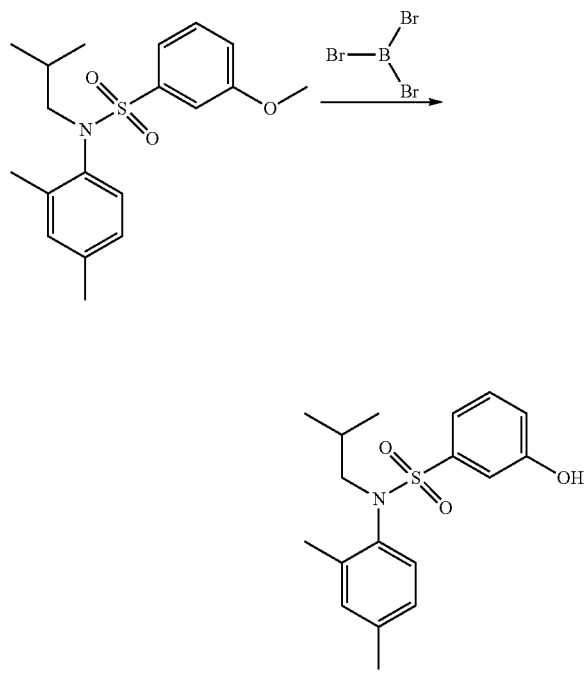

Specific Example of Route 11 (R11)

N-(2,4-dimethylphenyl)-N-isobutyl-3-methoxybenzenesulfonamide (431.4 mg, 1.242 mmol) was dissolved in dichloromethane (DCM) (10 mL) and cooled to −78° C. BBr₃ in DCM (1M) (6.21 mL, 6.21 mmol) was added dropwise and the reaction put under nitrogen. The reaction was allowed to reach room temperature and left to stir overnight. Water (20 mL) was added dropwise into the reaction mixture, until no more fumes were released. The crude product was then extracted to the organic phase of an aqueous work up between DCM (30 mL) and water (20 mL). The aqueous phase was washed twice with DCM (20 mL×2). The organic phase was then dried and concentrated in vacuo. The crude product was then dissolved in a minimum of DCM, and loaded onto a silica column before being purified by silica column chromatography (20 mins, 20 g, 0-25% EtOAc in cyclohexane). The relevant fractions were then combined and condensed, to give the product, N-(2,4-dimethylphenyl)-3-hydroxy-N-isobutylbenzenesulfonamide, 384.4 mg.

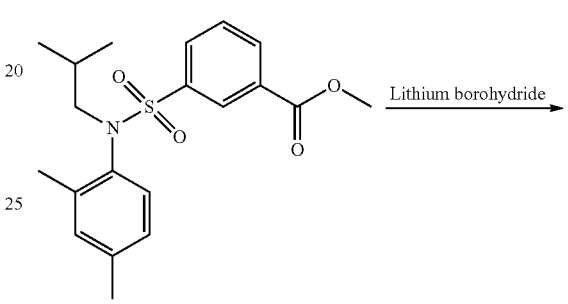

Specific Example of Route 12 (R12)

Methyl 3-(N-(2,4-dimethylphenyl)-N-isobutylsulfamoyl)benzoate (400 mg, 1.065 mmol) was dissolved in tetrahydrofuran (THF) (10 mL). To this solution was added lithium borohydride (2M in THF) (0.932 mL, 1.864 mmol). The reaction was left to stir overnight, at room temperature, overnight. The reaction was quenched by the addition of 5% citric acid (10 mL), and the reaction allowed to stir, under nitrogen for 1 hour. The reaction mixture was then diluted with ethyl acetate (25 mL), and the product extracted to the organic phase. The organic phase was dried by passing it through a hydrophobic frit, and then concentrated in vacuo to give the desired product, N-(2,4-dimethylphenyl)-3-(hydroxymethyl)-N-isobutylbenzenesulfonamide, 378.7 mg.

TABLE 3

Preparation of Products P83 to P97 by Routes 9 to 12

| Product ID | Route | SM1 ID | Source | SM2 ID | Source | Scale (mmol) | Yield (%) | Work-up | Purification | RT | Base ion (M + 1) |
|---|---|---|---|---|---|---|---|---|---|---|---|
| P83 | R9  | P46 | See Table 1 | N/A | N/A     | 2.3   | 86  | A | none | 1.3 | 334 |
| P84 | R9  | P60 | See Table 2 | N/A | N/A     | 0.779 | 92  | A | none | 1.2 | 320 |
| P85 | R9  | P61 | See Table 2 | N/A | N/A     | 0.619 | 79% | F | none | 1.2 | 334 |
| P86 | R9  | P62 | See Table 2 | N/A | N/A     | 0.567 | 90  | A | none | 1.2 | 334 |
| P87 | R9  | P41 | See Table 2 | N/A | N/A     | 0.504 | 79  | A | none | 1.1 | 336 |
| P88 | R10 | P63 | See Table 2 | B19 | Aldrich | 0.629 | 77  | E | E2   | 1.3 | 352 |
| P89 | R10 | P64 | See Table 2 | B19 | Aldrich | 0.909 | 73  | E | E2   | 1.4 | 336 |
| P90 | R10 | P65 | See Table 2 | B19 | Aldrich | 0.762 | 63  | E | E2   | 1.3 | 340 |
| P91 | R10 | P66 | See Table 2 | B19 | Aldrich | 0.313 | 45  | E | E2   | 1.3 | 344 |
| P92 | R9  | P93 | See Table 2 | N/A | N/A     | 0.327 | 85  | A | none | 1.2 | 338 |
| P93 | R10 | P67 | See Table 2 | B19 | Aldrich | 0.528 | 65  | A | E3   | 1.5 | 428 |
| P94 | R10 | P68 | See Table 2 | B19 | Aldrich | 0.731 | 57  | A | E3   | 1.4 | 360 |
| P95 | R11 | P70 | See Table 2 | N/A | N/A     | 1.242 | 93  | E | E3   | 1.3 | 334 |
| P96 | R12 | P71 | See Table 2 | N/A | N/A     | 1.065 | 102 | A | none | 1.2 | 348 |
| P97 | R10 | P82 | See Table 2 | B19 | Aldrich | 0.945 | 33  | A | F    | 1.4 | 501 |

Preparation of Products P98 to P149

The tertiary sulfonamide products P98 to P149 were prepared by a number of different routes as described below. The particular route used for the preparation of each tertiary sulfonamide product is outlined in Table 4.

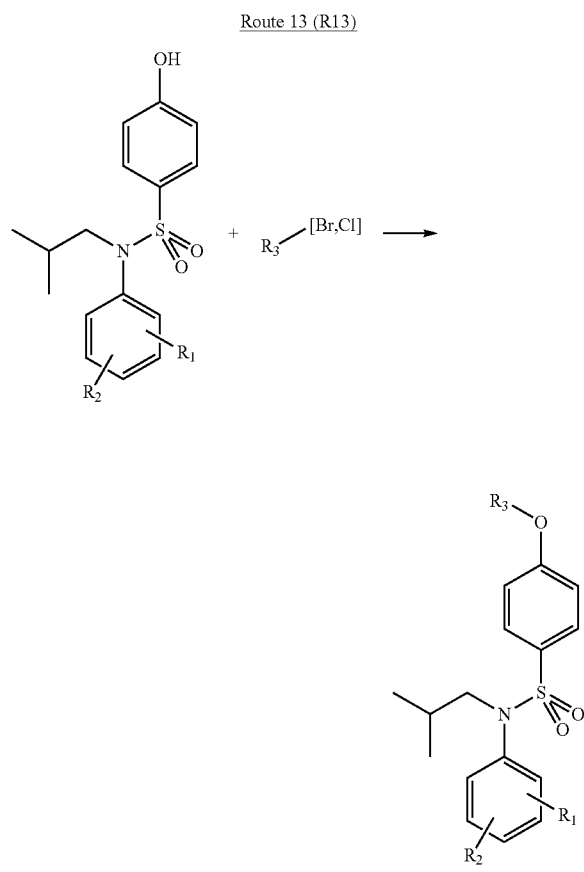

Route 13 (R13)

Generic Route

This route was performed in an array format. A mixture of a phenol (1 equivalent, see Table 4 for specific phenol used), and potassium fluoride, 40% by weight on alumina (40% KF.Al$_2$O$_3$ 3 equivalents) in acetonitrile (2 mL/mmol) was stirred for 5 mins, before addition of an alkylating reagent (see Table 4 for specific alkylating agent used for each reaction) (1 equivalent) in acetonitrile (2 mL/mmol). The reaction mixture was capped and stirred at RT for 18 hours. Additional 40% KF.Al$_2$O$_3$ (3 equivalents) and more alkylating reagent (1 equivalent) were added to the tube, which was capped and stirred for a further 18 hours. The sample was filtered through cotton wool, and DMSO added to bring the total volume to 1 mL. The solution was purified by CAS mass directed autoPrep on Sunfire C18 column using acetonitrile:water with a formic acid modifier. The solvent was dried under a stream of nitrogen in the Radleys blowdown apparatus to give the required product.

Specific Example of Route 13

Preparation of N-(2,4-dimethylphenyl)-N-isobutyl-4-(pyridine-4-ylmethoxy)benzenesulfonamide A mixture of N-(2,4-dimethylphenyl)-4-hydroxy-N-isobutylbenzenesulfonamide (33 mg, 0.099 mmol), and potassium fluoride, 40% by weight on alumina (40% KF.Al$_2$O$_3$ 43.1 mg, 0.297 mmol) in acetonitrile (0.2 mL) were stirred for 5 mins, before addition of 4-(bromomethyl)pyridine (0.099 mmol) in acetonitrile (0.2 mL). The reaction mixture was capped and stirred at RT for 18 hours. Additional 40% KF.Al$_2$O$_3$ (43 mg) and more alkylating reagent (0.1 mmol) were added to the tube, which was capped and stirred for a further 18 hours. The reaction had additional potassium fluoride, 40% by weight on alumina (43 mg) and alkylating reagent (0.1 mmol), and then recapped and stirred for 2 days. The sample was filtered through cotton wool, and DMSO added to bring the total volume to 1 mL. The solutions were purified by mass directed autoprep on Sunfire C18 column using acetonitrile water with a formic acid modifier. The solvent was dried under a stream of nitrogen in the Radleys blowdown apparatus to give the required product.

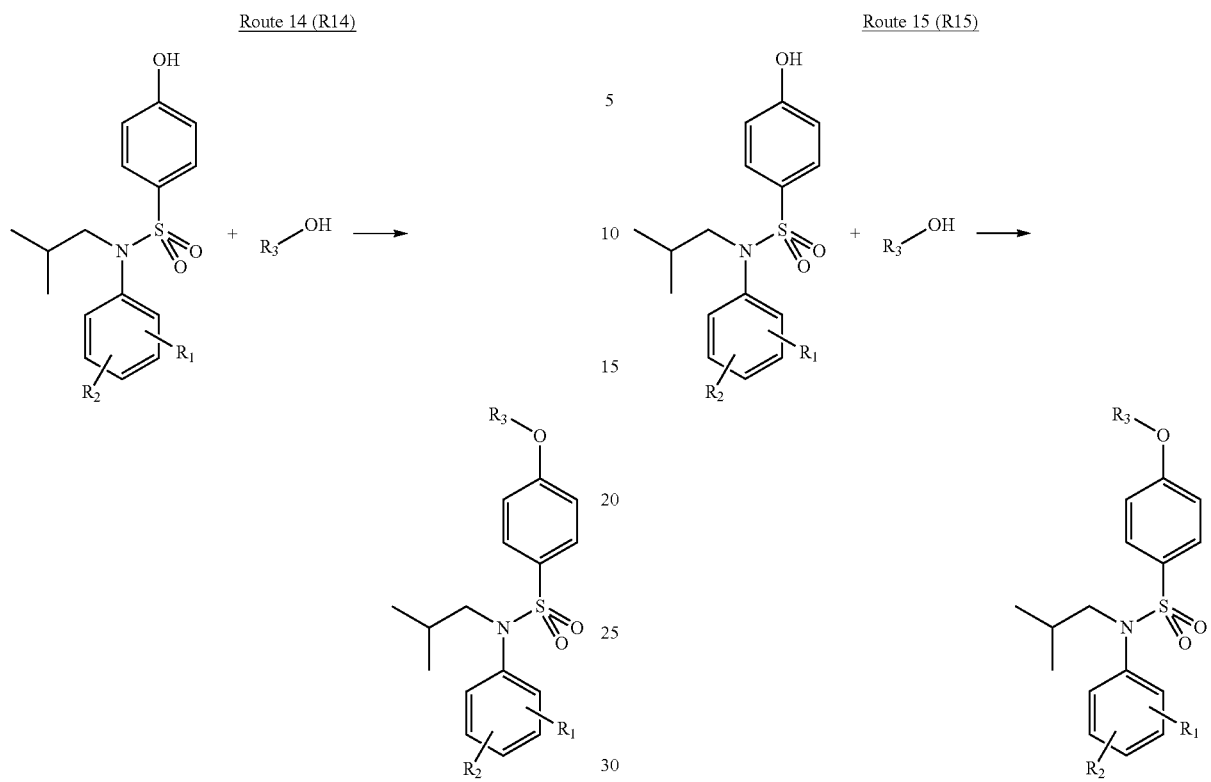

Route 14 (R14)

Route 15 (R15)

Generic Route

This route was performed in an array format. A phenol (1 equivalent, see Table 4 for specific phenol used), an alcohol (1.5 equivalents, see Table 4 for specific alcohol used in each reaction), triphenylphosphine (1.5 equivalents mmol) were pre-weighed into a 4 mL glass vial. Tetrahydrofuran (THF) (4 mL/mmol) was added followed by diisopropyl diazene-1,2-dicarboxylate (DIAD) (1.5 quivalents). The vial was capped and stirred at RT for 2 days. The reaction mixture was filtered to remove any insoluble materials. The sample was purified by mass directed autoPrep on Xbridge column using acetonitrile:water with an ammonium carbonate modifier. The solvent was dried under a stream of nitrogen in the Radleys blowdown apparatus to give the required products.

Specific Example

Preparation of N-(2,4-dimethylphenyl)-N-isobutyl-4-(pyridine-4-ylmethoxy)benzenesulfonamide N-(2,4-dimethylphenyl)-4-hydroxy-N-isobutylbenzenesulfonamide (33 mg, 0.099 mmol), pyridine-4ylmethanol (2.52 mg, 0.148 mmol), triphenylphosphine (39 mg, 0.149 mmol) were pre-weighed into a 4 mL glass vial. Tetrahydrofuran (THF) (0.6 mL) was added followed by diisopropyl diazene-1,2-dicarboxylate (DIAD) (0.029 mL, 0.148 mmol). The vial was capped and stirred at RT for 2 days. The reaction mixture was filtered to remove any insoluble materials. The sample was purified by mass directed autoprep on an Xbridge column using acetonitrile:water with an ammonium carbonate modifier. The solvent was dried under a stream of nitrogen in the Radleys blowdown apparatus to give the required product.

Generic Route

A phenol (1 equivalent, see table 5 for specific phenol used), an alcohol (1.25 equivalents, see Table 4 for specific alcohol used), (4-(3,3,4,4,5,5,6,6,7,7,8,8,9,9,10,10,10-heptadecafluorodecyl)phenyl)diphenylphosphine (Fluoroflash, 1.5 equivalents mmol) were added to Biotage 2-5 mL microwave vessel. Tetrahydrofuran (THF) (14 mL/mmol) was added followed by diisopropyl diazene-1,2-dicarboxylate (DIAD) (1.25 quivalents). The vials were capped and stirred at RT overnight. The reaction mixture was concentrated in vacuo and then diluted with ethyl acetate (85 mL/mmol) and water (85 mL). The organic fraction was separated, dried and then concentrated in vacuo to give the crude product. The crude product was dissolved in DMF:$H_2O$ (9:1) 3.5 mL/mmol, and loaded onto a fluorous column (pre-conditioned with 1 mL DMF, followed by 6 mL MeOH:$H_2O$ (5:1). The semi purified fraction was eluted with 20 mL/mmol MeOH:$H_2O$ (5:1). The fraction was concentrated down, and dissolved in 1:1 MeOH:DMSO 1 mL and purified by mass directed autoprep on Sunfire C18 column using acetonitrile:water with a formic acid modifier. The solvent was dried under a stream of nitrogen in the Radleys blowdown apparatus to give the required product.

Specific Example of Route 15

Preparation of 3-((3,5-dimethylisoxazol-4-yl)methoxy)-N-(2,4-dimethylphenyl)-N-isobutylbenzenesulfonamide N-(2,4-dimethylphenyl)-3-hydroxy-N-isobutylbenzenesulfonamide (76.9 mg, 0.231 mmol), (3,5-dimethylisoxazol-4-yl)methanol (36.7 mg, 0.288 mmol) and (4-(3,3,4,4,5,5,6,6,7,7,8,8,9,9,10,10,10-heptadecafluorodecyl)phenyl) diphenylphosphine (204 mg, 0.288 mmol) were added to a 2-5 mL Biotage microwave vessel. Tetrahydrofuran (THF) (4 mL) was added followed by diisopropyl diazene-1,2-dicarboxylate (DIAD) (0.056 mL, 0.288 mmol). The reaction vial was sealed and left to stir overnight at RT. The reaction mixture was concentrated in vacuo and then diluted with ethyl acetate (25 mL) and water (25 mL). The organic fraction was separated, dried and then concentrated in vacuo to give the crude product. The crude product was dissolved in DMF:H$_2$O (9:1) 1 mL, and loaded onto a fluorous column (preconditioned with 1 mL DMF, followed by 6 mL MeOH:H$_2$O (5:1). The semi purified fraction was eluted with 6 mL MeOH:H$_2$O (5:1). The fraction was concentrated down, and dissolved in 1:1 MeOH:DMSO 1 mL and purified by mass directed autoPrep on Sunfire C18 column using Acetonitrile Water with a Formic acid modifier. The solvent was dried under a stream of nitrogen in the Radleys blowdown apparatus to give the required product, 37.7 mg.

Route 16 (R16)

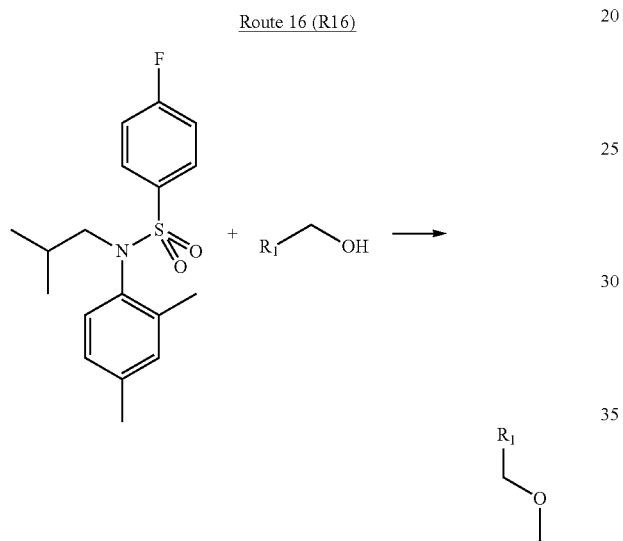

Generic Route

This route was performed in an array format. N-(2,4-dimethylphenyl)-4-fluoro-N-isobutylbenzenesulfonamide (8 equivalents) was dissolved in DMSO or DMF (0.75 mL/mmol×8) and an aliquot (representing 1 equivalent) was added to an alcohol (1 equivalent, see Table 4 for specific alcohol used for each reaction). 60% sodium hydride dispersed on oil (1 equivalent) was added to the reaction. The reaction was capped and sonicated to aid dispersion. The reaction was left to stand at RT for 18 hours. The reaction was quenched with methanol (0.5 mL), and sonicated to aid dispersion. All the samples were purified by mass directed autoprep on an Xbridge column using acetonitrile:water with an ammonium carbonate modifier. The solvent was dried under a stream of nitrogen in the Radleys blowdown apparatus to give the required product (as an ammonium salt where appropriate).

Specific Example

Preparation of N-(3-fluoro-5-methylphenyl)-N-isobutyl-4-(61yridine-4-ylmethoxy)benzenesulfonamide A solution was prepared of an alcohol (0.15 mmol pyridine-4-methanol-16 mg) dissolved in DMF (0.5 mL). This solution was added to the core, 4-fluoro-N-(3-fluoro-5-methylphenyl)-N-(2-methylpropyl)benzenesulfonamide (0.15 mmol, 50.9 mg). 60% sodium hydride dispersed on oil (0.006 g, 0.150 mmol) was added to the reaction. The reaction was capped and sonicated to aid dispersion. The reaction was left to stand at room temperature for 18 hours. Additional 60% sodium hydride dispersed on oil (0.005 g) and alcohol monomer, pyridine-4-methanol (0.5 equivalent) in DMF (0.2 mL) was added and the reaction capped and stirred for an additional 18 hours. Solvent removed to almost a third dry. The sample was dissolved in 1:1 MeOH:DMSO 1 mL (filtered through cotton wool) and split into two batches and purified by mass directed autoprep on an Xbridge column using acetonitrile:water with an ammonium carbonate modifier. The solvent was dried under a stream of nitrogen in the Radleys blowdown apparatus to give the title compound, 12.9 mg.

Route 17 (R17)

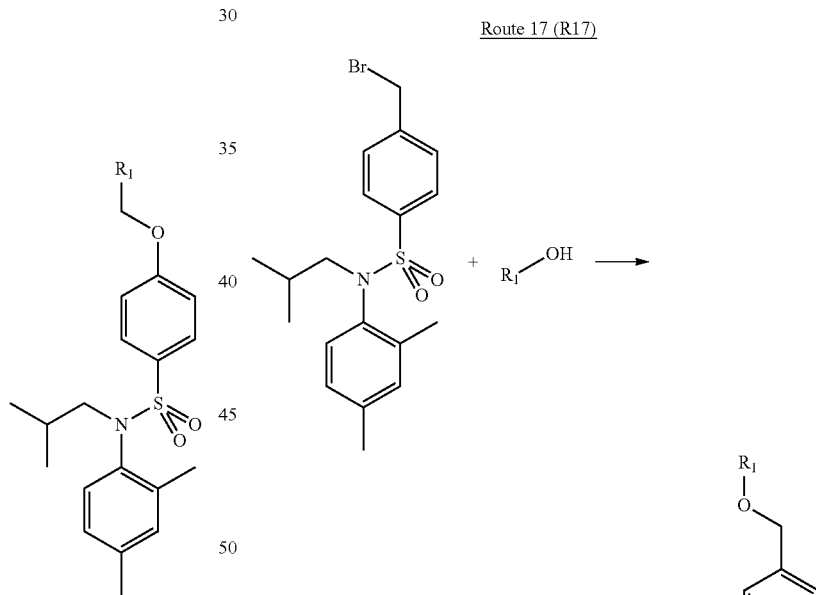

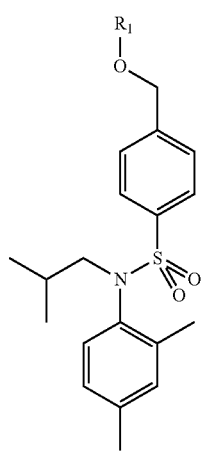

Generic Route

This generic route was performed in an array format. To a solution of an alcohol (1 equivalent, see Table 4 for specific alcohol used) and 4-(bromomethyl)-N-(2,4-dimethylphenyl)-N-isobutylbenzenesulfonamide (1 equivalent) in 2-methyltetrahydrofuran (2-MeTHF) (13 mL/mmol) stirred under nitrogen at room temperature was added solid sodium hydride (60% dispersed in oil, 1 equivalent). The reaction mixture was stirred at 20° C. for 3 hours. The reaction was carefully quenched with water (1 mL/mmol). The solvent was dried under a stream of nitrogen in the Radleys blowdown apparatus to give the crude products. The samples were dissolved in 1:1 MeOH:DMSO 1 mL and purified by mass directed autoprep on Xbridge column using acetonitrile:water with an ammonium carbonate modifier. The solvent was dried under a stream of nitrogen in the Radleys blowdown apparatus to give the required product.

Specific Example

Preparation of N-(2,4-dimethylphenyl)-N-isobutyl-4-((pyridin-4-yloxy)methyl)benzenesulfonamide To a solution of an alcohol (1.276 mg, 0.075 mmol, see Table 4 for specific alcohol used for each reaction) and 4-(bromomethyl)-N-(2,4-dimethylphenyl)-N-isobutylbenzenesulfonamide (0.031 g, 0.075 mmol) in 2-Methyltetrahydrofuran (2-MeTHF) (1 mL) stirred under nitrogen at room temperature was added solid sodium hydride (1.800 mg, 0.075 mmol) (tip of spatula). The reaction mixture was stirred at 20° C. for 3 hrs. The reaction was carefully quenched with water (5 drops per reaction). The solvent was dried under a stream of nitrogen in the Radleys blowdown apparatus to give the crude product. The sample was dissolved in 1:1 MeOH:DMSO 1 mL and purified by mass directed autoprep on an Xbridge column using acetonitrile:water with an ammonium carbonate modifier. The solvent was dried under a stream of nitrogen in the Radley's blowdown apparatus to give the required product (3.89 mg, 10% yield).

Further Example of Route 17 (not Prepared in an Array Format)

Preparation of N-(2,4-dimethylphenyl)-N-isobutyl-4-((pyridine-4-ylmethoxy)methyl)benzenesulfonamide To a solution of crude 4-(bromomethyl)-N-(2,4-dimethylphenyl)-N-isobutylbenzenesulfonamide (100 mg, 0.122 mmol) and pyridine-4-ylmethanol (13.30 mg, 0.122 mmol) in 2-Methyltetrahydrofuran (2-MeTHF) (1 mL) and dimethyl sulfoxide (DMSO) (0.5 mL) stirred in air at RT was added solid sodium hydride (4.87 mg, 0.122 mmol) in one charge, tip of spatula. The reaction mixture was stirred at 20° C. for 16 hours. Reaction was carefully quenched with methanol (0.5 mL) and water (0.5 mL) and evaporated in vacuo to give a residue in DMSO. This was diluted with dichloromethane (10 mL) and water (10 mL) and stirred vigorously for 10 min. The layers were separated by hydrophobic frit and the organic fraction evaporated to give the crude product. The samples were dissolved in 1:1 MeOH:DMSO 1 mL and purified by mass directed autoprep on Sunfire C18 column using acetonitrile:water with a formic acid modifier. The solvent was dried under a stream of nitrogen in the Radleys blowdown apparatus to give the required product N-(2,4-dimethylphenyl)-N-isobutyl-4-((pyridine-4-ylmethoxy)methyl)benzenesulfonamide (4.8 mg, 10.94 μmol, 8.98% yield)

Route 18 (R18)

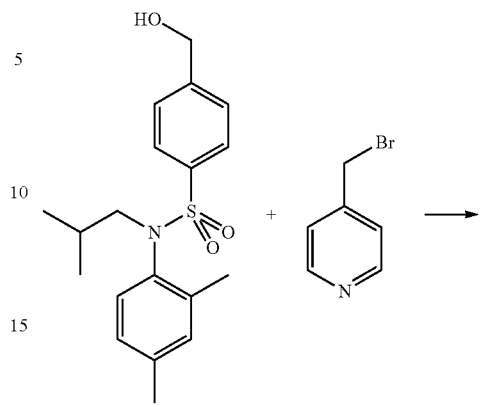

Specific Example

Preparation of N-(2,4-dimethylphenyl)-N-isobutyl-3-((pyridin-4-ylmethoxy)methyl)benzenesulfonamide N-(2,4-dimethylphenyl)-3-(hydroxymethyl)-N-isobutylbenzenesulfonamide (50 mg, 0.144 mmol) and Sodium hydride (60% in Mineral Oil) (6.33 mg, 0.158 mmol) were dissolved in N,N-Dimethylformamide (DMF) (3 mL). To this solution was added 4-(bromomethyl)pyridine (24.75 mg, 0.144 mmol), and the reaction heated to 60° C. and left to stir for 30 min. The reaction solution concentrated on the Biotage V10 and then extracted the crude product to the organic phase of an aqueous work up between ethyl acetate (15 mL) and water (15 mL). The organic phase was separated (hydrophobic frit) and then concentrated in vacuo. The sample was dissolved in 1:1 MeOH:DMSO 1 mL and purified by mass directed autoprep on Sunfire C18 column using acetonitrile:water with a formic acid modifier. The solvent was evaporated in vacuo. The crude product was run through an NH$_2$ SPE column (1 g) eluting with methanol, to remove the formic acid. The product was then dried under a stream of nitrogen on a Radleys blow down unit, to give the final product, 13.5 mg.

TABLE 4

Preparation of Products P98 to P149 by Routes 13 to 18

| Product ID | Route ID | SM1 ID | SM2 ID | SM2 Source | Scale (mmol) | Yield (%) | Work-up | Purification | RT | Base ion (M + 1) |
|---|---|---|---|---|---|---|---|---|---|---|
| P98 | R13 | P83 | B20 | Aldrich | 0.1 | 15 | F | F | 1.14 | 425 |
| P98 | R14 | P83 | B21 | Aldrich | 0.1 | 15 | F | A | 1.13 | 425 |
| P99 | R16 | P94 | B21 | Aldrich | 0.15 | 2 | E | A | 1.06 | 449 |
| P100 | R16 | P90 | B21 | Aldrich | 0.15 | 18 | E | A | 1.06 | 429 |
| P101 | R16 | P89 | B21 | Aldrich | 0.15 | 2 | E | A | 1.1 | 425 |
| P102 | R16 | P88 | B21 | Aldrich | 0.15 | 9 | E | A | 1.03 | 441 |
| P103 | R16 | P91 | B21 | Aldrich | 0.15 | 4 | E | A | 0.99 | 433 |
| P104 | R14 | P92 | B21 | Aldrich | 0.121 | 9 | F | A | 1.05 | 429 |
| P105 | R14 | P86 | B21 | Aldrich | 0.1 | 3 | F | A | 1.09 | 425 |
| P106 | R14 | P85 | B21 | Aldrich | 0.1 | 11 | F | A | 1.1 | 425 |
| P107 | R14 | P87 | B21 | Aldrich | 0.1 | 3 | F | A | 0.98 | 427 |
| P108 | R14 | P84 | B21 | Aldrich | 0.1 | 22 | F | A | 1.03 | 411 |
| P109 | R10 | P76 | B19 | Aldrich | 0.017 | 71 | S | F | 1.5 | 497 |
| P110 | R10 | P48 | B19 | Aldrich | 0.537 | 6 | E | E3 | 1.44 | 432 |
| P111 | R10 | P49 | B19 | Aldrich | 0.152 | 35 | S | A | 1.28 | 451 |
| P112 | R10 | P50 | B19 | Aldrich | 0.819 | 32 | S | A | 1.43 | 483 |
| P113 | R10 | P51 | B19 | Aldrich | 0.328 | 28 | S | A | 1.38 | 483 |
| P114 | R10 | P52 | B19 | Aldrich | 0.082 | 10 | S | A | 1.42 | 483 |
| P115 | R10 | P53 | B19 | Aldrich | 0.157 | 60 | A | F | 1.32 | 451 |
| P116 | R10 | P54 | B19 | Aldrich | 0.295 | 48 | S | A | 1.37 | 443 |
| P117 | R10 | P55 | B19 | Aldrich | 0.289 | 53 | S | A | 1.34 | 447 |
| P118 | R10 | P56 | B19 | Aldrich | 0.342 | 50 | S | A | 1.38 | 443 |
| P119 | R10 | P57 | B19 | Aldrich | 0.131 | 48 | S | A | 1.32 | 459 |
| P120 | R10 | P58 | B19 | Aldrich | 0.295 | 48 | S | A | 1.33 | 447 |
| P121 | R10 | P59 | B19 | Aldrich | 0.224 | 49 | S | A | 1.34 | 449 |
| P122 | R13 | P83 | B22 | ASDI | 0.099 | 4 | F | F | 0.97 | 414 |
| P123 | R16 | P47 | B21 | Aldrich | 0.596 | 20 | S | T | 1.11 | 425 |
| P124 | R13 | P83 | B23 | Maybridge Chemical Co Ltd | 0.099 | 67 | F | F | 1.36 | 442 |
| P125 | R13 | P83 | B24 | Maybridge Chemical Co Ltd | 0.099 | 74 | F | F | 1.41 | 429 |
| P126 | R17 | P73 | B25 | Sigma Aldrich | 0.075 | 10 | E | A | 1.04 | 425 |
| P127 | R17 | P73 | B26 | Sigma Aldrich | 0.075 | 5 | E | A | 1.05 | 426 |
| P128 | R17 | P73 | B21 | Aldrich | 0.122 | 9 | A | F | 1.09 | 439 |
| P129 | R14 | P96 | B27 | Fluorochem | 0.173 | 10 | A | F | 1.4 | 457 |
| P130 | R18 | P96 | B28 | Aldrich | 0.144 | 21 | A | F | 1.11 | 439 |
| P131 | R16 | P47 | B29 | TCI Ltd | 0.149 | 20 | E | A | 0.96 | 428 |
| P132 | R16 | P47 | B30 | Matrix Scientific | 0.149 | 34 | E | A | 1.24 | 429 |
| P133 | R16 | P47 | B31 | Key Organics Ltd | 0.149 | 52 | E | A | 1.03 | 428 |
| P134 | R16 | P47 | B32 | Aldrich | 0.149 | 5 | E | A | 1 | 414 |
| P135 | R10 | P69 | B19 | Aldrich | 0.15 | 21 | S | F | 1 | 471 |
| P136 | R15 | P95 | B27 | Fluorochem | 0.231 | 37 | A & FL | F | 1.51 | 443 |
| P137 | R10 | P72 | B19 | Aldrich | 0.188 | 13 | A | F | 1.36 | 429 |
| P138 | R15 | P95 | B21 | Aldrich | 0.231 | 27 | A & FL | F | 1.18 | 425 |
| P139 | R14 | P96 | B33 | Cayman | 0.144 | 16 | A | F | 1.31 | 440 |
| P140 | R13 | P83 | B28 | Aldrich | 0.099 | 15 | F | F | 1.14 | 425 |
| P141 | R14 | P83 | B34 | ABCR-Gelest (UK) Ltd | 0.099 | 44 | F | A | 1.04 | 439 |
| P142 | R14 | P83 | B35 | Chembridge | 0.099 | 50 | F | A | 1.41 | 457 |
| P143 | R14 | P83 | B33 | Cayman | 0.099 | 20 | F | A | 1.28 | 426 |
| P144 | R10 | P74 | B19 | Aldrich | 1.059 | 72 | E | E1 | 1.43 | 507 |
| P145 | R14 | P83 | B36 | Activate Scientific Ltd | 0.099 | 34 | F | A | 1.1 | 433 |
| P146 | R16 | P47 | B37 | Activate Scientific Ltd | 0.149 | 63 | E | A | 0.99 | 428 |
| P147 | R16 | P47 | B38 | Activate Scientific Ltd | 0.149 | 59 | E | A | 1.24 | 429 |
| P148 | R13 | P75 | B39 | Aldrich | 0.107 | 64 | F | F | 1.38 | 473 |
| P149 | R16 | P47 | B40 | ABCR | 0.745 | 95 | | A | 1.34 | 440 |

Additional Experimental

Preparation of Starting Material A20

4-(3-((tert-butyldimethylsilyl)oxy)propyl)aniline

To a 50 mL round bottomed flask was added 1H-imidazole (59.4 mg, 0.873 mmol), 3-(4-aminophenyl)propan-1-ol 120 mg, 0.794 mmol) and Tetrahydrofuran (THF) (5 mL). To this solution was added tert-butylchlorodimethylsilane (132 mg, 0.873 mmol), and this was left to stir for 2 days, under nitrogen at room temperature. Another 0.5 eq of tert-butylchlorodimethylsilane was added to the reaction and the reaction was left to stir for another 2 hours. After this, reaction was stopped and the suspension concentrated down on a Biotage V10 evaporator, and then the product extracted to the organic phase of an aqueous work up between ethyl acetate (10 mL) and water (10 mL). The organic phase was then passed through a hydrophobic frit, and concentrated in vacuo, leaving the crude product (212 mg, 100%). LCMS (M+1): 266, RT 1.14 mins.

Preparation of Product P150

N-(2,4-dimethylphenyl)-4-(2-hydroxy-2-(pyridin-4-yl)ethoxy)-N-isobutylbenzenesulfonamide a) Preparation of 1-(pyridine-4-yl)ethane-1,2-diol 4-vinylpyridine (2.523 g, 24 mmol) was dissolved in acetone (30 mL) and cooled to ~2° C. (internal temp), with stirring. A solution of potassium permanganate (2.530 g, 16.01 mmol) and magnesium sulfate (962 mg, 7.99 mmol) in water (50 mL) was prepared and added dropwise to the acetone solution, over 20 minutes. The mixture was stirred for an additional 10 minutes, then temperature increased to RT. A small quantity of hydroquinone (26.4 mg, 0.240 mmol) was added to the reaction, then the mixture was filtered through glass sinter. The filtrate was concentrated to 5 mL and ethanol (20 mL) added to precipitate potassium sulfate. The solution stored in the fridge over weekend. The resulting brown precipitate was filtered from the mixture. The mother liquors were evaporated to give a brown oil, 2.85 g. Product was purified by silica (Si) column on Companion (0-25% methanol in DCM, over 23 minutes, UV collection). Combination of the clean product-containing fractions and removal of solvent in vacuo provided desired product, 954 mg, as a pale yellow oil which solidified on cooling. LCMS (M+1) 139, RT 0.36 mins.

b) preparation of N-(2,4-dimethylphenyl)-4-(2-hydroxy-2-(pyridin-4-yl)ethoxy)-N-isobutylbenzenesulfonamide A solution of N-(2,4-dimethylphenyl)-4-fluoro-N-isobutylbenzenesulfonamide (90 mg, 0.268 mmol) was prepared in N,N-dimethylformamide (2 mL) and added to a microwave vial containing potassium carbonate (74.2 mg, 0.537 mmol) and 1-(pyridin-4-yl)ethane-1,2-diol (41.1 mg, 0.295 mmol). The vial was sealed and heated to 130° C. for 30 min by microwaves. After this time, a further portion of potassium carbonate (74.2 mg, 0.537 mmol) was added to the reaction and the mixture heated to 140° C. by microwaves for an additional 30 min. 18-crown-6 (70.9 mg, 0.268 mmol) was then added to the reaction and the mixture heated to 140° C. by microwaves, for a further 30 min. Water (15 mL) was added and the product extracted with DCM (3×15 mL). The combined organics were dried with a hydrophobic frit, then the crude material purified by high-pH MDAP to give the desired product, 18.2 mg. LCMS (M+1) 455, RT 1.27 mins.

Preparation of Product P151

2-(4-(N-(2,4-dimethylphenyl)-N-isobutylsulfamoyl)-2,3-dimethylphenoxy)acetic acid a) Preparation of ethyl {[4-(chlorosulfonyl)-2,3-dimethylphenyl]oxy}acetate Ethyl[(2,3-dimethylphenyl)oxy]acetate (6.1 g, 29.3 mmol) was added dropwise to chlorosulfonic acid (8.78 mL, 132 mmol) at 0° C., with stirring, causing a blood red solution. Reaction stirred for 30 minutes, then allowed to warm to RT. Mixture was stirred for a further 2 hours, then quenched by pouring over ice/water (200 mL). A dark red gum formed, this was extracted into dichloromethane (3×100 mL). Organics were concentrated in vacuo, to give a thick red oil, which crystallized on standing. Product was dried overnight in vacuum oven, to yield 8.179 g as red crystals. No further purification carried out. RT 1.25 mins.

b) Preparation of ethyl[(4-{[(2,4-dimethylphenyl)(2-methylpropyl)amino]sulfonyl}-2,3-dimethylphenyl)oxy]acetate In a 15 mL test tube was placed N-isobutyl-2,4-dimethylamiline (100 mg, 0.564 mmol, prepared, for example, according to P1a, Table 1), ethyl {[4-(chlorosulfonyl)-2,3-dimethylphenyl]oxy}acetate (173 mg, 0.564 mmol,), and di-isopropyl-ethyl-amine (0.197 mL, 1.128 mmol) in dichloromethane (DCM) (2 mL) to give an orange solution. The reaction was stirred at 30° C. for 18 hours. The solvent was removed in vacuo and the residue purified by MDAP in two portions. The fractions from the MDAP were identified by LCMS, combined and the solvent removed in vacuo to give the expected compound. The compound was dissolved in dioxane and freeze dried over night. Yield 16% (41.7 mg) of a white powder. LCMS (M+1) 448, RT 1.52 mins.

c) Preparation of 2-(4-(N-(2,4-dimethylphenyl)-N-isobutylsulfamoyl)-2,3-dimethylphenoxy)acetic acid In a 25 mL round-bottomed flask was placed ethyl[(4-{[(2,4-dimethylphenyl)(2-methylpropyl)amino]sulfonyl}-2,3-dimethylphenyl)oxy]acetate (50 mg, 0.112 mmol) and lithium hydroxide (5.35 mg, 0.223 mmol) in tetrahydrofuran (THF) (3 mL) and Water (1 mL) to give a white suspension. The reaction was stirred overnight at room temperature. The reaction mixture was diluted with ethyl acetate and washed with water (dilute HCl). The organic layer was separated and the solvent removed in vacuo to give the expected compound. The residue was taken up in dioxane and freeze dried overnight. Yield 43%. LCMS (M−1) 418, RT 1.26 mins.

Preparation of Product P152

3-[(4-{[(4-butyl-2-methylphenyl)(2-methylpropyl)amino]sulfonyl}-2-methylphenyl)oxy]propanoic acid To (4-butyl-2-methylphenyl)(2-methylpropyl)amine (21.94 mg, 0.100 mmol, prepared, for example, according to P2, Table 1) in pyridine (1 mL) was added 3-{[4-(chlorosulfonyl)-2-methylphenyl]oxy}propanoic acid (27.9 mg, 0.100 mmol) and left to stand at RT in air for 2 hours. The sample was dissolved in a 1:1 mixture of MeOH and DMSO and was purified by method A (see Table 8) using Waters Xbridge Shield RP18 column. Yield 37%. LCMS (M+1) 462, RT 1.46 mins.

Preparation of Products P153 and P154

N-(2,4-dimethylphenyl)-4-(1-hydroxy-2-((pyridin-3-ylmethyl)amino)ethyl)-N-isobutylbenzenesulfonamide and N-(2,4-dimethylphenyl)-4-(1-hydroxy-2-((pyridin-4-ylmethyl)amino)ethyl)-N-isobutylbenzenesulfonamide a) Preparation of N-(2,4-dimethylphenyl)-N-isobutyl-4-vinylbenzenesulfonamide A suspension of potassium trifluoro(vinyl)borate (241 mg, 1.800 mmol), 4-bromo-N-(2,4-dimethylphenyl)-N-isobutylbenzenesulfonamide (595 mg, 1.5 mmol), cesium carbonate (1466 mg, 4.50 mmol), palladium(II) chloride (5.32 mg, 0.030 mmol) and triphenylphosphine (23.61 mg, 0.090 mmol) was prepared in tetrahydrofuran (THF) (2 mL) and Water (0.2 mL). The mixture was heated to 140° C. by microwaves for 30 min, to yield a black suspension. Additional ½ eq of potassium trifluoro(vinyl)borate (121 mg, 0.9 mmol) was added, along with extra water (0.2 mL) and THF (2 mL) and reaction heated for a further 1 hour at 140° C. The reaction mixture was diluted with dichloromethane (15 mL) and water (5 mL), then filtered through a plug of celite to remove palladium catalyst. The resulting yellow solution was dried using a hydrophobic frit, concentrated, then purified by flash (Si) using 0-25% ethyl acetate/cyclohexane over 40 minutes. Fractions were combined to give a clear oil, 385.3 mg, and the product taken directly to the next step, without further purification. LCMS (M+1) 344, RT 1.48 mins.

b) Preparation of N-(2,4-dimethylphenyl)-N-isobutyl-4-(oxiran-2-yl)benzenesulfonamide A solution of N-(2,4-dimethylphenyl)-N-isobutyl-4-vinylbenzenesulfonamide (380.2 mg, 1.107 mmol) was prepared in dichloromethane (DCM) (5 mL) and mCPBA (764 mg, 4.43 mmol) added at 0° C. The reaction was stirred over the weekend from 0° C. to 25° C. The reaction was washed with water (15 mL), sodium hydroxide (2×15 mL) and brine (15 mL), then concentrated in vacuo. Purification by flash (Si) using 0-25% ethyl acetate in cyclohexane gave the desired product 195.8 mg as a clear oil. Yield 49%. LCMS (M+1) 360, RT 1.38 mins.

c) Preparation of N-(2,4-dimethylphenyl)-4-(1-hydroxy-2-((pyridin-3-ylmethyl)amino)ethyl)-N-isobutylbenzenesulfonamide A solution of pyridin-3-ylmethanamine (10.38 mg, 0.096 mmol) in ethanol (0.25 mL) was prepared in a 4 mL reaction vial and triethylamine (0.027 mL, 0.192 mmol) added. A solution of N-(2,4-dimethylphenyl)-N-isobutyl-4-(oxiran-2-yl)benzenesulfonamide (28.8 mg, 0.08 mmol) in ethanol (0.75 mL) was then added and the reaction heated at 40° C. overnight. After this time, further pyridin-3-ylmethanamine (10.38 mg, 0.096 mmol) was added and the reaction heated at 50° C. for an additional 2 hours. The reaction mixture was then concentrated under a stream of nitrogen and the crude mixture purified by high-pH MDAP to give the required product, 10.6 mg. LCMS (M+1) 468, RT 1.24 mins.

d) Preparation of N-(2,4-dimethylphenyl)-4-(1-hydroxy-2-((pyridin-4-ylmethyl)amino)ethyl)-N-isobutylbenzenesulfonamide A solution of pyridin-4-ylmethanamine (10.38 mg, 0.096 mmol) in ethanol (0.25 mL) was prepared in a 4 mL reaction vial and triethylamine (0.027 mL, 0.192 mmol) added. A solution of N-(2,4-dimethylphenyl)-N-isobutyl-4-(oxiran-2-yl)benzenesulfonamide (28.8 mg, 0.08 mmol) in ethanol (0.75 mL) was then added and the reaction heated at 50° C. overnight. The reaction mixture was then concentrated under a stream of nitrogen and the crude mixture purified by high-pH MDAP to give the required product, 10.5 mg. LCMS (M+1) 468, RT 1.22 mins.

Preparation of Product P155

4-((3,5-dimethylisoxazol-4-yl)methoxy)-N-(4-(2-hydroxypropan-2-yl)-2-methylphenyl)-N-isobutyl-benzenesulfonamide To a solution of ethyl 4-(4-((3,5-dimethylisoxazol-4-yl)methoxy)-N-isobutylphenylsulfonamido)-3-methylbenzoate (66 mg, 0.132 mmol) in toluene (0.53 mL) and tetrahydrofuran (THF) (0.530 mL) stirred under nitrogen at 0° C. was added a solution of methylmagnesium bromide in butyl ether (0.264 mL, 0.264 mmol) dropwise. The reaction mixture was stirred at 0° C. for 30 min and then allowed to warm up to RT and stirred for 2 hours. The reaction mixture was diluted with dichloromethane (5 mL). The organic phase was washed with water 10 mL, dried using a hydrophobic frit and dried under a stream of nitrogen in the Radleys blowdown apparatus to give the crude product. The samples was dissolved in 1:1 MeOH:DMSO 1 mL and purified by mass directed autoprep on a Sunfire C18 column using acetonitrile:water with a formic acid modifier. The solvent was dried under a stream of nitrogen in the Radleys blowdown apparatus to give the required product, 22 mg as a colorless oil. Yield 34%. LCMS (M−18) 469, RT 1.25 mins.

Preparation of Product P156

4-((3,5-dimethylisoxazol-4-yl)methoxy)-N-(4-(2-hydroxyethoxy)-2-methylphenyl)-N-isobutylbenzenesulfonamide a) Preparation of 4-((3,5-dimethylisoxazol-4-yl)methoxy)-N-isobutyl-N-(2-methyl-4-(2-((tetrahydro-2H-pyran-2-yl)oxy)ethoxy)phenyl)benzenesulfonamide An aliquot of tetrahydrofuran (THF) (1 mL) containing 4-((3,5-dimethylisoxazol-4-yl)methoxy)-N-(4-hydroxy-2-methylphenyl)-N-isobutylbenzenesulfonamide (50 mg, 0.112 mmol) and DIAD (0.048 mL, 0.247 mmol) was added to triphenylphosphine (64.9 mg, 0.247 mmol). The reaction mixture was sealed and left to stir for 10 minutes before addition of 2-((tetrahydro-2H-pyran-2-yl)oxy)ethanol (0.015 mL, 0.112 mmol). The sealed reaction mixture was then heated to 50° C. over night. LCMS showed the formation of the product. LCMS (M+1) 572, RT 1.4 mins. Used without further purification in next reaction.

b) Preparation of 4-((3,5-dimethylisoxazol-4-yl)methoxy)-N-(4-(2-hydroxyethoxy)-2-methylphenyl)-N-isobutylbenzenesulfonamide To a solution of 4-((3,5-dimethylisoxazol-4-yl)methoxy)-N-isobutyl-N-(2-methyl-4-(2-((tetrahydro-2H-pyran-2-yl)oxy)ethoxy)phenyl)benzenesulfonamide (51.2 mg, 0.089 mmol) in tetrahydrofuran (THF) (4 mL) stirred at room temperature was added a solution of 4M HCl in dioxane (4 mL, 16.00 mmol). The reaction mixture was stirred at room temperature for 1 hour. The solvent was dried under a stream of nitrogen in the Radleys blowdown apparatus to give the crude product. The sample was dissolved in 1:1 MeOH:DMSO 1 mL and purified by Open Access Mass Directed AutoPrep on Sunfire C18 column using Acetonitrile Water with a Formic acid modifier. The solvent was dried under a stream of nitrogen in the Radleys blowdown apparatus to give the required product, 27 mg as colourless oil which solidified. LCMS (M+1) 489, RT 1.14 mins.

Preparation of Product P157

4-((3,5-dimethylisoxazol-4-yl)methoxy)-N-(4-(hydroxymethyl)-2-methylphenyl)-N-isobutylbenzenesulfonamide To a solution of ethyl 4-(4-((3,5-dimethylisoxazol-4-yl)methoxy)-N-isobutylphenylsulfonamido)-3-methylbenzoate (40 mg, 0.080 mmol) in THF (5 mL) stirred under nitrogen at 0° C. was added a solution of LiAlH$_4$ 1M in diethyl ether (0.160 mL, 0.160 mmol) dropwise. The reaction mixture was stirred at 0° C. for 30 minutes. The reaction was then allowed to warm up to room temperature and stirred for 2 hours. The reaction mixture was diluted with dichloromethane (10 mL). The organic phase was washed with water 10 mL, and saturated brine 10 mL, dried using a hydrophobic frit and concentrated under a stream of nitrogen in the Radleys blowdown apparatus to give the crude product. The crude was dissolved in 1:1 MeOH:DMSO 1 mL and purified by mass directed autoprep on a Sunfire C18 column using acetonitrile:water with a formic acid modifier. The solvent was dried under a stream of nitrogen in the Radleys blowdown apparatus to give the required product, 23.6 mg colorless oil which solidified. LCMS (M+1) 459, RT 1.14 mins.

Preparation of Product P158

4-((3,5-dimethylisoxazol-4-yl)methoxy)-N-(4-(3-hydroxypropyl)phenyl)-N-isobutylbenzenesulfonamide N-(4-(3-((tert-butyldimethylsilyl)oxy)propyl)phenyl)-4-((3,5-dimethylisoxazol-4-yl)methoxy)-N-isobutylbenzenesulfonamide (276.8 mg, 0.472 mmol) was dissolved in Tetrahydrofuran (THF) (10 mL). To this solution was added TBAF in THF (1M) (0.707 mL, 0.707 mmol), and the solution was left to stir for 1 hr at room temperature. The reaction mixture was concentrated on the Biotage V10 evaporator, extracted to the organic phase of an aqueous workup between ethyl acetate (10 mL) and water (10 mL) followed by a brine (10 mL) wash. The organic phase was passed through a hydrophobic frit, and concentrated in vacuo, before being dissolved in DCM and loaded onto a silica column and purified by column chromatography on Biotage II Flashmaster (20 g silica (Si), 40 mins, 0-50% EtOAc in cyclohexane). The relevant fractions were combined and condensed and the sample was freeze dried using a minimum of dioxane in water, to give the final product, 67%. LCMS (M+1) 473.1, RT 1.16 mins.

Preparation of Product P159

4-(4-(N-(2,4-dimethylphenyl)-N-isobutylsulfamoyl) phenyl)butanoic acid a) Preparation of methyl 4-(4-(N-(2,4-dimethylphenyl)-N-isobutylsulfamoyl)phenyl)-4-nitrobutanoate To a solution of methyl 4-nitrobutanoate (0.047 mL, 0.378 mmol), 4-bromo-N-(2,4-dimethylphenyl)-N-isobutylbenzenesulfonamide (100 mg, 0.252 mmol), di-tert-butyl(2'-methyl-[1,1'-biphenyl]-2-yl)phosphine (7.88 mg, 0.025 mmol) and cesium carbonate (99 mg, 0.303 mmol) in 1,2-Dimethoxyethane (DME) (1.5 mL) at RT was added solid Pd(II)(dba)2 (7.25 mg, 0.013 mmol), ensuring all particles were under the solvent level. The vial was flushed with nitrogen for 2 minutes. The reaction vessel was sealed and heated in Emrys Optimiser using initial high absorbance to 120° C. for 30 min. After cooling the reaction was analysed. Product was present as well as starting material. The vessel was resealed and heated at 120° C. for a further 30 min. No change in analysis. The reaction mixture was passed through a prepacked silica cartridge (500 mg) to remove palladium residue; the cartridge was washed with methanol (5 mL). The resulting filtrate was evaporated in vacuo to give a residue. The samples were dissolved in 1:1 MeOH:DMSO 1 mL and purified by Open Access Mass Directed AutoPrep on Sunfire C18 column using Acetonitrile Water with a Formic acid modifier. The solvent was dried under a stream of nitrogen in the Radleys blow down apparatus to give the required product 28 mg. (43% yield). LCMS (M+1) 418; RT 1.45.

b) Preparation of methyl 4-(4-(N-(2,4-dimethylphenyl)-N-isobutylsulfamoyl)phenyl)butanoate A solution of methyl 4-(4-(N-(2,4-dimethylphenyl)-N-isobutylsulfamoyl)phenyl)-4-nitrobutanoate (28 mg, 0.061 mmol) in Ethanol (2 mL) was prepared. The reaction was hydrogenated using the H-cube (settings: 20° C., 1 bar, 1 mL/min flow rate) and 10% Pd/C CatCart 30 as the catalyst. Analysis showed loss of nitro group. The solvent was evaporated in vacuo. The samples were dissolved in 1:1 MeOH: DMSO 1 mL and purified by Open Access Mass Directed AutoPrep on Sunfire C18 column using Acetonitrile Water with a Formic acid modifier. The solvent was dried under a stream of nitrogen in the Radleys blowdown apparatus to give the required product 10.9 mg. LCMS (M+1) 418; Rt 1.45 mins.

c) Preparation of 4-(4-(N-(2,4-dimethylphenyl)-N-isobutylsulfamoyl)phenyl)butanoic acid To a solution of methyl 4-(4-(N-(2,4-dimethylphenyl)-N-isobutylsulfamoyl)phenyl)butanoate (10.9 mg, 0.026 mmol) in tetrahydrofuran (THF) (0.25 mL) stirred in air at RT was added a solution of lithium hydroxide (0.625 mg, 0.026 mmol) in water (0.250 mL) in one charge. The reaction mixture was stirred at 20° C. for 30 min, to ensure dissolution and then left to stand overnight. Analysis showed complete conversion. The reaction mixture was evaporated and the residue partitioned between ethyl acetate 5 mL and water 5 mL, stirring vigorously for 2 hours before separation with a hydrophilic frit. Analysis showed product to be in both layers. Both layers were separately acidified (2N hydrochloric acid, ca. 1 mL), diluted with water (2 mL) and dichloromethane (2×3 mL). The organic fractions were separated by hydrophobic frit. The appropriate fractions were combined and dried under a stream of nitrogen in the Radleys blowdown apparatus to give the two batches of the required product 5.75 mg and 3.05 mg. LCMS (M+1) 404, RT 1.27 mins.

Preparation of Product P160

4-((3,5-dimethylisoxazol-4-yl)methoxy)-N-(4-ethylphenyl)-N-isobutylbenzenesulfonamide a) Preparation of 4-ethyl-N-(2-methylpropyl)aniline A mixture of 2-methyl-1-propanol (5.94 mL, 64.40 mmol), 4-ethylaniline (2 mL, 16.09 mmol), potassium iodide (5.342 g, 32.2 mmol) and [Cp*IrCl$_2$]$_2$ (128 mg, 0.161 mmol) was prepared in water (10 mL). This mixture was heated by microwaves to 150° C. for 1.5 hours. After cooling, the reaction mixture was diluted with dichloromethane (20 mL) and water (10 mL) then stirred vigorously for 3 minutes. The organic phase was separated (hydrophobic frit) and the aqueous phase was diluted with further dichloromethane (10 mL) then stirred vigorously for 2 minutes and separated (hydrophobic frit). The combined organic fractions were evaporated in vacuo to give the crude product as a brown oil. The crude was purified by flash silica (Si) chromatography (using a 0-50% dichloromethane-cyclohexane gradient). The appropriate fractions were combined and evaporated in vacuo to give the title compound as a pale yellow oil. (1.9285 g, 77%). LCMS (M+1) 178, RT 0.91 mins.

b) Preparation of 4-((3,5-dimethylisoxazol-4-yl) methoxy)-N-(4-ethylphenyl)-N-isobutylbenzene- sulfonamide To 4-ethyl-N-isobutylaniline (50 mg, 0.282 mmol) in pyridine (1 mL) was added 4-{[(3,5-dimethyl-4-isoxazolyl)methyl]oxy}benzenesulfonyl chloride (94 mg, 0.310 mmol) and the reaction stood at room temperature, in air, for 16 hours. The crude was then purified by MDAP (Method F), to provide 103.6 mg of desired product. LCMS (M+1) 443, RT 1.39 mins.

Preparation of Product P161

(R)-3-((4-(N-(2,4-dimethylphenyl)-N-isobutylsulfamoyl)-2-methylphenyl)amino)-4-hydroxybutanoic acid a) Preparation of N-(2,4-dimethylphenyl)-4-fluoro-N-isobutyl-3-methylbenzenesulfonamide To (2,4-dimethylphenyl)(2-methylpropyl)amine (300 mg, 1.692 mmol) in pyridine (5 mL) was added 4-fluoro-3-methylbenzene-1-sulfonyl chloride (353 mg, 1.692 mmol) and the reaction stood at room temperature, in air, for 16 hours. The crude was then passed through an aminopropyl ($NH_2$) SPE (solid phase extraction) cartridge eluting with methanol followed by a sulfonic acid (SCX) SPE, eluting with methanol. The appropriate fractions were combined and concentrated under a stream of nitrogen to give the crude product. The crude purified by flash silica (Si) chromatography (using a 0-100% ethyl acetate-cyclohexane gradient). The appropriate fractions were combined and evaporated in vacuo to give the required product, 527 mg as a yellow oil which solidified on standing. LCMS (M+15) 458, RT 1.46 mins.

b) Preparation of (R)-3-(4-(N-(2,4-dimethylphenyl)-N-isobutylsulfamoyl)-2-methylphenyl)amino)-4-hydroxybutanoic acid A solution of (S)-3-amino-4-hydroxybutanoic acid (17.04 mg, 0.143 mmol) was prepared in DMSO (1.0 mL) and N-(2,4-dimethylphenyl)-4-fluoro-N-isobutyl-3-methylbenzenesulfonamide (50 mg, 0.143 mmol) added. The solution was then treated with sodium hydride (60% dispersion in oil, 17.17 mg, 0.429 mmol). The reaction was stirred under nitrogen for 2 hours to aid dispersion, then stood at room temperature for 5 days. The reaction was quenched with isopropanol (0.5 mL) and water (0.5 mL), then concentrated in vacuo. The crude was dissolved in a 1:1 mixture of MeOH:DMSO (1 mL), filtered (cotton wool plug) and purified by MDAP (Method A) to give the title compound, 8.2 mg. LCMS (M+1) 449, RT 0.93 mins.

Preparation of Product P162

(S)-2-(4-(N-(2,4-dimethylphenyl)-N-isobutylsulfamoyl)phenyl)amino)-3-hydroxypropanoic acid A solution of (S)-2-amino-3-hydroxypropanoic acid (15.67 mg, 0.149 mmol) was prepared in DMSO (1.0 mL) and N-(2,4-dimethylphenyl)-4-fluoro-N-isobutylbenzenesulfonamide (50 mg, 0.149 mmol) added. The solution was then treated with sodium hydride (60% dispersion in oil, 17.89 mg, 0.447 mmol). The reaction was stirred under nitrogen for 2 hours to aid dispersion, then quenched with isopropanol (0.5 mL) and water (0.5 mL) and concentrated in vacuo. The sample was partitioned between water (5 mL) and dichloromethane (5 mL) and the organics separated (hydrophobic frit). The crude was purified by MDAP (Method A) to give the required product 1.6 mg. LCMS (M+1) 421, RT 0.93 min.

Preparation of Product P163

(S)-3-((4-(N-(2,4-dimethylphenyl)-N-isobutylsulfamoyl)phenyl)amino)-4-hydroxybutanoic acid A solution of (S)-3-amino-4-hydroxybutanoic acid (17.76 mg, 0.149 mmol) was prepared in DMSO (1.0 mL) and N-(2,4-dimethylphenyl)-4-fluoro-N-isobutylbenzenesulfonamide (50 mg, 0.149 mmol) added. The solution was then treated with sodium hydride (60% dispersion in oil, 17.89 mg, 0.447 mmol). The reaction was stirred under nitrogen for 2 hours to aid dispersion, then stood at room temperature for 5 days. The reaction was quenched with isopropanol (0.5 mL) and water (0.5 mL), then concentrated in vacuo. The crude was dissolved in a 1:1 mixture of MeOH:DMSO (1 mL), filtered (cotton wool plug) and purified by MDAP (Method A) to give the title compound, 7.98 mg. LCMS (M+1) 435, RT 0.91 mins.

Preparation of Product P164

N-(2,4-dimethylphenyl)-N-isobutyl-4-(2H-tetrazol-5-yl)benzenesulfonamide

To a solution of (2,4-dimethylphenyl)(2-methylpropyl) amine (100 mg, 0.564 mmol) in pyridine (2 mL) was added 4-(2H-tetrazol-5-yl)benzene-1-sulfonyl chloride (138 mg, 0.564 mmol) and the mixture stirred at 20° C. for 30 minutes, then stood at room temperature, in air, for 16 hours. The crude was then purified by flash silica (Si) chromatography (using a 25-100% ethyl acetate-cyclohexane gradient) to give a colourless gum. This was further dried under a stream of nitrogen, then under vacuum for 3 hours, to give the final product, 104.87 mg. LCMS (M+1) 386, RT 1.22 mins.

Preparation of Product P165

(R)-3-((4-(N-(2,4-dimethylphenyl)-N-isobutylsulfamoyl)phenyl)amino)-4-hydroxybutanoic acid A solution of (R)-3-amino-4-hydroxybutanoic acid hydrochloride (23.19 mg, 0.149 mmol) was prepared in DMSO (1.0 mL) and N-(2,4-dimethylphenyl)-4-fluoro-N-isobutylbenzenesulfonamide (50 mg, 0.149 mmol) added. The solution was then treated with sodium hydride (60% dispersion in oil, 17.89 mg, 0.447 mmol). The reaction was stirred under nitrogen for 2 hours to aid dispersion, then stood at room temperature for 5 days. The reaction was quenched with isopropanol (0.5 mL) and water (0.5 mL), then concentrated in vacuo. The crude was dissolved in a 1:1 mixture of MeOH:DMSO (1 mL), filtered (cotton wool plug) and purified by MDAP (Method A) to give the title compound, 6.09 mg. LCMS (M+1) 435, RT 0.91 mins.

Preparation of Product P166

3-(4-(N-isobutyl-N-(2-methyl-5-(trifluoromethyl) phenyl)sulfamoyl)phenyl)propanoic acid a) Preparation of methyl 3-[4-({(2-methylpropyl)[2-methyl-5-(trifluoromethyl)phenyl]amino}sulfonyl) phenyl]propanoate To a solution of (2-methylpropyl)[2-methyl-5-(trifluoromethyl)phenyl]amine (50 mg, 0.216 mmol) in pyridine (5 mL)

was added methyl 3-[4-(chlorosulfonyl)phenyl]propanoate (56.8 mg, 0.216 mmol). The mixture was stirred for 30 minutes to ensure dilution, then stood at room temperature, in air, for 16 hours. The solvent was evaporated in vacuo to give the crude product which was purified by MDAP (Method F) to give the required product, 21.5 mg. LCMS (M+1) 458, RT 1.39 mins.

b) Preparation of 3-(4-(N-isobutyl-N-(2-methyl-5-(trifluoromethyl)phenyl)sulfamoyl)phenyl)propanoic acid To a stirred solution of methyl 3-(4-(N-isobutyl-N-(2-methyl-5-(trifluoromethyl)phenyl)sulfamoyl)phenyl)propanoate (15 mg, 0.033 mmol) in tetrahydrofuran (THF) (1.5 mL) at room temperature, was added a solution of lithium hydroxide (approximately 0.785 mg, 0.033 mmol—tip of spatula used) in water (1.5 mL). The reaction mixture was stirred at 20° C. for 4 hours and then stood overnight. The mixture was concentrated in vacuo then partitioned between water (2 mL) and ethyl acetate (2×5 mL). The aqueous layer was separated (hydrophilic frit) and acidified, then extracted with ethyl acetate (5 mL). The organic layer was separated (hydrophobic frit) and concentrated in vacuo to give required product, 2.4 mg. LCMS (M+1) 444, RT 1.25 mins.

Preparation of Product P167

3-(4-(N-isobutyl-N-(2-methyl-5-(trifluoromethyl) phenyl)sulfamoyl)phenyl)-2,2-dimethylpropanoic acid a) Preparation of ethyl 3-(4-(N-isobutyl-N-(2-methyl-5-(trifluoromethyl)phenyl)sulfamoyl)phenyl)-2,2-dimethylpropanoate To a stirred solution of (2-methylpropyl)[2-methyl-5-(trifluoromethyl)phenyl]amine (50 mg, 0.216 mmol) in pyridine (5 mL) in air, at room temperature, was added ethyl 3-[4-(chlorosulfonyl)phenyl]-2,2-dimethylpropanoate (65.9 mg, 0.216 mmol). The reaction mixture was stirred at 20° C. for 30 minutes, then stood overnight. The solvent was evaporated in vacuo to give the crude material which was then purified by MDAP (Method F) to give the required product, 20 mg. LCMS (M+1) 500, RT 1.53 mins.

b) Preparation of 3-(4-(N-isobutyl-N-(2-methyl-5-(trifluoromethyl)phenyl)sulfamoyl)phenyl)-2,2-dimethylpropanoic acid To a stirred solution of ethyl 3-(4-(N-isobutyl-N-(2-methyl-5-(trifluoromethyl)phenyl)sulfamoyl)phenyl)-2,2-dimethylpropanoate (15 mg, 0.030 mmol) in tetrahydrofuran (THF) (1.5 mL), at room temperature, was added a solution of lithium hydroxide (approximately 0.719 mg, 0.030 mmol—tip of spatula used) in water (1.5 mL). The reaction mixture was stirred at 20° C. for 4 hours and then stood overnight. The mixture was evaporated in vacuo, then partitioned between water (2 mL) and ethyl acetate (2×5 mL). The organic fraction was separated (hydrophilic frit) and evaporated in vacuo to give a residue. This was redissolved in THF (1 mL) and water (1 mL) and new lithium hydroxide (tip of spatula) was added. The reaction was stood for 3 days, after which time the solvents had evaporated to give a white residue. The residue was acidified (2N HCl, 3 mL) and extracted with ethyl acetate (2×5 mL). The organics were separated (hydrophobic frit) and concentrated in vacuo, then purified by MDAP (Method F) to give the required product, 2.38 mg. LCMS (M+1) 472, RT 1.37 mins.

Preparation of Product P168

5-(N-(2,4-dimethylphenyl)-N-isobutylsulfamoyl)-2-methoxybenzoic acid

To a solution of (2,4-dimethylphenyl)(2-methylpropyl) amine (200 mg, 1.128 mmol) in pyridine (3 mL) was added 5-(chlorosulfonyl)-2-methoxybenzoic acid (283 mg, 1.128 mmol) and the reaction stirred at 20° C. for 4 hours. The solvent was removed in vacuo and the crude purified by flash silica (Si) chromatography (using a 0-100%, ethyl acetate-dichloromethane gradient, with extra 0-20% methanol added). The appropriate fractions were combined and evaporated in vacuo to give the required product, 108 mg. LCMS (M+1) 392, RT 1.18 mins.

Preparation of Product P169

2-((4-(N-(2,4-dimethylphenyl)-N-isobutylsulfamoyl) phenyl)amino)-3-hydroxypropanoic acid A solution of 2-amino-3-hydroxypropanoic acid (15.67 mg, 0.149 mmol) was prepared in DMSO (1.0 mL) and N-(2,4-dimethylphenyl)-4-fluoro-N-isobutylbenzenesulfonamide (50 mg, 0.149 mmol) added. The solution was then treated with sodium hydride (60% dispersion in oil, 5.96 mg, 0.149 mmol) and the reaction stirred under nitrogen for 2 hours. The mixture was then quenched with isopropanol (0.5 mL) and water (0.5 mL) and the solvent removed in vacuo. The sample was partitioned between water (5 mL) and dichloromethane (5 mL) and the organics separated (hydrophobic frit). The crude was purified by MDAP (Method A) to give the required product 1.0 mg. LCMS (M+1) 421, RT 1.17 mins.

Preparation of Product P170

N-(2,6-difluorophenyl)-4-{[(3,5-dimethyl-4-isoxazolyl)methyl]oxy}-N-(2-methylpropyl)benzenesulfonamide a) Preparation of 2,6-difluoro-N-(2-methylpropyl)aniline 2,6-difluoroaniline (387 mg, 3 mmol), potassium iodide (996 mg, 6.00 mmol) and [Cp*IrCl$_2$]$_2$ (33.1 mg, 0.030 mmol) were dissolved in 2-methyl-1-propanol (3 mL, 32.4 mmol). The resulting mixture was heated by microwaves to 190° C. for 8 hours. To the reaction mixture was added dichloromethane (10 mL) and water (10 mL) and the organic phase separated (hydrophobic frit). Diethyl ether was added and the solution filtered through a silica cartridge (10 g) eluting with further diethyl ether. The filtrate was evaporated in vacuo, then purified by flash silica (Si) chromatography (using a 0-100% dichloromethane-cyclohexane gradient). The appropriate fractions were combined and concentrated to give the title product (80 mg) as a colourless oil. LCMS (M+1) 186, RT 1.26 mins.

b) Preparation of N-(2,6-difluorophenyl)-4-{[(3,5-dimethyl-4-isoxazolyl)methyl]oxy}-N-(2-methylpropyl)benzenesulfonamide To a solution of (2,6-difluorophenyl)(2-methylpropyl) amine (80 mg, 0.432 mmol) in pyridine (1 mL) was added 4-{[(3,5-dimethyl-4-isoxazolyl)methyl]oxy}benzenesulfonyl chloride (156 mg, 0.518 mmol) and the reaction stood at room temperature, in air, for 16 hours. The solvent was removed in vacuo and the crude then passed through a sulfonic acid (SCX) SPE (solid phase extraction) cartridge eluting with methanol followed by 2M ammonia/methanol solution. The product-containing fractions were concentrated in vacuo and the crude then passed through an aminopropyl (NH$_2$) SPE cartridge eluting with methanol followed by 2M ammonia/methanol solution. The appropriate fractions were combined and concentrated in vacuo, then further purified by MDAP (Method F) to give the required product, 0.6 mg. LCMS (M+18) 468, RT 1.28 mins.

Preparation of Product P171

2-bromo-5-(N-(4-ethylphenyl)-N-isobutylsulfamoyl)benzoic acid a) Preparation of methyl 2-bromo-5-(N-(4-ethylphenyl)-N-isobutylsulfamoyl)benzoate To a solution of 4-ethyl-N-isobutylaniline (400 mg, 2.256 mmol) in pyridine (2 mL) was added methyl 2-bromo-5-(chlorosulfonyl)benzoate (707 mg, 2.256 mmol) portionwise, over 30 minutes. The reaction mixture was stirred at 20° C. for 30 minutes then stood at room temperature, in air, for 16 hours. The solvent was evaporated in vacuo to give a crude yellow solid. The crude was then triturated with methanol, filtered and dried in vacuo to give the desired product (600 mg) as a white solid. LCMS (M+1) 454/456, RT 1.41 mins.

b) Preparation of 2-bromo-5-(N-(4-ethylphenyl)-N-isobutylsulfamoyl)benzoic acid

To a suspension of methyl 2-bromo-5-(N-(4-ethylphenyl)-N-isobutylsulfamoyl)benzoate (300 mg, 0.660 mmol), palladium(II) acetate (14.82 mg, 0.066 mmol), 1-(vinyloxy)butane (BVE) (0.427 mL, 3.30 mmol) and triphenylphosphine (34.6 mg, 0.132 mmol) in acetonitrile (1 mL) in air, at room temperature, was added triethylamine (0.110 mL, 0.792 mmol). The reaction vessel was sealed and heated by microwaves to 150° C. for 1 hour then the solvent was evaporated in vacuo and the residue redissolved in tetrahydrofuran (THF) (1.0 mL) and treated with HCl (2N, 1 mL, 3.29 mmol). The mixture was stirred vigorously for 1 hour then stood overnight. Analysis showed hydrolysed starting material was present. The crude was purified by MDAP (Method F) to isolate the hydrolysed starting material as the product, 84.8 mg. LCMS (M+1) 440/442, RT 1.25 mins.

Preparation of Product P172

2-(4-(N-(4-butyl-2-methylphenyl)-N-isobutylsulfamoyl)-2-methylphenoxy)acetic acid To (4-butyl-2-methylphenyl)(2-methylpropyl)amine (21.94 mg, 0.100 mmol) in pyridine (1 mL) was added {[4-(chlorosulfonyl)-2-methylphenyl]oxy}acetic acid (26.5 mg, 0.100 mmol) and reaction stood for 2 hours at room temperature. The sample was then dissolved in a 1:1 mixture of MeOH and DMSO and purified by MDAP Method A2, to provide the desired product, 11 mg. LCMS (M+1) 448, RT 1.44 mins.

Preparation of Product P173

4-((2-(dideuterioamino)pyridin-4-yl)methoxy)-N-(2,4-dimethylphenyl)-N-isobutylbenzenesulfonamide To a solution of (2-aminopyridin-4-yl)methanol (37.0 mg, 0.298 mmol) and N-(2,4-dimethylphenyl)-4-fluoro-N-isobutylbenzenesulfonamide (100 mg, 0.298 mmol) in d6-DMSO (1 mL) stirred in air at room temperature, was added sodium hydride (60% dispersion in mineral oil, 23.85 mg, 0.596 mmol). The reaction mixture was stirred at 20° C. for 2 hours then carefully quenched with methanol (2 mL) and water (2 mL). The reaction mixture was evaporated in vacuo and purified by MDAP Method A, to give the desired dideuterated product, 47.5 mg, as a yellow oil. High-pH LCMS (M+1) 441, RT 1.34 mins.

Preparation of Product P174

N-(2,4-dimethylphenyl)-4-(1-hydroxy-3-(2H-tetrazol-5-yl)propyl)-N-isobutylbenzenesulfonamide a) Preparation of 5-methyl-2-trityl-2H-tetrazole To a solution of 5-methyl-1H-tetrazole (1.513 g, 18.00 mmol), tetrabutylammonium bromide (0.029 g, 0.090 mmol) and sodium hydroxide (18.90 mL, 18.90 mmol) in dichloromethane (DCM) (25 mL) stirred under nitrogen at room temperature, was added (chloromethanetriyl)tribenzene (5.02 g, 18 mmol). The reaction mixture was stirred at 20° C. for 72 hours. The reaction was quenched with water, then partitioned between dichloromethane (10 mL) and water (25 mL). The organic phase was separated (hydrophobic frit) and the aqueous phase re-extracted (stirred for 5 min) with additional DCM (10 mL), then separated with a hydrophobic frit. The combined organic fractions were washed with water (2×25 mL), 5% aqueous sodium bicarbonate (10 mL) and brine (10 mL). The organic phase was evaporated in vacuo to give a white solid. Recrystallisation from hot ethyl acetate (8 mL/g) provided the product as a white solid (2.2 g). LCMS RT 1.35 mins.

b) Preparation of N-(2,4-dimethylphenyl)-4-(1-hydroxy-3-(2-trityl-2H-tetrazol-5-yl)propyl)-N-isobutylbenzenesulfonamide To a solution of 5-methyl-2-trityl-2H-tetrazole (68.5 mg, 0.21 mmol) in tetrahydrofuran (THF) (1 mL), stirred under nitrogen at −70° C., was added a solution of n-BuLi (1.6 M in hexanes, 0.144 mL, 0.231 mmol) in Tetrahydrofuran (THF) (1 mL) dropwise over 1 minute. The reaction mixture was then stirred at −78° C. for 45 minutes. N-(2,4-dimethylphenyl)-N-isobutyl-4-(oxiran-2-yl)benzenesulfonamide (108 mg, 0.300 mmol) in Tetrahydrofuran (THF) (1 mL) was added dropwise at −78° C. over 1 minute. The reaction mixture was then stirred at −78° C. for a further 1 hour and then allowed to warm to room temperature. The reaction was carefully quenched using a few drops of water, under nitrogen. Ethyl acetae (3 mL) and water (2 mL) were added and the reaction stirred vigorously for 5 minutes. The organic phase was separated using a hydrophilic frit and concentrated in vacuo to give a residue. LCMS analysis showed incomplete reaction, so the above reaction procedure repeated using fresh n-butyl lithium solution and reintroducing the crude residue instead of new starting material, this resulted in improved conversion. The residue was then purified by flash (Si) chro- c) Preparation of N-(2,4-dimethylphenyl)-4-(1-hydroxy-3-(2H-tetrazol-5-yl)propyl)-N-isobutylbenzenesulfonamide N-(2,4-dimethylphenyl)-4-(1-hydroxy-3-(2-trityl-2H-tetrazol-5-yl)propyl)-N-isobutylbenzenesulfonamide (20 mg, 0.029 mmol), at room temperature was treated with a solution of HCl (6N in isopropanol, 2 mL, 12.00 mmol) and isopropanol (2 mL). The reaction mixture was stirred at 20° C. for 2 hours, then the solvent evaporated in vacuo and the crude partitioned between ethyl acetate (5 mL) and water (5 mL). The organic phase was separated by hydrophilic frit then evaporated in vacuo to give a residue. LCMS analysis showed the reaction was incomplete, so the residue was re-dissolved in dichloromethane (DCM) (2 mL) and treated with formic acid (0.5 mL, 13.04 mmol). The solution was left to stand for 2 hours. The solvent was evaporated in vacuo then dissolved in a 1:1 mixture of MeOH and DMSO and purified by MDAP (Method F) to give the required product, 3.69 mg. LCMS (M+1) 444, RT 1.09 mins.

Preparation of Product P175

N-(2,4-dimethylphenyl)-4-(1-hydroxy-2-(2H-tetrazol-5-yl)ethyl)-N-isobutylbenzenesulfonamide a) Preparation of N-(2,4-dimethylphenyl)-4-formyl-N-isobutylbenzenesulfonamide To a solution of (2,4-dimethylphenyl)(2-methylpropyl)amine (400 mg, 2.256 mmol) in pyridine (5 mL), stirred in air at room temperature, was added 4-formylbenzene-1-sulfonyl chloride (760 mg, 3.71 mmol) in one charge. The reaction mixture was stirred at 20° C. for 30 minutes, then left to stand 6 hours. The solvent was removed in vacuo and the crude material purified by flash (Si) chromatography (using a 0-25% ethyl acetate-cyclohexane gradient). The appropriate fractions were combined and evaporated in vacuo to give the required product (794 mg) as a colourless gum. LCMS (M+1) 346, RT 1.33 mins.

b) Preparation of N-(2,4-dimethylphenyl)-4-(1-hydroxy-2-(2H-tetrazol-5-yl)ethyl)-N-isobutylbenzenesulfonamide To a solution of 5-methyl-2-trityl-2H-tetrazole (68.5 mg, 0.21 mmol) in tetrahydrofuran (THF) (1 mL), stirred under nitrogen at −70° C., was added a solution of n-BuLi (1.6 M in hexanes, 0.144 mL, 0.231 mmol) and tetrahydrofuran (THF) (1 mL) dropwise over 1 minute. The reaction mixture was stirred at −78° C. for 45 minutes. N-(2,4-dimethylphenyl)-4-formyl-N-isobutylbenzenesulfonamide (222 mg, 0.643 mmol) in tetrahydrofuran (THF) (1 mL) was then added dropwise at −78° C. over 1 minute. The reaction mixture was stirred at −78° C. for 2 hours, then allowed to warm to room temperature. The reaction was carefully quenched using a few drops of water under nitrogen. Ethyl acetate (3 mL) and water (2 mL) were added and the reaction stirred vigorously for 5 minutes. The organic phase was separated (hydrophilic frit) then evaporated in vacuo to give a residue. The residue was redissolved in dichloromethane (DCM) (2 mL) and treated with formic acid (0.5 mL, 13.04 mmol). The solution was stood overnight, then the solvent evaporated in vacuo and the crude purified by MDAP (Method F) to give the required product, 17.3 mg. LCMS (M+1) 430, RT 1.09 mins.

Preparation of Product P176

N-(2,4-dimethylphenyl)-4-(2-hydroxy-1-(2H-tetrazol-5-yl)propan-2-yl)-N-isobutylbenzenesulfonamide a) Preparation of 4-acetyl-N-(2,4-dimethylphenyl)-N-isobutylbenzenesulfonamide To a solution of (2,4-dimethylphenyl)(2-methylpropyl)amine (300 mg, 1.692 mmol) in pyridine (5 mL), stirred in air at room temperature, was added 4-acetylbenzene-1-sulfonyl chloride (370 mg, 1.692 mmol) in one charge. The reaction mixture was stirred at 20° C. for 30 minutes, then left to stand overnight. The solvent was evaporated in vacuo then redissolved in methanol and passed through an aminopropyl (NH2) SPE cartridge, eluting with methanol, followed by 2M ammonia/methanol. The product containing fractions were combined and passed through a sulphonic acid (SCX) SPE cartridge eluting with methanol, followed by 2M ammonia/methanol. The product containing fractions were combined and evaporated under a stream of nitrogen to give the crude product. The crude was purified by flash (Si) chromatography (using a 0-50% ethyl acetate-cyclohexane gradient) to give the required product (282 mg) as a yellow gum. LCMS (M+1) 360, RT 1.35 mins.

b) Preparation of N-(2,4-dimethylphenyl)-4-(2-hydroxy-1-(2-trityl-2H-tetrazol-5-yl)propan-2-yl)-N-isobutylbenzenesulfonamide To a solution of 5-methyl-2-trityl-2H-tetrazole (68.5 mg, 0.21 mmol) in tetrahydrofuran (THF) (1 mL) stirred under nitrogen at −70° C., was added a solution of n-BuLi (1.6 M in hexanes, 0.144 mL, 0.231 mmol) and tetrahydrofuran (THF) (1 mL) dropwise over 1 minute. The reaction mixture was stirred at −78° C. for 45 minutes, then 4-acetyl-N-(2,4-dimethylphenyl)-N-isobutylbenzenesulfonamide (106 mg, 0.294 mmol) in tetrahydrofuran (THF) (1 mL) was added dropwise at −78° C. over 1 minute. The reaction mixture was stirred at −78° C. for 1 hour, then allowed to warm to room temperature. The reaction was carefully quenched using a few drops of water under nitrogen. Ethyl acetate (3 mL) and water (2 mL) were then added and the reaction stirred vigorously for 5 minutes. The organic phase was separated using a hydrophilic frit and concentrated in vacuo to give a residue. LCMS analysis showed incomplete reaction, so the above reaction procedure repeated using fresh n-butyl lithium solution and reintroducing the crude residue instead of new starting material, this resulted in improved conversion. The residue was then purified by flash silica (Si) chromatography (using a 0-25% ethyl acetate-cyclohexane gradient) to give the required product (22 mg) as a colourless gum. LCMS (M+1) 686, RT 1.57 mins.

c) Preparation of N-(2,4-dimethylphenyl)-4-(2-hydroxy-1-(2H-tetrazol-5-yl)propan-2-yl)-N-isobutylbenzenesulfonamide N-(2,4-dimethylphenyl)-4-(2-hydroxy-1-(2-trityl-2H-tetrazol-5-yl)propan-2-yl)-N-isobutylbenzenesulfonamide (22 mg, 0.032 mmol) at room temperature, was treated with a solution of HCl (6N in isopropanol, 2 mL, 12.00 mmol) and isopropanol (2 mL). The reaction mixture was stirred at 20°

C. for 2 hours then the solvent evaporated in vacuo and the crude partitioned between ethyl acetate (5 mL) and water (5 mL). The organic phase was separated by hydrophilic frit then evaporated in vacuo to give a residue. LCMS analysis showed the reaction was incomplete, so the residue was redissolved in dichloromethane (DCM) (2 mL) and treated with formic acid (0.5 mL, 13.04 mmol). The solution was left to stand for 2 hours. The solvent was evaporated in vacuo then dissolved in a 1:1 mixture of MeOH and DMSO and purified by MDAP (Method F) to give the required product, 5.3 mg. LCMS (M+1) 444, RT 1.10 mins.

Preparation of Product P177

N-(4-(1,3-dihydroxypropan-2-yl)phenyl)-4-(((3,5-dimethylisoxazol-4-yl)oxy)methyl)-N-isobutylbenzenesulfonamide a) Preparation of 2,2,3,3,9,9,10,10-octamethyl-6-(4-nitrophenyl)-4,8-dioxa-3,9-disilaundecane To a solution of 2-(4-nitrophenyl)propane-1,3-diol (120 mg, 0.609 mmol) and 1H-imidazole (83 mg, 1.217 mmol) in tetrahydrofuran (THF) (5 mL) was added tert-butylchlorodimethylsilane (220 mg, 1.461 mmol). The solution was stirred overnight at room temperature, under nitrogen. An additional 1 eq of tert-butylchlorodimethylsilane was added to the reaction and the mixture stirred, under nitrogen, over the weekend. The reaction was concentrated in vacuo and the product extracted into the organic phase of an aqueous work up between ethyl acetate and water. The organic phase was then passed through a hydrophobic frit and concentrated in vacuo to give the desired crude product, 219.6 mg, which was used directly in the next step without further purification. LCMS RT 1.84 mins.

b) Preparation of 4-(2,2,3,3,9,9,10,10-octamethyl-4,8-dioxa-3,9-disilaundecan-6-yl)aniline A solution of 2,2,3,3,9,9,10,10-octamethyl-6-(4-nitrophenyl)-4,8-dioxa-3,9-disilaundecane (219.6 mg, 0.516 mmol) was prepared in ethanol (10.32 mL). This was hydrogenated using the H-cube flow hydrogenator (settings: 20° C., 10 bar $H_2$, 1 mL/min flow rate) and a 10% Pd/C CatCart 30 catalyst. The collected solvent was evaporated by a stream nitrogen to give the desired product, 193.1 mg, which was used in the next step without purification. LCMS (M+1) 396, RT 1.72 mins.

c) Preparation of N-isobutyl-4-(2,2,3,3,9,9,10,10-octamethyl-4,8-dioxa-3,9-disilaundecan-6-yl)aniline A mixture of 4-(2,2,3,3,9,9,10,10-octamethyl-4,8-dioxa-3,9-disilaundecan-6-yl)aniline (193.1 mg, 0.488 mmol), isobutanol (0.090 mL, 0.976 mmol), potassium iodide (162 mg, 0.976 mmol), [Cp*IrCl$_2$]$_2$ (3.89 mg, 4.88 µmol) and water (3 mL) was prepared in a microwave vial. The reaction vessel was sealed and heated by microwaves to 150° C. for 1.5 hours. After cooling, the solution was diluted with water and dichloromethane (20 mL), then the organic phase separated (hydrophobic frit) and concentrated in vacuo. The crude was purified by flash silica (Si) chromatography (using a 0-100% dichloromethane-cyclohexane gradient) to give the desired product, 155.9 mg. LCMS (M+1) 452, RT 1.96 mins.

d) Preparation of 4-(((3,5-dimethylisoxazol-4-yl)oxy)methyl)-N-isobutyl-N-(4-(2,2,3,3,9,9,10,10-octamethyl-4,8-dioxa-3,9-disilaundecan-6-yl)phenyl)benzenesulfonamide A solution of 4-((3,5-dimethylisoxazol-4-yl)methoxy)benzene-1-sulfonyl chloride (125 mg, 0.414 mmol) and N-isobutyl-4-(2,2,3,3,9,9,10,10-octamethyl-4,8-dioxa-3,9-disilaundecan-6-yl)aniline (155.9 mg, 0.345 mmol) was prepared in pyridine (3 mL) and stood overnight. The solution was concentrated in vacuo and the product extracted to the organic phase of an acidic work up between ethyl acetate and 5% citric acid. The organic phase was separated (hydrophobic frit) and concentrated in vacuo to give the crude product, 214.7 mg, which was used directly in the next step with no further purification. LCMS (M+1) 717, RT 1.87 mins.

e) Preparation of N-(4-(1,3-dihydroxypropan-2-yl)phenyl)-4-(((3,5-dimethylisoxazol-4-yl)oxy)methyl)-N-isobutylbenzenesulfonamide To a solution of 4-(((3,5-dimethylisoxazol-4-yl)oxy)methyl)-N-isobutyl-N-(4-(2,2,3,3,9,9,10,10-octamethyl-4,8-dioxa-3,9-disilaundecan-6-yl)phenyl)benzenesulfonamide (214.7 mg, 0.299 mmol) in tetrahydrofuran (THF) (10 mL) was added TBAF (1 M in THF, 0.748 mL, 0.748 mmol), and this was stirred at room temperature for 1 hour. The reaction mixture was concentrated in vacuo and extracted to the organic phase of an aqueous workup between ethyl acetate and water/brine. The organic phase was separated (hydrophobic frit), then concentrated in vacuo and purified by flash silica (Si) chromatography (using a 0-100% ethyl acetate-cyclohexane gradient). The product containing fractions were combined and condensed, then freeze-dried to provide 76.4 mg of desired product. LCMS (M+1) 489, RT 1.02 mins.

Preparation of Product P178

2-(4-(N-(2,4-dimethylphenyl)-N-isobutylsulfamoyl)phenyl)acetic acid a) Preparation of methyl 2-(4-(N-(2,4-dimethylphenyl)-N-isobutylsulfamoyl)phenyl)acetate A solution of N-isobutyl-2,4-dimethylaniline (740 mg, 4.17 mmol) and methyl 2-(4-(chlorosulfonyl)phenyl)acetate (1246 mg, 5.01 mmol) was prepared in pyridine (4 mL) and stood for 2 hours. The reaction was then concentrated in vacuo and the product extracted to the organic phase of an acidic work up between ethyl acetate and 5% citric acid. The organic phase was separated (hydrophobic frit) then concentrated in vacuo and purified by flash silica (Si) chromatography (using a 0-100% dichloromethane-cyclohexane gradient) to give the desired product, 1.4199 g. LCMS (M+1) 390, RT 1.37 mins.

b) Preparation of 2-(4-(N-(2,4-dimethylphenyl)-N-isobutylsulfamoyl)phenyl)acetic acid A solution of methyl 2-(4-(N-(2,4-dimethylphenyl)-N-isobutylsulfamoyl)phenyl)acetate (1.3799 g, 3.54 mmol) in tetrahydrofuran (THF) (8 mL) and water (2 mL), was prepared and treated with sodium hydroxide (1.063 mL, 10.63 mmol). The reaction was then heated by microwaves to 110° C., for 30 minutes. After cooling, crude material from a test of the above reaction run on a smaller scale (~40 mg) was combined with this mixture. The combined solution was then neutralised with 2M HCl and diluted with further water and ethyl acetate. The product was extracted into the organic phase and the organics separated (hydrophobic frit) then concentrated in vacuo to provide 1.3033 g of desired material. LCMS (M+1) 376, RT 1.24 mins.

Preparation of Product P179

4-(N-(2,4-dimethylphenyl)-N-isobutylsulfamoyl)benzoic acid a) Preparation of methyl 4-(N-(2,4-dimethylphenyl)-N-isobutylsulfamoyl)benzoate A solution of N-isobutyl-2,4-dimethylaniline (0.63 g, 3.55 mmol) and methyl 4-(chlorosulfonyl)benzoate (1.001 g, 4.26 mmol) was prepared in pyridine (4 mL) and stood for 2 hours. The reaction was then concentrated in vacuo and the product extracted to the organic phase of an acidic work up between ethyl acetate and 5% citric acid. The organic phase was separated (hydrophobic frit) then concentrated in vacuo and purified by flash silica (Si) chromatography (using a 0-25% ethyl acetate-cyclohexane gradient) to give the desired product, 1.2698 g. LCMS (M+1) 376, RT 1.44 mins.

b) Preparation of 4-(N-(2,4-dimethylphenyl)-N-isobutylsulfamoyl)benzoic acid A solution of methyl 4-(N-(2,4-dimethylphenyl)-N-isobutylsulfamoyl)benzoate (1.2698 g, 3.38 mmol) in tetrahydrofuran (THF) (8 mL) and water (2 mL), was prepared and treated with sodium hydroxide (1.015 mL, 10.15 mmol). The reaction was then heated by microwaves to 110° C., for 30 minutes. After cooling, the solution was neutralised with 2M HCl and concentrated in vacuo. The product was extracted into the organic phase of an aqueous work up between water and ethyl acetate. The organic phase was then separated (hydrophobic frit) and concentrated in vacuo to give the desired product, 1.063 g. LCMS (M+1) 362, RT 1.27 mins.

Preparation of Product P180

4-(N-(2,4-dimethylphenyl)-N-isobutylsulfamoyl)benzoic acid, ammonia salt

N-(2,4-dimethylphenyl)-N-isobutyl-4-vinylbenzenesulfonamide (0.06 g, 0.175 mmol) was dissolved in acetone (0.240 mL) and cooled to ~2° C., with stirring. A solution of potassium permanganate (0.018 g, 0.117 mmol) and magnesium sulfate (7.00 mg, 0.058 mmol) in water (0.4 mL) was prepared and added dropwise to the acetone solution, over 20 minutes. The mixture was stirred for an additional 10 minutes, then the temperature increased to room temperature and the mixture filtered and concentrated under a stream of nitrogen. LCMS analysis confirmed presence of some acid product as well as dihydroxylated product, but showed mainly unreacted starting material. So above procedure was repeated again using this crude material, with the post-addition stirring increased to 2.75 hours at 0° C. then 15 minutes warming to rt. Analysis confirmed improved conversion, but still remaining starting material. So the procedure was repeated again using this crude material, but with the post-addition stirring increased to overnight and temperature allowed to warm from 0° C. to room temperature over this time. Analysis now confirmed all starting material had been consumed with an increased conversion to the acid product. The crude was dissolved in methanol (5 mL) and passed through an aminopropyl ($NH_2$) cartridge (washed through with methanol), however the initial flush failed to adequately separate the acid form the dihydroxylated product. A second flush of the cartridge with methanol-ammonia solution successfully eluted the desired ammonia salt of the acid product as a white solid, 9 mg. LCMS (M+1) 362, RT 1.24 mins.

Preparation of Product P181

3-(N-(2,4-dimethylphenyl)-N-isobutylsulfamoyl)benzoic acid

A solution of 3-(chlorosulfonyl)benzoic acid (439 mg, 1.992 mmol) and N-isobutyl-2,4-dimethylaniline (294 mg, 1.660 mmol) was prepared in pyridine (5 mL) and stood overnight at room temperature. An additional 0.5 eq of 3-(chlorosulfonyl)benzoic acid was then added and the reaction stood for a second night at room temperature. The solvents were then removed in vacuo and the product extracted to the organic phase of an acidic work up between ethyl acetate and 5% citric acid. The organic phase was separated (hydrophobic frit) then concentrated in vacuo and purified by flash silica (Si) chromatography (using a 0-25% ethyl acetate-cyclohexane gradient). The product containing fractions were combined and condensed to provide 99.1 mg of desired material. LCMS (M+1) 362, RT 1.24 mins.

TABLE 5

| Chemical Structures of A References | |
|---|---|
| ID | Structure |
| A1 | $NH_2$ |
| A2 | Cl |
| A3 | $NH_2$ |
| A4 | $NH_2$ |

TABLE 5-continued

Chemical Structures of A References

| ID | Structure |
|---|---|
| A5 | 4-chloroaniline |
| A6 | 2-fluoro-4-methylaniline |
| A7 | 2,4-difluoroaniline |
| A8 | 4-butylaniline |
| A9 | 4-isopropylaniline |
| A10 | 3-(trifluoromethyl)aniline |
| A11 | 4-propylaniline |
| A12 | 2-methyl-5-(trifluoromethyl)aniline |
| A13 | 3-methylaniline |
| A14 | 2-chloro-5-fluoroaniline |
| A15 | 5-chloro-2-fluoroaniline |
| A16 | 3-methoxyaniline |
| A17 | 3-ethylaniline |
| A18 | 4-methylaniline |
| A19 | 4-chloro-3-methylphenol |

TABLE 5-continued

Chemical Structures of A References

| ID | Structure |
|---|---|
| A20 | 4-aminophenyl-(3-((tert-butyldimethylsilyl)oxy)propyl) |
| A21 | N-isobutylaniline |
| A22 | 2-ethyl-N-propylaniline |
| A23 | N-propylaniline |
| A24 | 3,5-difluoroaniline |
| A25 | 2,5-difluoroaniline |
| A26 | 3,5-dichloroaniline |
| A27 | 2,5-dichloroaniline |
| A28 | 3,4-dichloroaniline |
| A29 | 3,4-dimethylaniline |
| A30 | 3-fluoro-5-methylaniline |
| A31 | 5-methoxy-2-methylaniline |
| A32 | 5-fluoro-2-methylaniline |
| A33 | 3-chloroaniline |
| A34 | 2,5-dimethylaniline |
| A35 | 5-isopropyl-2-methylaniline |
| A36 | 2-methylaniline |

TABLE 5-continued

Chemical Structures of A References

| ID | Structure |
|---|---|
| A37 | 4-bromo-2-methylaniline |
| A38 | 4-(cyclopropylmethyl)-2,6-dimethylaniline |
| A39 | ethyl 4-amino-3-methylbenzoate |

TABLE 6

Chemical Structures of B References

| ID | Structure |
|---|---|
| B1 | isobutyraldehyde |
| B2 | isobutylamine |
| B3 | isobutanol |
| B4 | isobutyric anhydride |
| B5 | diisobutylamine |

TABLE 6-continued

Chemical Structures of B References

| ID | Structure |
|---|---|
| B6 | cyclopropylmethanol |
| B7 | 4-(pyridin-4-yloxy)benzenesulfonyl chloride |
| B8 | 4-((3,5-dimethylisoxazol-4-yl)methoxy)benzenesulfonyl chloride |
| B9 | 4-(benzyloxy)benzenesulfonyl chloride |
| B11 | 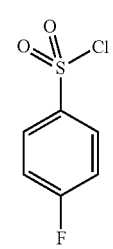 4-fluorobenzenesulfonyl chloride |

TABLE 6-continued
Chemical Structures of B References
| ID | Structure |
|---|---|
| B12 | 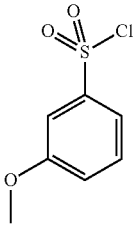 |
| B13 | 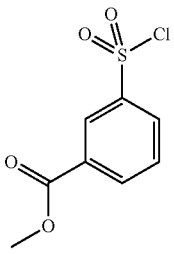 |
| B14 | 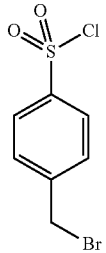 |
| B15 | 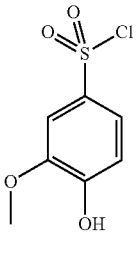 |
| B16 | 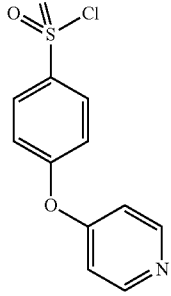 |
| B17 | 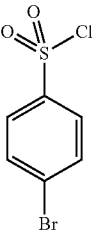 |
| B18 | 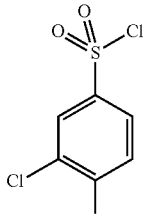 |
| B19 | 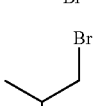 |
| B20 | 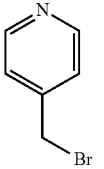 |
| B21 | 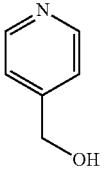 |
| B22 | 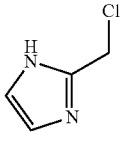 |
| B23 | 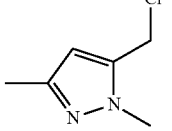 |
| B24 | 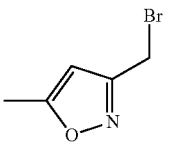 |
| B25 | 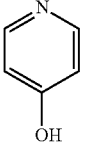 |
| B26 | 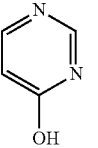 |

TABLE 6-continued

Chemical Structures of B References

| ID | Structure |
|----|-----------|
| B27 | 5-methyl-3-methylisoxazole-4-methanol |
| B28 | 4-(bromomethyl)pyridine HBr |
| B29 | (4-methyl-1H-imidazol-5-yl)methanol |
| B30 | (1-methyl-1H-1,2,4-triazol-3-yl)methanol |
| B31 | (1-methyl-1H-imidazol-2-yl)methanol |
| B32 | (1H-imidazol-4-yl)methanol |
| B33 | pyrimidin-4-ylmethanol |
| B34 | 2-(pyridin-4-yl)ethanol |
| B35 | 2-(3,5-dimethylisoxazol-4-yl)ethanol |

TABLE 6-continued

Chemical Structures of B References

| ID | Structure |
|----|-----------|
| B36 | (2-fluoropyridin-4-yl)methanol |
| B37 | (1-methyl-1H-imidazol-5-yl)methanol |
| B38 | (1-methyl-1H-1,2,4-triazol-5-yl)methanol |
| B39 | 4-(chloromethyl)-3,5-dimethylisoxazole |
| B40 | (2-aminopyridin-4-yl)methanol |

TABLE 7

Chemical Structures of Products (P)

| ID | Structure |
|----|-----------|
| P1a-d | N-isobutyl-2,4-dimethylaniline |
| P2a-c | 4-butyl-N-isobutyl-2-methylaniline |
| P3 | 4-fluoro-N-isobutyl-2-methylaniline |

TABLE 7-continued
Chemical Structures of Products (P)
| ID | Structure |
|---|---|
| P4 | 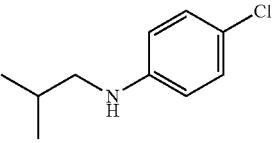 |
| P5 | 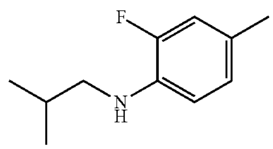 |
| P6 | 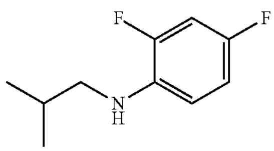 |
| P7 | 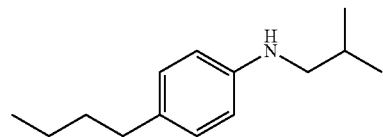 |
| P8 | 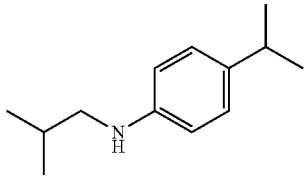 |
| P9 | 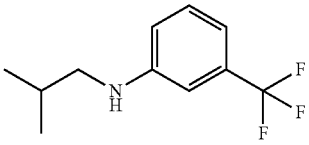 |
| P10 | 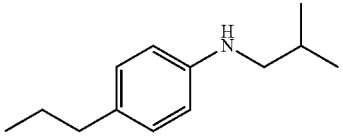 |
| P11 | 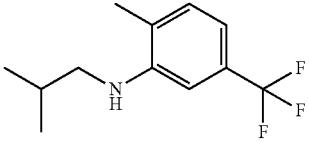 [SMILES: Cc1ccc(C(F)(F)F)cc1NCC(C)C] |
| P12 | 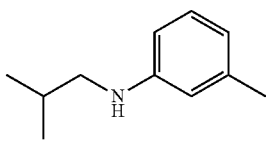 |
| P13 | 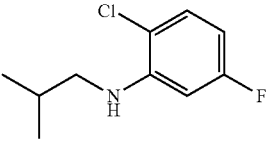 |
| P14 | 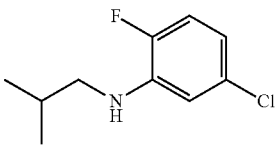 |
| P15 | 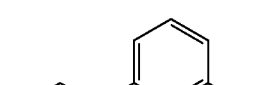 |
| P16 | 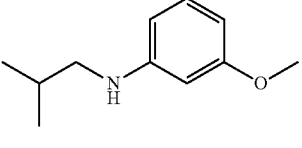 |
| P17 | 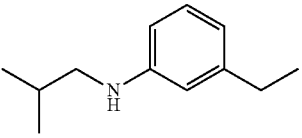 |
| P18 | 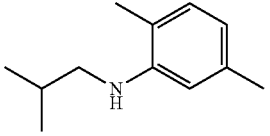 |
| P19 | 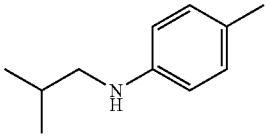 |
| P20 | 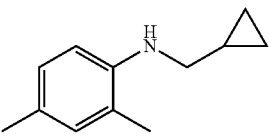 |
| P21 | 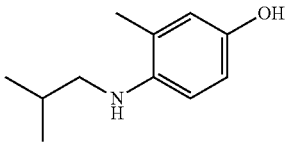 |

TABLE 7-continued

Chemical Structures of Products (P)

| ID | Structure |
|----|-----------|
| P22 | 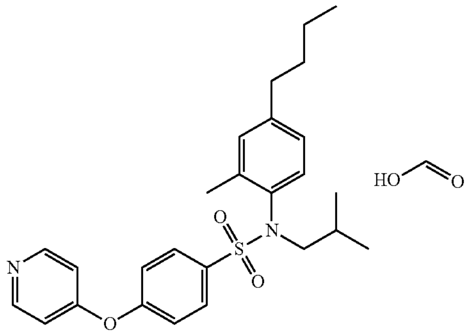 [SMILES: CCCCc1ccc(N(CC(C)C)S(=O)(=O)c2ccc(Oc3ccncc3)cc2)c(C)c1 ; O=CO] |
| P23 | 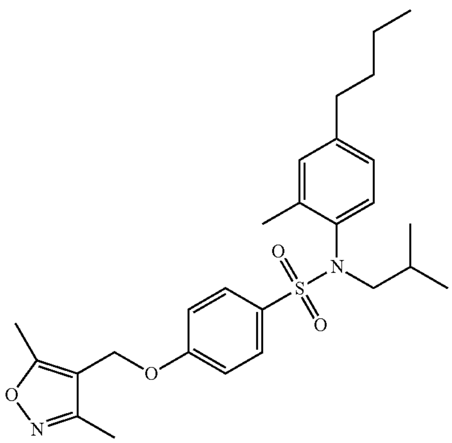 [SMILES: CCCCc1ccc(N(CC(C)C)S(=O)(=O)c2ccc(OCc3c(C)noc3C)cc2)c(C)c1] |
| P24 | 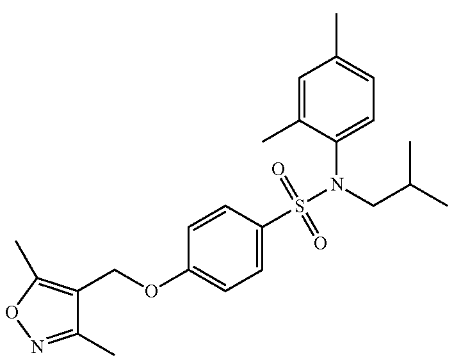 [SMILES: Cc1ccc(N(CC(C)C)S(=O)(=O)c2ccc(OCc3c(C)noc3C)cc2)c(C)c1] |
| P25 | 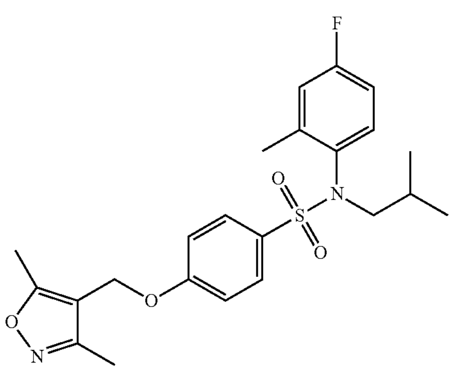 [SMILES: Cc1cc(F)ccc1N(CC(C)C)S(=O)(=O)c1ccc(OCc2c(C)noc2C)cc1] |
| P26 | |
| P27 | |
| P28 | |
| P29 | |

TABLE 7-continued

Chemical Structures of Products (P)

| ID | Structure |
|---|---|
| P30 | (4-chlorophenyl)-N-isobutyl sulfonamide with 3,5-dimethylisoxazol-4-ylmethoxyphenyl group |
| P31 | (4-propylphenyl)-N-isobutyl sulfonamide with 3,5-dimethylisoxazol-4-ylmethoxyphenyl group |
| P32 | (3-trifluoromethylphenyl)-N-isobutyl sulfonamide with 3,5-dimethylisoxazol-4-ylmethoxyphenyl group |
| P33 | (2-methyl-4-trifluoromethylphenyl)-N-isobutyl sulfonamide with 3,5-dimethylisoxazol-4-ylmethoxyphenyl group |
| P34 | phenyl-N-isobutyl sulfonamide with 3,5-dimethylisoxazol-4-ylmethoxyphenyl group |
| P35 | (2-ethylphenyl)-N-propyl sulfonamide with 3,5-dimethylisoxazol-4-ylmethoxyphenyl group |
| P36 | (3-methylphenyl)-N-isobutyl sulfonamide with 3,5-dimethylisoxazol-4-ylmethoxyphenyl group |
| P37 | (2,5-dimethylphenyl)-N-isobutyl sulfonamide with 3,5-dimethylisoxazol-4-ylmethoxyphenyl group |

TABLE 7-continued
Chemical Structures of Products (P)
| ID | Structure |
|---|---|
| P38 | 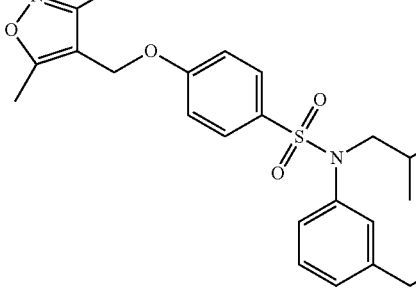 |
| P39 | 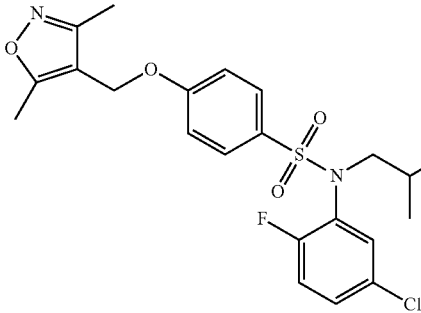 |
| P40 | 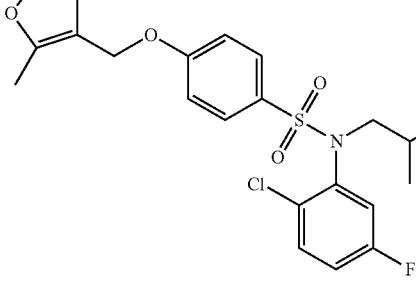 |
| P41 | 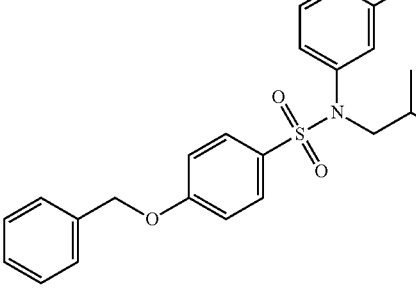 |
| P42 | 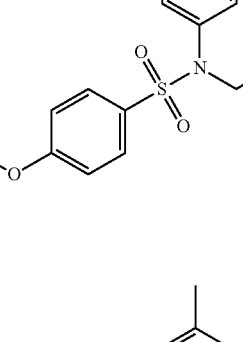 |
| P43 | 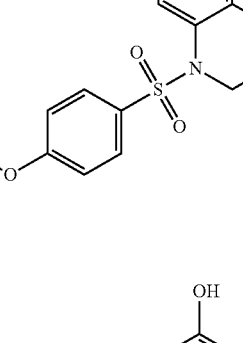 |
| P44 | 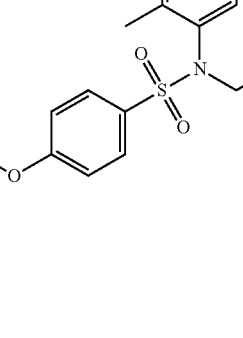 |
| P45 | 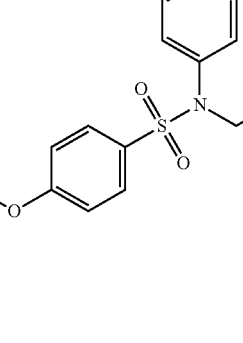 |

TABLE 7-continued

Chemical Structures of Products (P)

| ID | Structure |
|----|-----------|
| P46 | |
| P47 | |
| P48 | |
| P49 | |
| P50 | |
| P51 | |
| P52 | 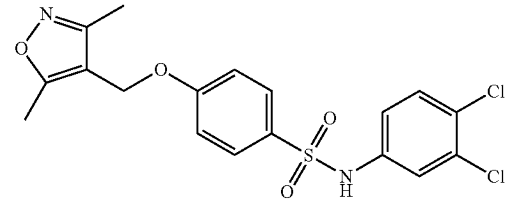 [SMILES: Cc1noc(C)c1COc1ccc(S(=O)(=O)Nc2ccc(Cl)c(Cl)c2)cc1] |
| P53 | 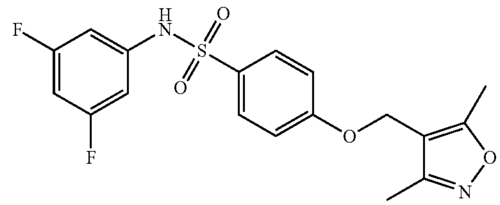 [SMILES: Cc1noc(C)c1COc1ccc(S(=O)(=O)Nc2cc(F)cc(F)c2)cc1] |
| P54 | 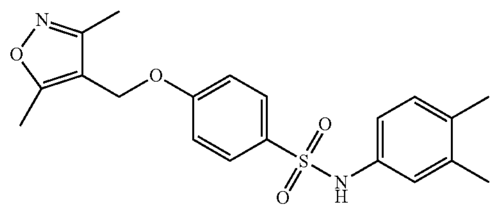 [SMILES: Cc1ccc(NS(=O)(=O)c2ccc(OCc3c(C)noc3C)cc2)cc1C] |
| P55 | 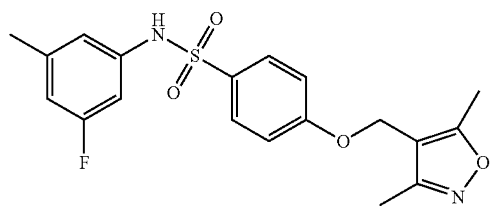 [SMILES: Cc1cc(F)cc(NS(=O)(=O)c2ccc(OCc3c(C)noc3C)cc2)c1] |
| P56 | 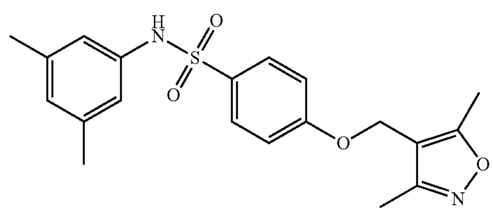 [SMILES: Cc1cc(C)cc(NS(=O)(=O)c2ccc(OCc3c(C)noc3C)cc2)c1] |
| P57 | 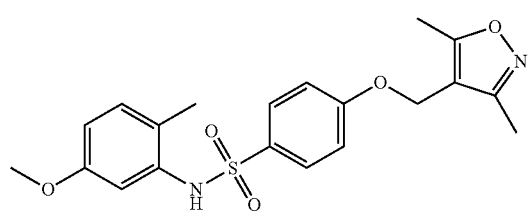 [SMILES: COc1ccc(C)c(NS(=O)(=O)c2ccc(OCc3c(C)noc3C)cc2)c1] |
| P58 | 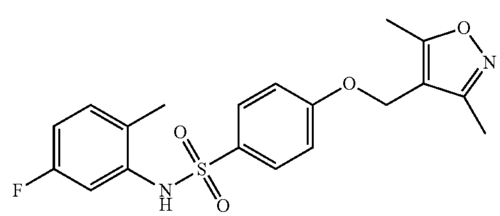 [SMILES: Cc1ccc(F)cc1NS(=O)(=O)c1ccc(OCc2c(C)noc2C)cc1] |

TABLE 7-continued

Chemical Structures of Products (P)

| ID | Structure |
|---|---|
| P59 | |
| P60 | |
| P61 | |
| P62 | |
| P63 | |
| P64 | |
| P65 | 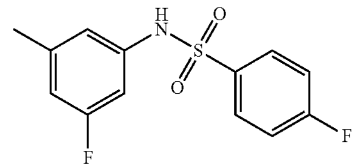 [SMILES: Cc1cc(F)cc(NS(=O)(=O)c2ccc(F)cc2)c1] |
| P66 | 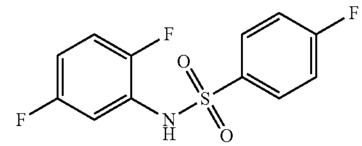 [SMILES: O=S(=O)(Nc1cc(F)ccc1F)c1ccc(F)cc1] |
| P67 | 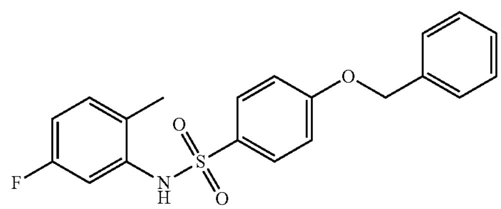 [SMILES: Cc1ccc(F)cc1NS(=O)(=O)c1ccc(OCc2ccccc2)cc1] |
| P68 | 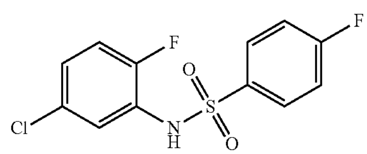 [SMILES: O=S(=O)(Nc1cc(Cl)ccc1F)c1ccc(F)cc1] |
| P69 | 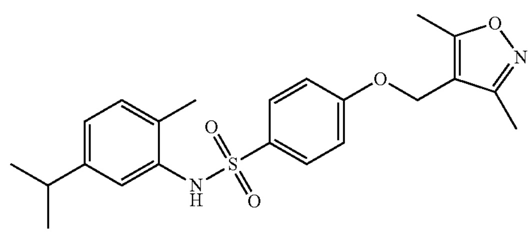 [SMILES: Cc1ccc(C(C)C)cc1NS(=O)(=O)c1ccc(OCc2c(C)noc2C)cc1] |
| P70 | 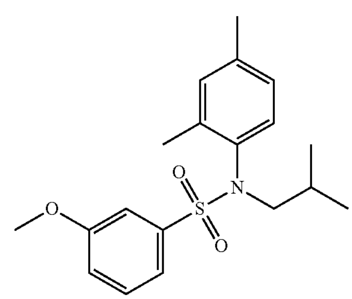 [SMILES: COc1cccc(S(=O)(=O)N(CC(C)C)c2ccc(C)cc2C)c1] |
| P71 | 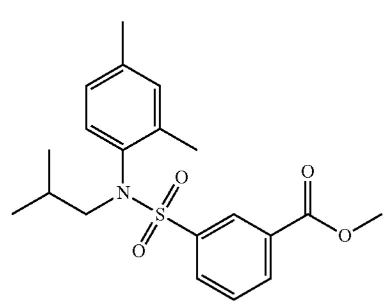 [SMILES: COC(=O)c1cccc(S(=O)(=O)N(CC(C)C)c2ccc(C)cc2C)c1] |

TABLE 7-continued
Chemical Structures of Products (P)
| ID | Structure |
|----|-----------|
| P72 | 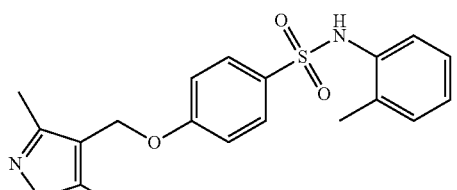 |
| P73 | 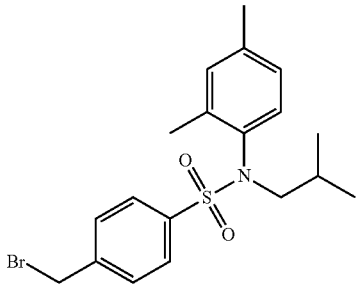 [SMILES: Cc1ccc(N(CC(C)C)S(=O)(=O)c2ccc(CBr)cc2)c(C)c1] |
| P74 | 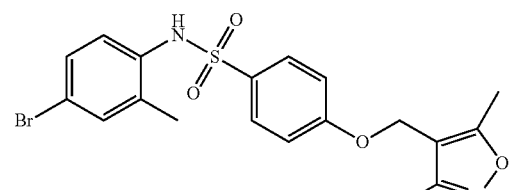 |
| P75 | 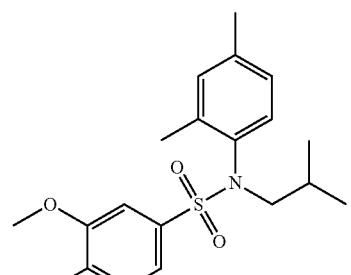 |
| P76 | 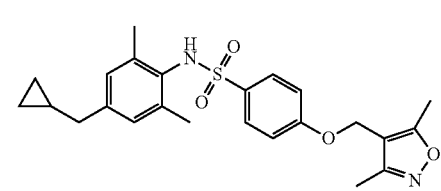 [SMILES: Cc1cc(CC2CC2)cc(C)c1NS(=O)(=O)c1ccc(OCc2c(C)noc2C)cc1] |
| P77 | 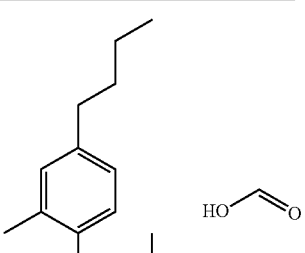 |
| P78 | 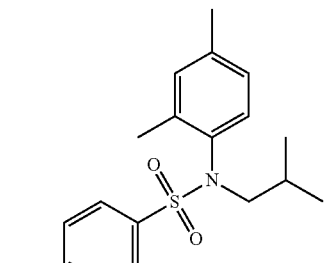 |
| P79 | 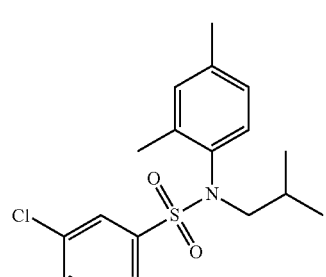 |
| P80 |  |

TABLE 7-continued

Chemical Structures of Products (P)

| ID | Structure |
|---|---|
| P81 | 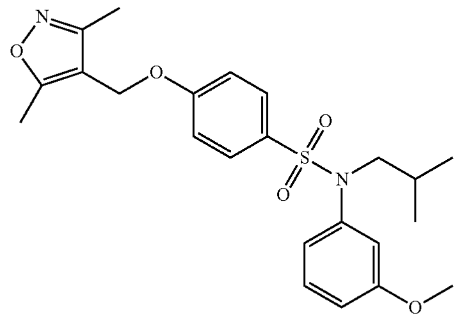 [SMILES: COc1cccc(N(CC(C)C)S(=O)(=O)c2ccc(OCc3c(C)noc3C)cc2)c1] |
| P82 | 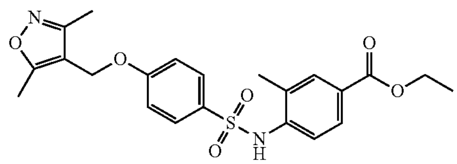 [SMILES: CCOC(=O)c1ccc(NS(=O)(=O)c2ccc(OCc3c(C)noc3C)cc2)c(C)c1] |
| P83 | 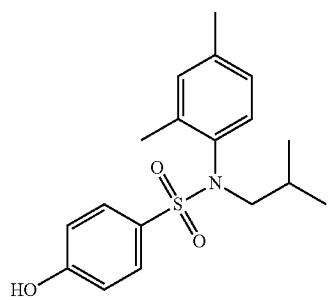 [SMILES: Cc1ccc(N(CC(C)C)S(=O)(=O)c2ccc(O)cc2)c(C)c1] |
| P84 | 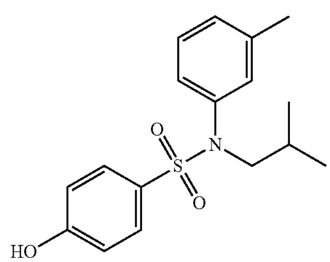 [SMILES: Cc1cccc(N(CC(C)C)S(=O)(=O)c2ccc(O)cc2)c1] |
| P85 | 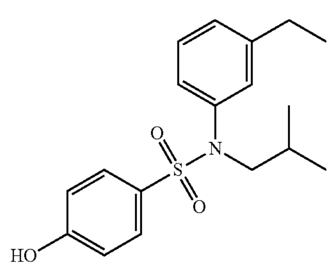 [SMILES: CCc1cccc(N(CC(C)C)S(=O)(=O)c2ccc(O)cc2)c1] |
| P86 | 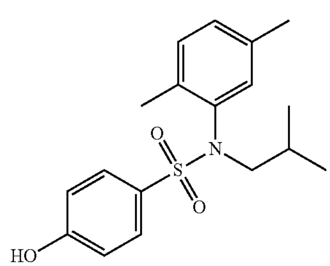 [SMILES: Cc1ccc(C)c(N(CC(C)C)S(=O)(=O)c2ccc(O)cc2)c1] |
| P87 | 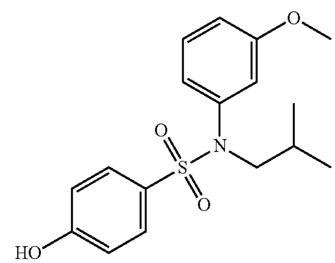 [SMILES: COc1cccc(N(CC(C)C)S(=O)(=O)c2ccc(O)cc2)c1] |
| P88 | 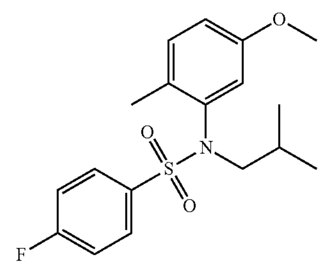 [SMILES: COc1ccc(C)c(N(CC(C)C)S(=O)(=O)c2ccc(F)cc2)c1] |
| P89 | 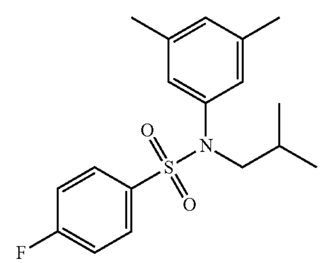 [SMILES: Cc1cc(C)cc(N(CC(C)C)S(=O)(=O)c2ccc(F)cc2)c1] |
| P90 | 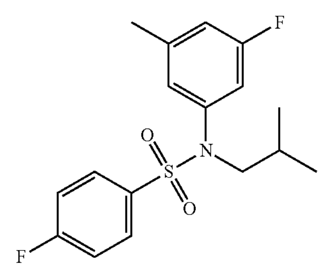 [SMILES: Cc1cc(F)cc(N(CC(C)C)S(=O)(=O)c2ccc(F)cc2)c1] |
| P91 | 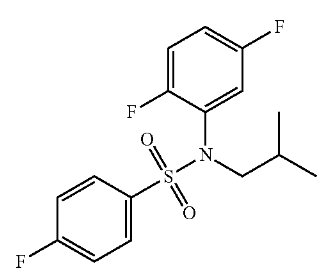 [SMILES: CC(C)CN(c1cc(F)ccc1F)S(=O)(=O)c1ccc(F)cc1] |

TABLE 7-continued

Chemical Structures of Products (P)

| ID | Structure |
|----|-----------|
| P92 | 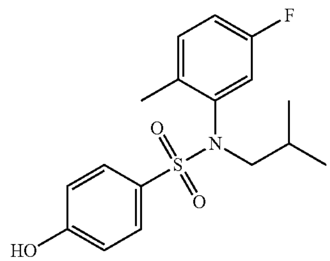 [SMILES: Cc1ccc(F)cc1N(CC(C)C)S(=O)(=O)c1ccc(O)cc1] |
| P93 | 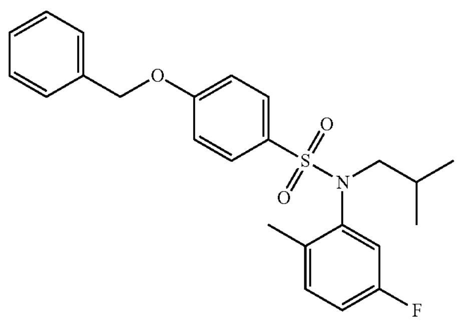 [SMILES: Cc1ccc(F)cc1N(CC(C)C)S(=O)(=O)c1ccc(OCc2ccccc2)cc1] |
| P94 | 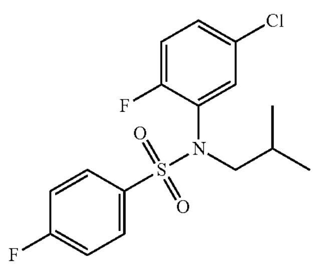 [SMILES: CC(C)CN(c1cc(Cl)ccc1F)S(=O)(=O)c1ccc(F)cc1] |
| P95 | 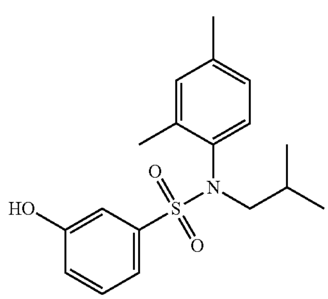 [SMILES: Cc1ccc(N(CC(C)C)S(=O)(=O)c2cccc(O)c2)c(C)c1] |
| P96 | 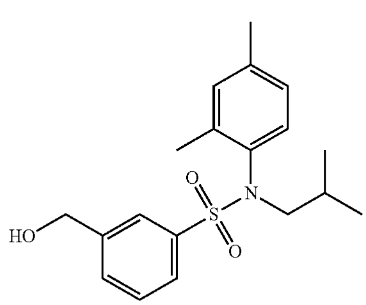 [SMILES: Cc1ccc(N(CC(C)C)S(=O)(=O)c2cccc(CO)c2)c(C)c1] |
| P97 | |
| P98 | |
| P99 | |
| P100 | |

TABLE 7-continued
Chemical Structures of Products (P)
| ID | Structure |
|---|---|
| P101 | 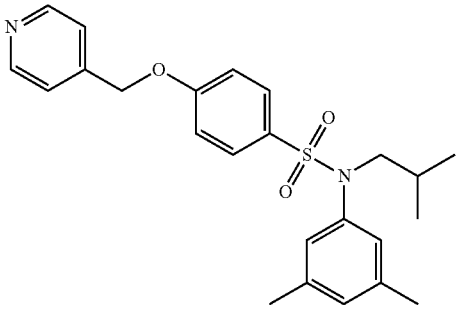 [SMILES: Cc1cc(C)cc(N(CC(C)C)S(=O)(=O)c2ccc(OCc3ccncc3)cc2)c1] |
| P102 | 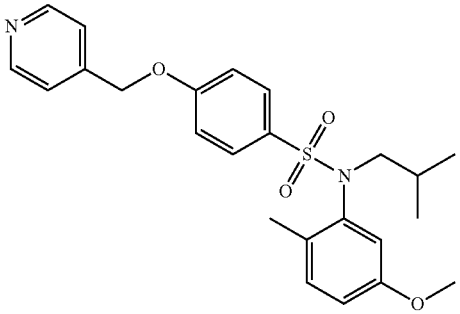 [SMILES: COc1ccc(C)c(N(CC(C)C)S(=O)(=O)c2ccc(OCc3ccncc3)cc2)c1] |
| P103 | 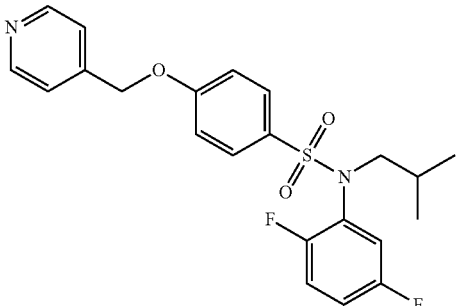 [SMILES: Cc1ccc(C)c(N(CC(C)C)S(=O)(=O)c2ccc(OCc3ccncc3)cc2)c1] |
| P104 | 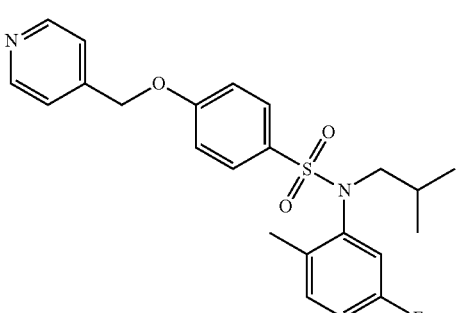 |
| P105 | 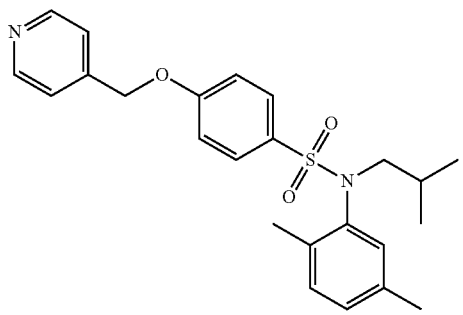 |
| P106 | 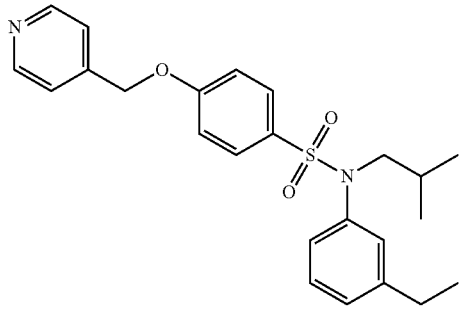 [SMILES: CCc1cccc(N(CC(C)C)S(=O)(=O)c2ccc(OCc3ccncc3)cc2)c1] |
| P107 | 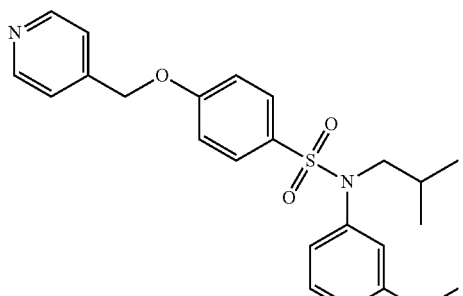 |
| P108 | 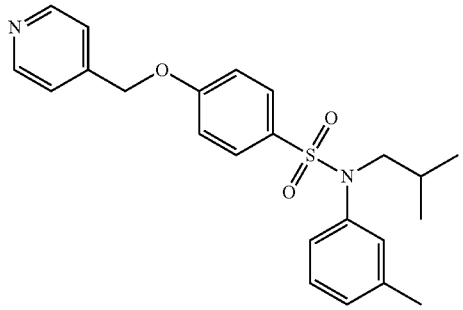 [SMILES: Cc1cccc(N(CC(C)C)S(=O)(=O)c2ccc(OCc3ccncc3)cc2)c1] |

TABLE 7-continued

Chemical Structures of Products (P)

| ID | Structure |
|---|---|
| P109 | 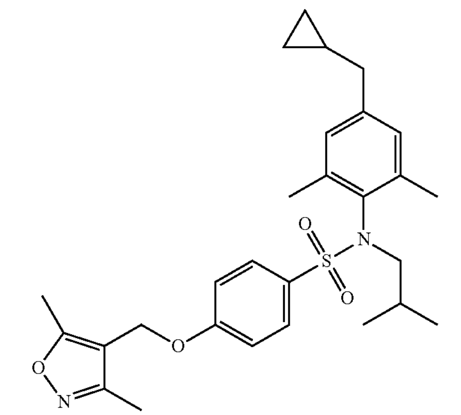 [SMILES: Cc1cc(CC2CC2)cc(C)c1N(CC(C)C)S(=O)(=O)c1ccc(OCc2c(C)noc2C)cc1] |
| P110 | 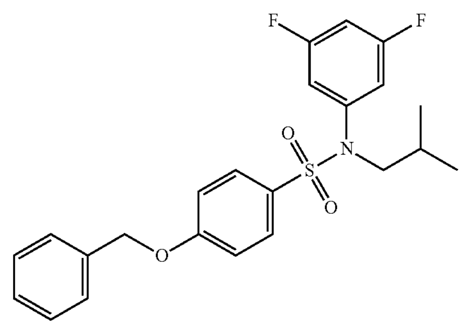 [SMILES: CC(C)CN(c1cc(F)cc(F)c1)S(=O)(=O)c1ccc(OCc2ccccc2)cc1] |
| P111 | 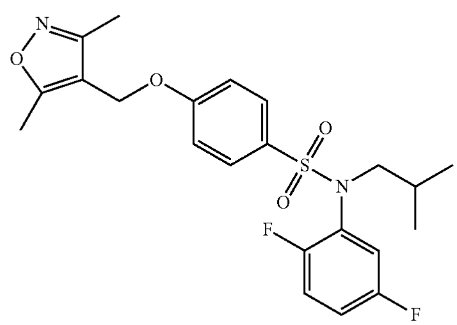 [SMILES: Cc1noc(C)c1COc1ccc(S(=O)(=O)N(CC(C)C)c2cc(F)ccc2F)cc1] |
| P112 | 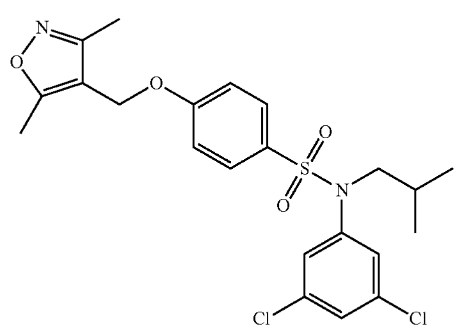 [SMILES: Cc1noc(C)c1COc1ccc(S(=O)(=O)N(CC(C)C)c2cc(Cl)cc(Cl)c2)cc1] |
| P113 | |
| P114 | |
| P115 | |
| P116 | |

TABLE 7-continued
Chemical Structures of Products (P)
| ID | Structure |
|---|---|
| P117 | 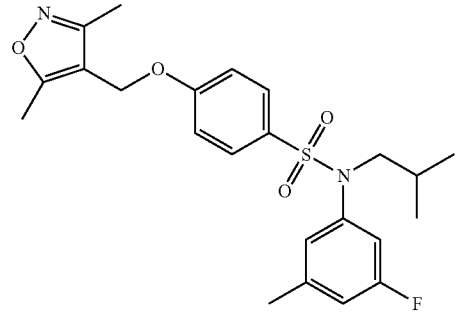 [SMILES: Cc1cc(F)cc(N(CC(C)C)S(=O)(=O)c2ccc(OCc3c(C)noc3C)cc2)c1] |
| P118 | 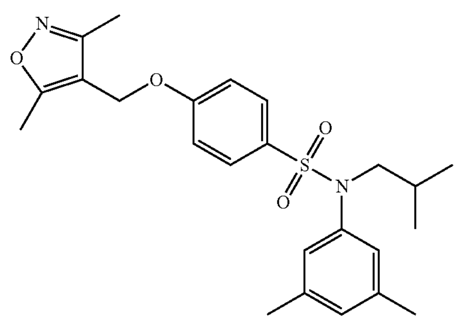 [SMILES: Cc1cc(C)cc(N(CC(C)C)S(=O)(=O)c2ccc(OCc3c(C)noc3C)cc2)c1] |
| P119 | 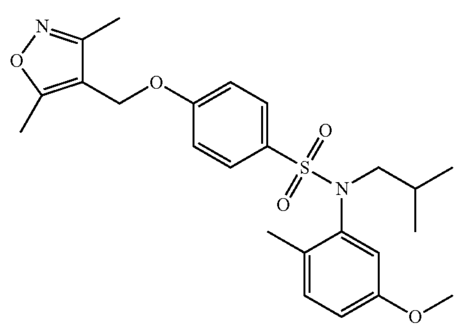 [SMILES: COc1ccc(C)c(N(CC(C)C)S(=O)(=O)c2ccc(OCc3c(C)noc3C)cc2)c1] |
| P120 | 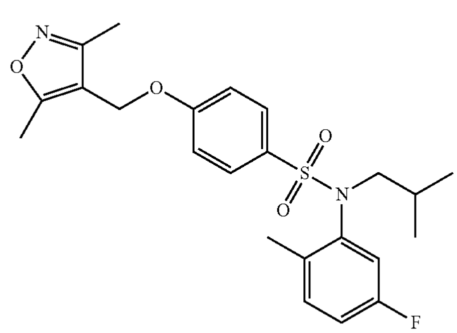 [SMILES: Cc1ccc(F)cc1N(CC(C)C)S(=O)(=O)c1ccc(OCc2c(C)noc2C)cc1] |
| P121 | 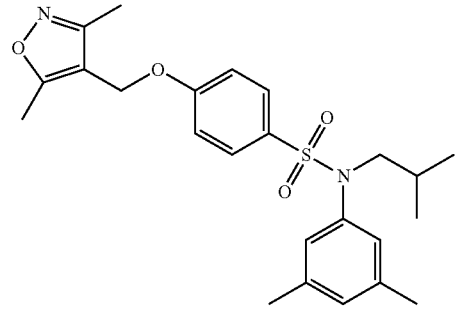 |
| P122 | |
| P123 | 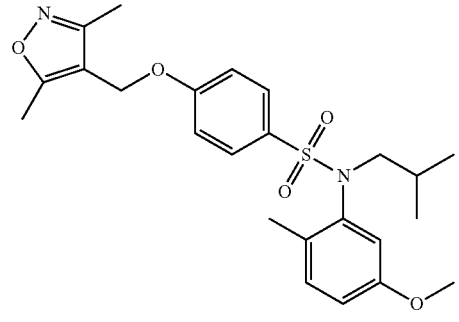 |
| P124 | 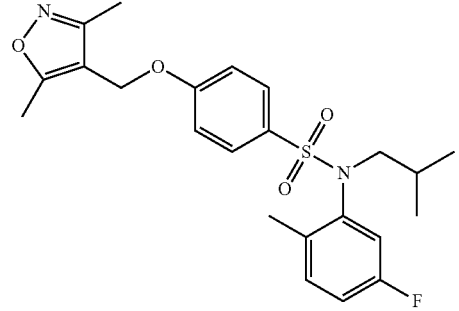 |

TABLE 7-continued
Chemical Structures of Products (P)
| ID | Structure |
|---|---|
| P125 | 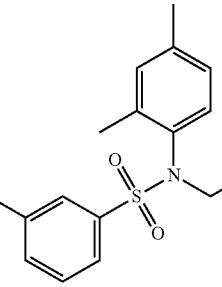 |
| P126 | 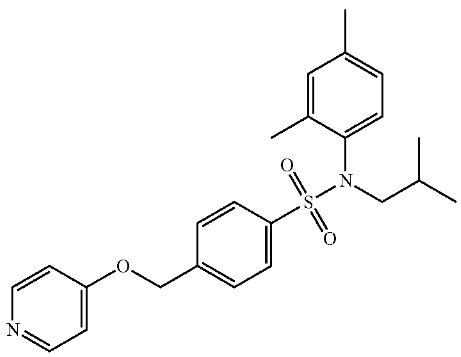 |
| P127 | 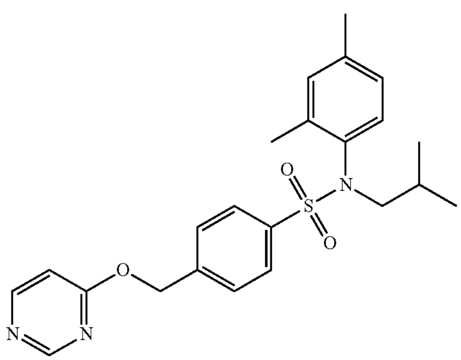 [SMILES: Cc1ccc(N(CC(C)C)S(=O)(=O)c2ccc(COc3ccncn3)cc2)c(C)c1] |
| P128 | 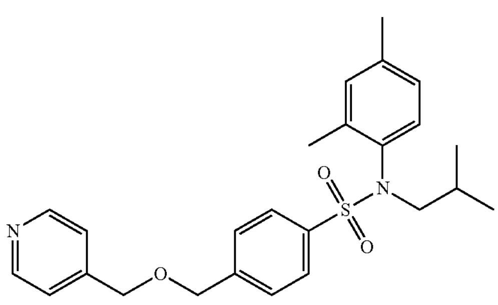 [SMILES: Cc1ccc(N(CC(C)C)S(=O)(=O)c2ccc(COCc3ccncc3)cc2)c(C)c1] |
TABLE 7-continued
Chemical Structures of Products (P)
| ID | Structure |
|---|---|
| P129 | 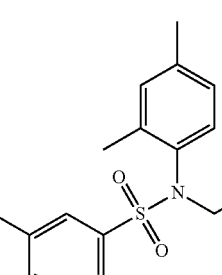 |
| P130 | 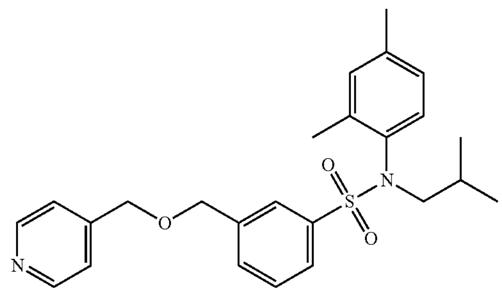 |
| P131 | 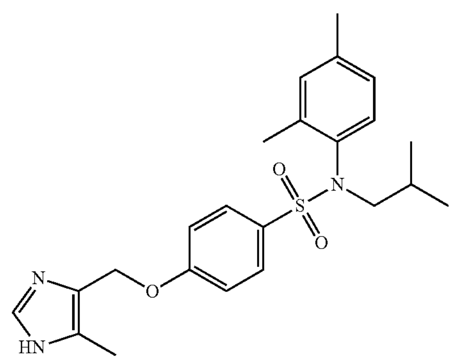 [SMILES: Cc1ccc(N(CC(C)C)S(=O)(=O)c2ccc(OCc3nc[nH]c3C)cc2)c(C)c1] |
| P132 | 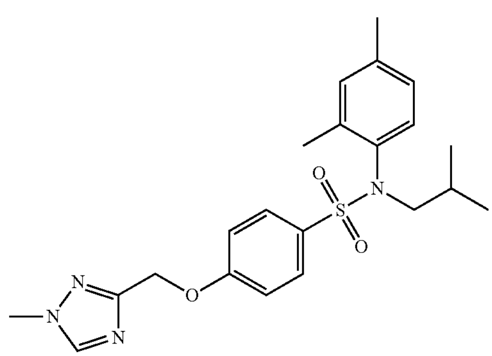 [SMILES: Cc1ccc(N(CC(C)C)S(=O)(=O)c2ccc(OCc3ncn(C)n3)cc2)c(C)c1] |

TABLE 7-continued

Chemical Structures of Products (P)

| ID | Structure |
|---|---|
| P133 | |
| P134 | |
| P135 | |
| P136 | |
| P137 | 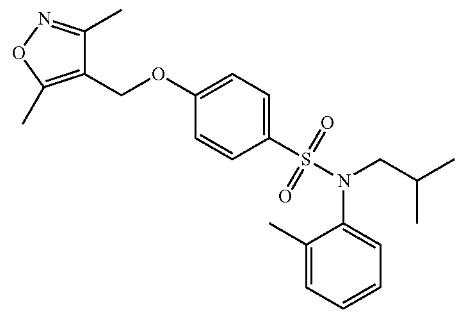 [SMILES: Cc1ccccc1N(CC(C)C)S(=O)(=O)c1ccc(OCc2c(C)noc2C)cc1] |
| P138 | 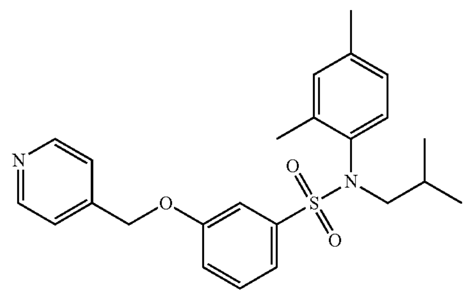 [SMILES: Cc1ccc(N(CC(C)C)S(=O)(=O)c2cccc(OCc3ccncc3)c2)c(C)c1] |
| P139 | 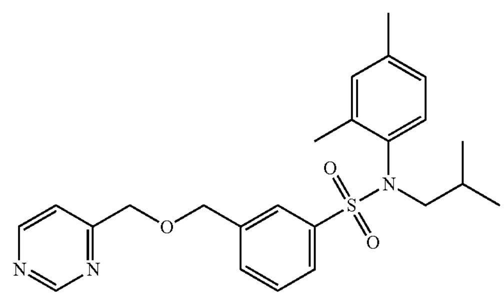 [SMILES: Cc1ccc(N(CC(C)C)S(=O)(=O)c2cccc(COCc3ccncn3)c2)c(C)c1] |
| P140 | 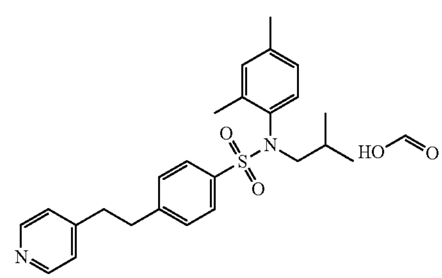 |
| P141 | 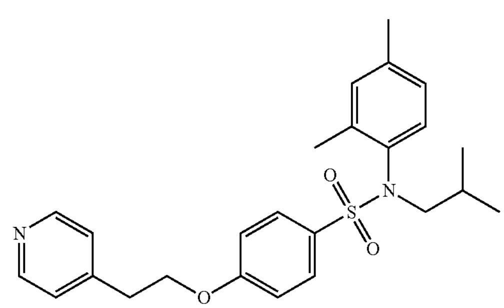 [SMILES: Cc1ccc(N(CC(C)C)S(=O)(=O)c2ccc(OCCc3ccncc3)cc2)c(C)c1] |

TABLE 7-continued
Chemical Structures of Products (P)
| ID | Structure |
|---|---|
| P142 | 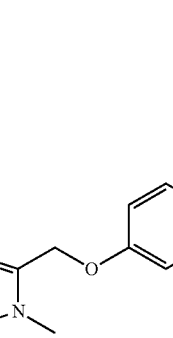 |
| P143 | 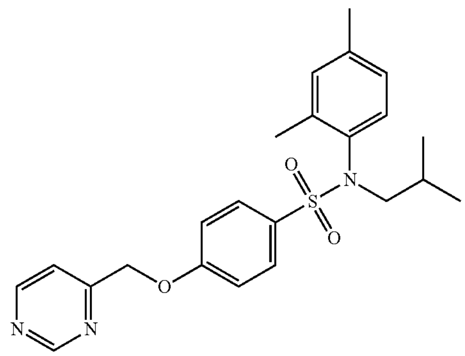 [SMILES: Cc1ccc(N(CC(C)C)S(=O)(=O)c2ccc(OCc3ccncn3)cc2)c(C)c1] |
| P144 | 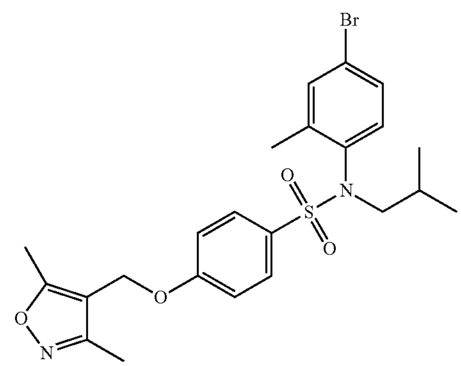 [SMILES: Cc1cc(Br)ccc1N(CC(C)C)S(=O)(=O)c1ccc(OCc2c(C)noc2C)cc1] |
| P145 | 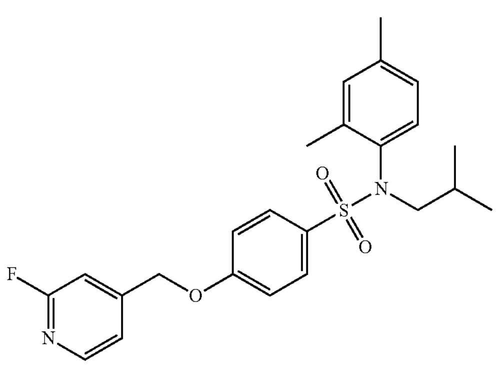 [SMILES: Cc1ccc(N(CC(C)C)S(=O)(=O)c2ccc(OCc3ccnc(F)c3)cc2)c(C)c1] |
| P146 |  |
| P147 | |
| P148 | |
| P149 | |

TABLE 7-continued
Chemical Structures of Products (P)
| ID | Structure |
|---|---|
| P150 | 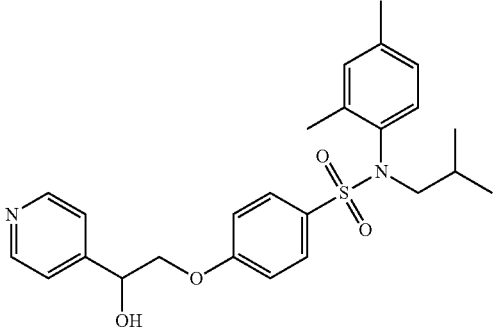 [SMILES: Cc1ccc(N(CC(C)C)S(=O)(=O)c2ccc(OCC(O)c3ccncc3)cc2)c(C)c1] |
| P151 | 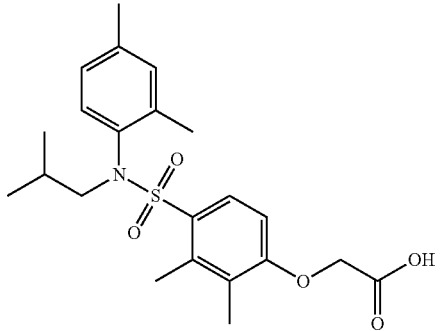 [SMILES: Cc1ccc(N(CC(C)C)S(=O)(=O)c2ccc(OCC(=O)O)c(C)c2C)c(C)c1] |
| P152 | 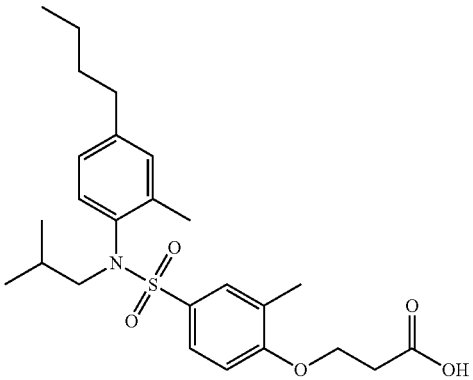 [SMILES: CCCCc1ccc(N(CC(C)C)S(=O)(=O)c2ccc(OCCC(=O)O)c(C)c2)c(C)c1] |
| P153 | 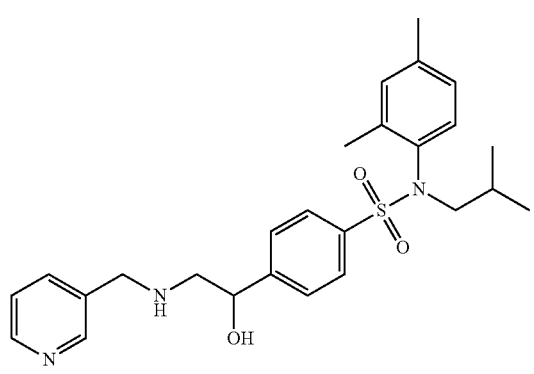 [SMILES: Cc1ccc(N(CC(C)C)S(=O)(=O)c2ccc(C(O)CNCc3cccnc3)cc2)c(C)c1] |
| P154 | 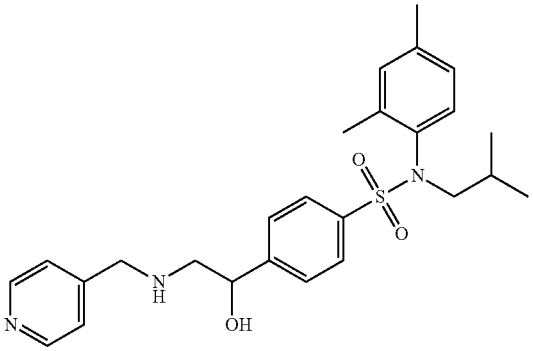 [SMILES: Cc1ccc(N(CC(C)C)S(=O)(=O)c2ccc(C(O)CNCc3ccncc3)cc2)c(C)c1] |
| P155 | 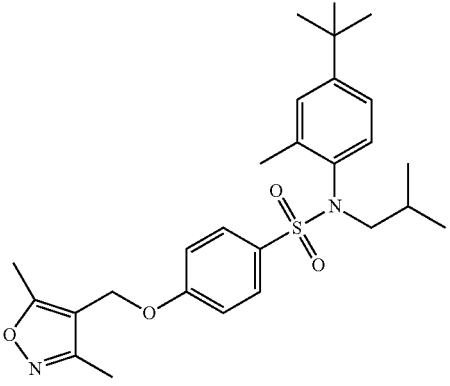 |
| P156 | 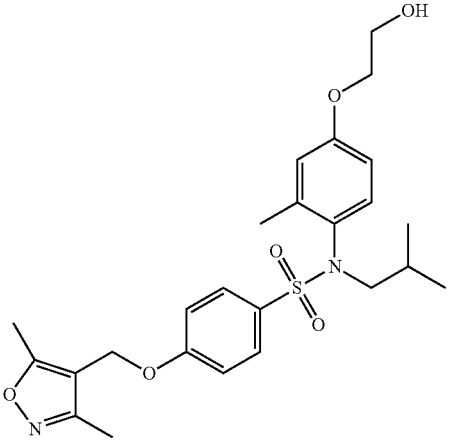 [SMILES: Cc1cc(OCCO)ccc1N(CC(C)C)S(=O)(=O)c1ccc(OCc2c(C)noc2C)cc1] |

TABLE 7-continued

Chemical Structures of Products (P)

| ID | Structure |
|---|---|
| P157 | 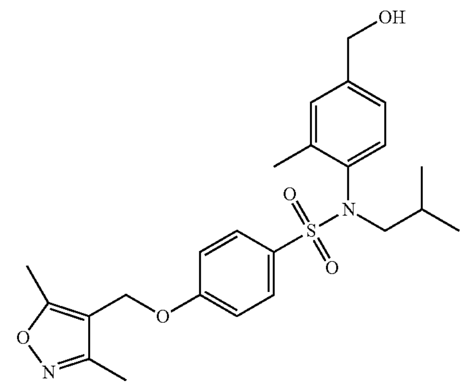 [SMILES: Cc1cc(CO)ccc1N(CC(C)C)S(=O)(=O)c1ccc(OCc2c(C)noc2C)cc1] |
| P158 | 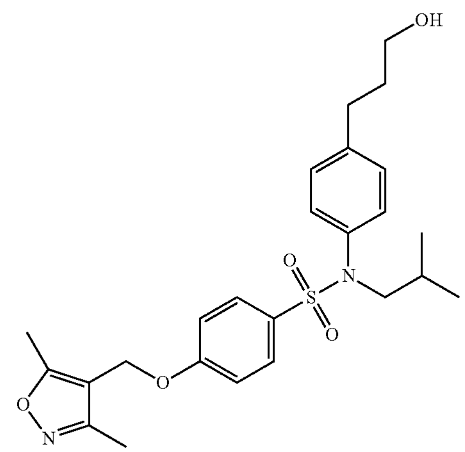 [SMILES: Cc1noc(C)c1COc1ccc(S(=O)(=O)N(CC(C)C)c2ccc(CCCO)cc2)cc1] |
| P159 | 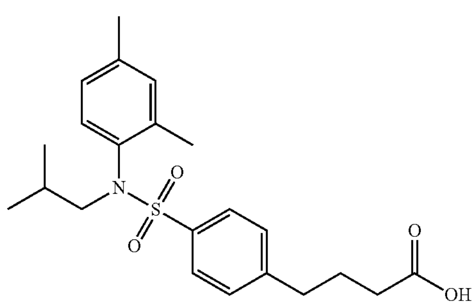 [SMILES: Cc1ccc(N(CC(C)C)S(=O)(=O)c2ccc(CCCC(=O)O)cc2)c(C)c1] |
| P160 | 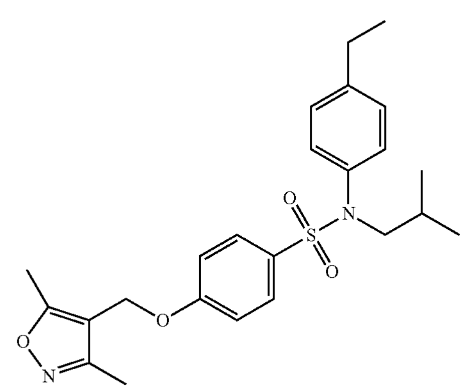 [SMILES: CCc1ccc(N(CC(C)C)S(=O)(=O)c2ccc(OCc3c(C)noc3C)cc2)cc1] |
| P161 | |
| P162 | |
| P163 | |
| P164 | |

TABLE 7-continued

Chemical Structures of Products (P)

| ID | Structure |
| --- | --- |
| P165 | 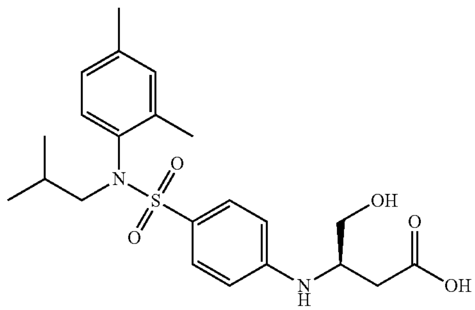 [SMILES: Cc1ccc(N(CC(C)C)S(=O)(=O)c2ccc(N[C@@H](CO)CC(=O)O)cc2)c(C)c1] |
| P166 | 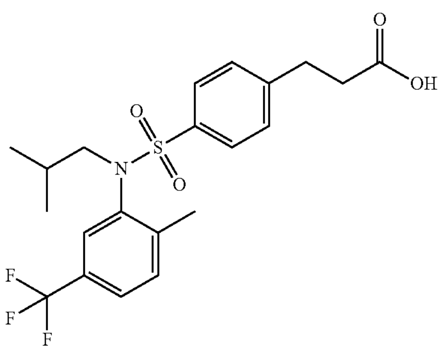 [SMILES: Cc1ccc(C(F)(F)F)cc1N(CC(C)C)S(=O)(=O)c1ccc(CCC(=O)O)cc1] |
| P167 | 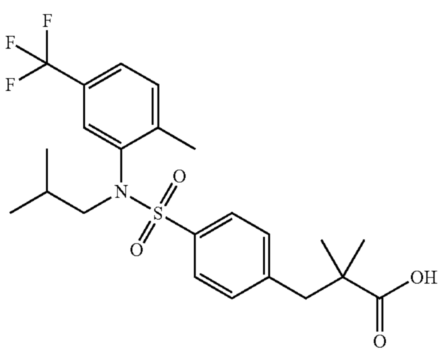 [SMILES: Cc1ccc(C(F)(F)F)cc1N(CC(C)C)S(=O)(=O)c1ccc(CC(C)(C)C(=O)O)cc1] |
| P168 | 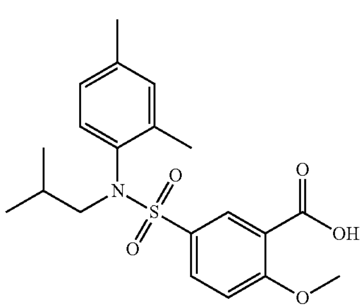 [SMILES: COc1ccc(S(=O)(=O)N(CC(C)C)c2ccc(C)cc2C)cc1C(=O)O] |
| P169 | |
| P170 | |
| P171 | |
| P172 | |

TABLE 7-continued

Chemical Structures of Products (P)

| ID | Structure |
|---|---|
| P173 | 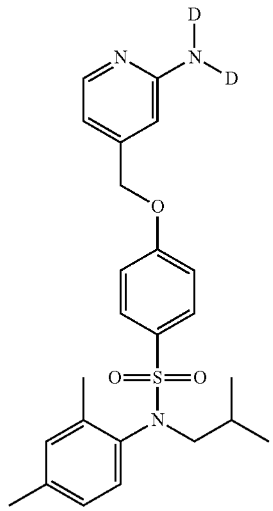 |
| P174 | 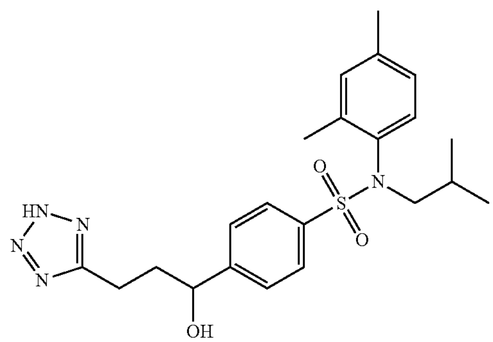 [SMILES: Cc1ccc(N(CC(C)C)S(=O)(=O)c2ccc(C(O)CCc3nn[nH]n3)cc2)c(C)c1] |
| P175 | 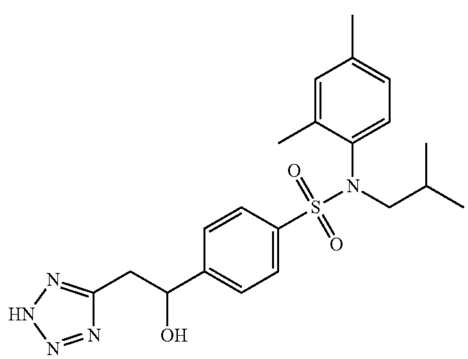 [SMILES: Cc1ccc(N(CC(C)C)S(=O)(=O)c2ccc(C(O)Cc3nn[nH]n3)cc2)c(C)c1] |
| P176 | 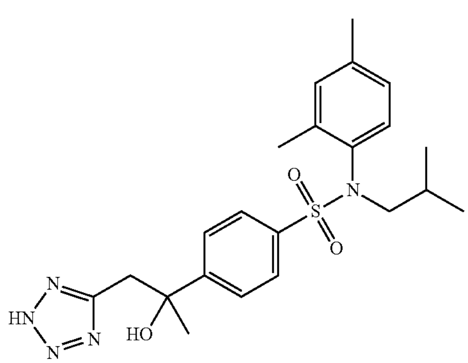 [SMILES: Cc1ccc(N(CC(C)C)S(=O)(=O)c2ccc(C(C)(O)Cc3nn[nH]n3)cc2)c(C)c1] |
| P177 | |
| P178 | |
| P179 | |
| P180 | |

TABLE 7-continued

Chemical Structures of Products (P)

| ID | Structure |
|---|---|
| P181 | (structure shown) |

Analytical Methodology

Outlined below are general methods for work-up and purification.

Work-up

Reactions were worked up in a number of ways which may be combined for example by solid-phase extraction (SPE) using either sulfonic acid (SCX) or aminopropyl ($NH_2$) cartridges eluting with methanol and then 2M methanolic ammonia (Method S); solid-phase extraction using fluorous cartridges eluting with methanol:water (Method FL); evaporation either in vacuo or by blowing nitrogen across sample (Method E); and aqueous work up where the sample is diluted with water or dilute acid or dilute base and then extracted with a suitable solvent, for example ethyl acetate or dichloromethane (Method A) or filtration of sample through a filter tube (Method F).

Evaporation

Samples were concentrated using Radley's nitrogen blow down unit, rotary evaporator or Biotage V10 evaporator to give crude residue.

Purification

Purification was by a range of methods including: mass-directed autoprep (MDAP) using either low or high pH modifiers see below for column details; automated normal phase chromatography on for example a Biotage Flashmaster II or a ISCO companion, using silica or aminopropyl column and a range of solvents, which included, for example, ethyl acetate/cyclohexane/dichloromethane and methanol; or recrystallisation from suitable solvent.

TABLE 8

Purification Methods

| Purification | Key (as used in Tables 1 to 4) |
|---|---|
| MDAP (formic modifier) | F |
| MDAP (high pH) | A |
| MDAP (high pH) | A2 |
| MDAP (TFA modifier) | T |
| Normal Phase Chromatography: Silica: EtOAc- cyclohexane 0-100% | E1 |
| Normal Phase Chromatography: Silica 0-50% ethyl acetate-cyclohexane | E2 |
| Normal Phase Chromatography: Silica EtOAc- cyclohexane 0-25% | E3 |
| Normal Phase Chromatography: Silica DCM | D1 |
| Normal Phase Chromatography: Silica 0-100% DCM in cyeohexane | D2 |
| Normal Phase Chromatography Silica 0-50% DCM in cyclohexane | D3 |
| Normal Phase Chromatography Silica 0-30% DCM inCyclohexane | D4 |
| Normal Phase Chromatography: Silica 0-25% DCM inCyclohexane | D5 |
| Normal phase chromatography: Amino Propyl Silica 0-100% EtOAc in cyclohexane | N1 |
| Normal Phase Chromatography: Amino Propyl Silica DCM- cyclohexane 0-50% | N2 |
| Normal Phase Chromatography: Amino Propyl Silica DCM- cyclohexane 0-30% | N3 |
| Normal Phase Chromatography: Silica EtOAc- DCM 0-100% | ED1 |
| Re-crystallisation from Methanol | R |

MDAP Purification

MDAP (Formic Modifier): Method F

The HPLC analysis was conducted on a Sunfire C18 column (150 mm×30 mm i.d. 5 μm packing diameter) at ambient temperature.

The solvents employed were:

A=0.1% v/v solution of Formic Acid in Water.

B=0.1% v/v solution of Formic Acid in Acetonitrile.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

MDAP (high pH): Method A

The HPLC analysis was conducted on an XBridge C18 column (150 mm×30 mm i.d. 5 μm packing diameter) at ambient temperature.

The solvents employed were:

A=10 mM Ammonium Bicarbonate in water adjusted to pH 10 with Ammonia solution.

B=Acetonitrile.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

MDAP (High pH): Method A2

The HPLC analysis was conducted on a Waters Xbridge Shield RP18 C18 column (100 mm×19 mm i.d. 5 μm packing diameter) at ambient temperature.

The solvents employed were:

A=10 mM Ammonium Bicarbonate in water adjusted to pH 10 with Ammonia solution.

B=Methanol.

The gradient was selected according to the analytical retention time.

The UV detection was an averaged signal from wavelength of 210 nm to 400 nm and mass spectra were recorded on a mass spectrometer using alternate-scan positive and negative mode electrospray ionization.

MDAP (TFA Modifier): Method T

The HPLC analysis was conducted on a Sunfire C18 column (150 mm×30 mm i.d. 5 μm packing diameter) at ambient temperature.

The solvents employed were:

A=0.1% v/v solution of Trifluoroacetic Acid in Water.

B=0.1% v/v solution of Trifluoroacetic Acid in Acetonitrile.

The gradient was selected according to the analytical retention time.

The UV detection was an averaged signal from wavelength of 210 nm to 350 nm and mass spectra were recorded on a mass spectrometer using positive electrospray ionisation.

LCMS Analysis Conditions

The following conditions are representative of those used for the generation of analytical LCMS data. Unless otherwise stated, all LCMS data were generated using the formic acid LCMS method described below.

Formic Acid Generic Analytical UPLC Open Access LC/MS (2 Minute Method)

The UPLC analysis was conducted on an Acquity UPLC BEH C18 column (2.1 mm×50 mm i.d. 1.7 µm packing diameter) at 40 degrees centigrade.

The solvents employed were:

A=0.1% v/v solution of Formic Acid in Water.

B=0.1% v/v solution of Formic Acid in Acetonitrile.

The gradient employed was:

| Time (min) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

High PH LC/MS (2 Minute Method)

UPLC analysis was conducted on an Acquity UPLC BEH C18 column (50 mm×2.1 mm i.d. 1.7 µm packing diameter) at 40° C.

The solvents employed were:

A=10 mM ammonium bicarbonate in water adjusted to pH 10 with ammonia solution.

B=Acetonitrile.

The gradient employed was:

| Time (min) | Flow Rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 99 | 1 |

The UV detection was a summed signal from wavelength of 210 nm to 350 nm and mass spectra were recorded on a mass spectrometer, such as a Waters ZQ, using alternate-scan positive and negative mode electrospray ionization.

$^1$H NMR Analysis $^1$H NMR spectra were recorded on a Bruker DRX 400 (400 MHz) instrument. The following abbreviations have been used: s, singlet; d, doublet; t, triplet; Hz, Hertz.

TABLE 9

$^1$H NMR Data for a Selection of Example RORγ Modulators

| Product No. | $^1$H NMR Data |
|---|---|
| P34 | $^1$H NMR (600 MHz, DMSO-d6) δ = 7.47 (2H, d), 7.33-7.38 (2H, m), 7.29-7.33 (1H, m), 7.15 (2H, d), 7.07 (2H, d), 5.01 (2H, s), 3.30 (2H, d), 2.41 (3H, s), 2.21 (3H, s), 1.41 (1H, m), 0.84 (6H, d) |
| P35 | $^1$H NMR (600 MHz, DMSO-d6) δ = 7.58 (2H, d), 7.38 (1H, d), 7.30 (1H, t), 7.20 (2H, d), 7.11 (1H, t), 6.61 (1H, d), 5.01-5.10 (2H, m), 3.54-3.62 (1H, m), 3.15 (1H, ddd), 2.64-2.78 (2H, m), 2.40-2.44 (3H, m, H-15), 2.23 (3H, s, H-6), 1.20-1.39 (2H, m), 1.17 (3H, t), 0.80 (3H, t) |
| P36 | $^1$H NMR (400 MHz, DMSO-d6) δ = 7.53-7.44 (m, 2 H), 7.22 (t, 1 H), 7.18-7.08 (m, 3 H), 6.90 (s, 1 H), 6.81 (d, 1 H), 5.02 (s, 2 H), 3.28 (d, 2 H), 2.42 (s, 3 H), 2.26 (s, 3 H), 2.22 (s, 3 H), 1.50-1.36 (m, 1 H), 0.84 (d, 6 H) |
| P37 | $^1$H NMR (400 MHz, DMSO-d6) δ = 7.61-7.34 (m, 2 H), 7.26-7.10 (m, 3 H), 7.04 (d, 1 H), 6.40 (s, 1 H), 5.05 (s, 2 H), 3.44-3.34 (m, 1 H), 3.05 (dd, 1 H), 2.43 (s, 3 H), 2.22 (s, 6 H), 2.12 (s, 3 H), 1.58-1.26 (m, 1 H), 0.94 (d, 3 H), 0.76 (d, 3 H) |
| P38 | $^1$H NMR (400 MHz, DMSO-d6) δ = 7.52-7.43 (m, 2 H), 7.25 (t, 1 H), 7.18-7.08 (m, 3 H), 6.88 (d, 1 H), 6.81 (br. s., 1 H), 5.01 (s, 2 H), 3.29 (d, 2 H), 2.59-2.52 (m, 2 H), 2.42 (s, 3 H), 2.21 (s, 3 H), 1.52-1.32 (m, 1 H), 1.08 (t, 3 H), 0.84 (d, 6 H) |
| P39 | $^1$H NMR (400 MHz, DMSO-d6) δ = 7.65-7.56 (m, 2 H), 7.53-7.45 (m, 1 H), 7.40-7.30 (m, 1 H), 7.25-7.16 (m, 3 H), 5.05 (s, 2 H), 3.27 (d, 2 H), 2.42 (s, 3 H), 2.22 (s, 3 H), 1.52-1.35 (m, 1 H), 0.84 (d, 6 H) |
| P40 | $^1$H NMR (400 MHz, DMSO-d6) δ = 7.71-7.55 (m, 3 H), 7.31 (ddd, 1 H), 7.25-7.18 (m, 2 H), 7.00 (dd, 1 H), 5.05 (s, 2 H), 3.38-3.32 (m, 1 H), 3.27-3.18 (m, 1 H), 2.43 (s, 3 H), 2.22 (s, 3 H), 1.49-1.39 (m, 1 H), 0.91 (d, 3 H), 0.79 (d, 3 H) |
| P41 | $^1$H NMR (400 MHz, DMSO-d6) δ = 7.52-7.45 (m, 4 H), 7.44-7.38 (m, 2 H), 7.38-7.32 (m, 1 H), 7.25 (t, 1 H), 7.20-7.13 (m, 2 H), 6.89 (dd, 1 H), 6.63 (dd, 1 H), 6.56 (t, 1 H), 5.19 (s, 2 H), 3.67 (s, 3 H), 3.29 (d, 2 H), 1.51-1.36 (m, 1 H), 0.84 (d, 6 H) |
| P42 | $^1$H NMR (400 MHz, METHANOL-d4) δ = 7.55-7.40 (m, 2 H), 7.19-7.01 (m, 4 H), 6.90 (d, 2 H), 4.95 (s, 2 H), 3.29 (s, 2 H), 2.40 (s, 3 H), 2.29 (s, 3 H), 2.25 (s, 3 H), 1.59-1.41 (m, 1 H), 0.87 (d, 6 H) |
| P43 | $^1$H NMR (400 MHz, CHLOROFORM-d)δ = 7.74-7.56 (m, 2 H), 7.11 (s, 1 H), 7.05-6.93 (m, 2 H), 6.86 (d, 1 H), 6.51 (d, 1 H), 4.86 (s, 2 H), 3.52 (dd,, 1 H), 3.14 (dd, 1 H), 2.48-2.43 (m, 3 H), 2.42-2.38 (m, 3 H), 2.31 (s, 6 H), 0.94-0.75 (m, 1 H), 0.51-0.30 (m, 2 H), 0.25-0.10 (m, 1 H), 0.01--0.10 (m, 1 H) |
| P44 | $^1$H NMR (400 MHz, DMSO-d6) δ = 7.65-7.41 (m, 2 H), 7.24-7.09 (m, 2 H), 6.64 (d, 1 H), 6.49-6.43 (m, 1 H), 6.42-6.37 (m, 1 H), 5.04 (s, 2 H), 3.38-3.33 (m, 1 H), 2.99 (dd, 1 H), 2.42 (s, 3 H), 2.22 (s, 3 H), 2.18 (s, 3 H), 1.53-1.34 (m, 1 H), 0.94 (d, 3 H), 0.76 (d, 3 H) |
| P109 | $^1$H NMR (400 MHz, METHANOL-d4) d ppm 7.60-7.74 (m, 2 H) 7.06-7.23 (m, 2 H) 6.94 (br. s., 2 H) 5.00 (s, 2 H) 2.37-2.51 (m, 5 H) 2.27 (s, 3 H) 2.01 (br. s., 6 H) 1.53-1.75 (m, 1 H) 0.93-1.00 (m, 1 H) 0.89 (d, 6 H) 0.38-0.65 (m, 2 H) 0.06-0.28 (m, 2 H) |
| P111 | $^1$H NMR (400 MHz, METHANOL-d4) d ppm 7.56-7.67 (m, 2 H), 7.08-7.21 (m, 4 H), 6.91-7.02 (m, 1 H), 5.00 (s, 2 H), 3.33 (d, 2 H), 2.43 (s, 3 H), 2.27 (s, 3 H), 1.48-1.59 (m, 1 H), 0.90 (d, 6 H) |

TABLE 9-continued

1H NMR Data for a Selection of Example RORγ Modulators

| Product No. | 1H NMR Data |
|---|---|
| P112 | 1H NMR (400 MHz, CHLOROFORM-d) d ppm 7.54 (d, 2 H), 7.31 (t, 1 H), 6.97-7.03 (m, 4 H), 4.86 (s, 2 H), 3.26 (d, 2 H), 2.44 (s, 3 H), 2.31 (s, 3 H), 1.57-1.65 (m, 1 H), 0.92 (d, 6 H) |
| P113 | 1H NMR (400 MHz, CHLOROFORM-d) d ppm 7.60-7.75 (m, 2 H), 7.31-7.41 (m, 1 H), 7.24-7.30 (m, 1 H), 7.18 (d, 1 H), 6.98-7.03 (m, 2 H), 4.86 (s, 2 H), 3.27-3.44 (m, 2 H), 2.44 (s, 3 H), 2.31 (s, 3 H), 1.57-1.68 (m, 1 H), 0.96 (d, 3 H), 0.92 (d, 3 H) |
| P114 | 1H NMR (400 MHz, CHLOROFORM-d) d ppm 7.53 (d, 2 H), 7.40 (d, 1 H), 7.16 (d, 1 H), 6.93-7.04 (m, 3 H), 4.85 (s, 2 H), 3.27 (d, 2 H), 2.44 (s, 3 H), 2.31 (s, 3 H), 1.58-1.64 (m, 1 H), 0.92 (d, 6 H) |
| P116 | 1H NMR (400 MHz, METHANOL-d4) d ppm 7.45-7.54 (m, 2 H), 7.07-7.13 (m, 2 H), 7.04 (d, 1 H), 6.82 (d, 1 H), 6.70 (dd, 1 H), 4.98 (s, 2 H), 3.27-3.29 (m, 2 H), 2.42 (s, 3 H), 2.26 (s, 3 H), 2.23 (s, 3 H), 2.18 (s, 3 H), 1.51 (m, 1 H), 0.88 (d, 6 H) |
| P117 | 1H NMR (400 MHz, METHANOL-d4) d ppm 7.47-7.55 (m, 2 H), 7.08-7.16 (m, 2 H), 6.89 (d, 1 H), 6.73 (s, 1 H), 6.62 (d, 1 H), 4.98 (s, 2 H), 3.29-3.34 (m, 2 H), 2.42 (s, 3 H), 2.28 (s, 3 H), 2.26 (s, 3 H), 1.54 (m, 1 H), 0.90 (d, 6 H) |
| P118 | 1H NMR (400 MHz, METHANOL-d4) d ppm 7.46-7.53 (m, 2 H), 7.06-7.14 (m, 2 H), 6.94 (s, 1 H), 6.63 (s, 2 H), 4.99 (s, 2 H), 3.28-3.30 (m, 2 H), 2.42 (s, 3 H), 2.27 (s, 3 H), 2.22 (br. s, 6 H), 1.52 (m, 1 H), 0.89 (d, 6 H) |
| P123 | 1H NMR (400 MHz, METHANOL-d4) d ppm 8.89 (d, 2 H) 8.22 (d, 2 H) 7.50-7.66 (m, 2 H) 7.18-7.32 (m, 2 H) 7.09 (s, 1 H) 6.80-6.96 (m, 1 H) 6.49 (d, 1 H) 5.58 (s, 2 H) 3.39-3.56 (m, 1 H) 2.96-3.16 (m, 1 H) 2.29 (d, 6 H) 1.42-1.63 (m, 1 H) 1.00 (d, 3 H) 0.80 (d, 3 H) |
| P126 | 1H NMR (400 MHz, METHANOL-d4) d ppm 7.79-7.95 (m, 2 H) 7.59-7.71 (m, 2 H) 7.41-7.54 (m, 2 H) 7.07 (s, 2 H) 6.76-6.93 (m, 2 H) 6.38-6.57 (m, 6 H) 5.29 (s, 2 H) 3.37-3.53 (m, 1 H) 3.04-3.18 (m, 1 H) 2.26 (d, 6 H) 1.42-1.60 (m, 1 H) 0.98 (d, 3 H) 0.79 (d, 3 H) |
| P127 | 1H NMR (400 MHz, METHANOL-d4) d ppm 8.54 (d, 1 H) 7.81 (dd, 1 H) 7.66 (d, 2 H) 7.52 (d, 2 H) 7.08 (br. s., 1 H) 6.77-6.91 (m, 1 H) 6.38-6.55 (m, 1 H) 6.16-6.38 (m, 1 H) 5.26 (s, 2 H) 3.37-3.53 (m, 1 H) 2.99-3.20 (m, 1 H) 2.26 (d, 6 H) 1.40-1.63 (m, 1 H) 0.93-1.04 (m, 3 H) 0.72-0.84 (m, 3 H) |
| P128 | 1H NMR (400 MHz, METHANOL-d4) d ppm 8.42-8.59 (m, 2 H) 7.50-7.64 (m, 5 H) 7.46 (d, 2 H) 7.08 (s, 1 H) 6.85 (d, 1 H) 6.48 (d, 1 H) 4.65-4.71 (m, 2 H) 4.71-4.74 (m, 2 H) 3.38-3.55 (m, 1 H) 3.05-3.14 (m, 1 H) 2.27 (br. s., 6 H) 1.46-1.58 (m, 1 H) 0.97-1.02 (m, 3 H) 0.77-0.82 (m, 3 H) |
| P135 | 1H NMR (400 MHz, METHANOL-d4) d ppm 7.54 (d, 2 H) 6.93-7.23 (m, 4 H) 6.20-6.47 (m, 1 H) 4.90-5.12 (m, 2 H) 3.41-3.59 (m, 1 H) 3.00-3.19 (m, 1 H) 2.57-2.76 (m, 1 H) 2.42 (s, 3 H) 2.33 (s, 3 H) 2.27 (s, 3 H) 1.41-1.60 (m, 1 H) 0.91-1.10 (m, 9 H) 0.80 (d, 3 H) |

Biological Evaluation

The compounds of formula (I) and pharmaceutically acceptable salts thereof are RORγ modulators, and hence have utility in the treatment of inflammatory, metabolic and autoimmune diseases mediated by RORγ. The biological activities of exemplified compounds of formula (I) were assessed in the following disclosed assays.

Dual Fluorescence Energy Transfer (FRET) Assay

This assay is based on the knowledge that nuclear receptors interact with cofactors (transcription factors) in a ligand dependent manner. RORγ is a typical nuclear receptor in that it has an AF2 domain in the ligand binding domain (LBD) which interacts with co-activators. The sites of interaction have been mapped to the LXXLL (SEQ ID NO:1) motifs in the co-activator SRC1(2) sequences. Short peptide sequences containing the LXXLL (SEQ ID NO:1) motif mimic the behavior of full-length co-activator.

This assay measures ligand-mediated interaction of the co-activator peptide with the purified bacterial-expressed RORγ ligand binding domain (RORγ-LBD) to indirectly assess ligand binding. RORγ has a basal level of interaction with the co-activator SRC1(2) in the absence of ligand, Thus, it is possible to find ligands that inhibit or enhance the RORγ/SRC1(2) interaction.

Materials

Generation of RORγ-LBD Bacterial Expression Plasmid

Human RORγ Ligand Binding Domain (RORγ-LBD) was expressed in *E. coli* strain BL21(DE3) as an amino-terminal polyhistidine tagged fusion protein. DNA encoding this recombinant protein was sub-cloned into a modified pET21a expression vector (Novagen). A modified polyhistidine tag (MKKHHHHHHLVPRGS) (SEQ ID NO:2)was fused in frame to residues 263-518 of the human RORγ sequence.

Protein Purification

Approximately 50 g *E. coli* cell pellet was resuspended in 300 mL of lysis buffer (30 mM imidazole pH 7.0 and 150 mM NaCl). Cells were lysed by sonication and cell debris was removed by centrifugation for 30 minutes at 20,000 g at 4° C. The cleared supernatant was filtered through a 0.45 uM cellulose acetate membrane filter. The clarified lysate was loaded onto a column (XK-26) packed with ProBond Nickel Chelating resin (InVitrogen), pre-equilibrated with 30 mM imidazole pH 7.0 and 150 mM NaCl. After washing to baseline absorbance with the equilibration buffer, the column was developed with a gradient from 30 to 500 mM imidazole pH 7.0. Column fractions containing the RORγ-LBD protein were pooled and concentrated to a volume of 5 mLs. The concentrated protein was loaded onto a Superdex 200 column pre-equilibrated with 20 mM Tris-Cl pH 7.2 and 200 mM NaCl. The fractions containing the desired RORγ-LBD protein were pooled together.

Protein Biotinylation

Purified RORγ-LBD was buffer exchanged by exhaustive dialysis [3 changes of at least 20 volumes (>8000x)] against PBS [100 mM NaPhosphate, pH 8 and 150 mM NaCl]. The concentration of RORγ-LBD was approximately 30 uM in PBS. Five-fold molar excess of NHS-LC-Biotin (Pierce) was added in a minimal volume of PBS. This solution was incubated with occasional gentle mixing for 60 minutes at ambient room temperature. The modified RORγ-LBD was dialyzed against 2 buffer changes—TBS pH 8.0 containing 5 mM DTT, 2 mM EDTA and 2% sucrose—each at least 20 times of the volume. The modified protein was distributed into aliquots, frozen on dry ice and stored at −80° C. The biotinylated RORγ-LBD was subjected to mass spectrometric analysis to reveal the extent of modification by the biotinylation reagent. In general, approximately 95% of the protein had at least a single site of biotinylation and the overall extent of biotinylation followed a normal distribution of multiple sites ranged from one to five.

A biotinylated peptide corresponding to amino acid 676 to 700 (CPSSHSSLTERHKILHRLLQEGSPS) (SEQ ID NO:3) of the co-activator steroid receptor coactivator SRC1(2) was generated using similar method.

Assay
Protocol Step 1: Preparation of Europium Labeled SRC1(2) Peptide

Biotinylated SRC1(2) solution was prepared by adding an appropriate amount of biotinylated SRC1(2) from the 100 uM stock solution to a buffer containing 10 mM of freshly added DTT from solid to give a final concentration of 40 nM. An appropriate amount of Europium labeled Streptavidin was then added to the biotinylated SRC1(2) solution in a tube to give a final concentration of 10 nM. The tube was inverted gently and incubated for 15 minutes at room temperature. Twenty-fold excess biotin from the 10 mM stock solution was added and the tube was inverted gently and incubated for 10 minutes at room temperature.

Protocol Step 2: Preparation of APC Labeled RORγ-LBD

Biotinylated RORγ-LBD solution was prepared by adding an appropriate amount of biotinylated RORγ-LBD from the stock solution to a buffer containing 10 mM of freshly added DTT from solid to give a final concentration of 40 nM. An appropriate amount of APC labeled Streptavidin was then added to the biotinylated RORγ-LBD solution in a tube to give a final concentration of 20 nM. The tube was inverted gently and incubated for 15 minutes at room temperature. Twenty-fold excess biotin from the 10 mM stock solution was then added and the tube was inverted gently and incubated for 10 minutes at room temperature.

Protocol Step 3: Testing

Equal volumes of the above-described Europium labeled SRC1(2) peptide and the APC labeled RORγ-LBD were gently mixed together to give 20 nM RORγ-LBD, 10 nM APC-Strepavidin, 20 nM SRC1(2) and 5 nM Europium-Streptavidin. The reaction mixtures were incubated for 5 minutes. Using a Thermo Combi Multidrop 384 stacker unit, 25 ul of the reaction mixtures per well was added to the 384-well assay plates containing 1 ul of test compound per well in 100% DMSO. The plates were incubated for 1 hour and then read on ViewLux in Lance mode for EU/APC.

Results

The exemplified compounds of formula (I) were tested in the dual FRET assay described above. All exemplified compounds of formula (I), with the exception of P77, 169-171 and 181 that were not tested, were found to have a mean pIC50 between 5.0 and 8.0. The exemplified compounds of formula (I) P24, P28, P30, P31, P33, P98, P104, P114, P123, P140, P141, P142, P150 and P160 were found to have a mean pIC50 value of ≥7.8.

Peripheral Blood Mononucleocyte Cell Assay (PBMC Assay-IL-17)

RORs (Retinoic Acid Related Orphan Receptors) are members of the class 1 nuclear receptor family. RORs regulate gene transcription by binding to specific DNA response element (RORE) as a monomer and have critical roles of in development, immunity, circadian rhythm, and cellular metabolism (recently reviewed by A Jetten, Nuclear Receptor Signaling, 2009, 7, 1-32) One member of this nuclear receptor family, RORγt, has been identified as a regulator of differentiation and development of IL-17-expressing human and mouse CD4+ T cells, so called Th17 cells which play a role in both host defence and inflammatory disorders. RORγt is also required for transcription of the genes encoding IL-17A and IL-17F in iNKT, NKT (Immunol 2009, 2(5), 383-392, J. Immunol, 2008, 180, 51(67), 5171-5171), γδTcells (J. Resp and Crit. Care Med 2010, 182(4), 464-476), CD8+ Tcell (J Leukocyte Biol, 2007, 82(2), 354-360) and finally CD4-CD8- TCRαβ+ T cells (J. Immunol. 2008, 181 8761-8766). Additional immune cells such as eosinophils, neutrophils and macrophages can also be source of IL17A in some allergic inflammation related to asthma (J Allergy Clin Immunol 2001, 108, 430-438; J. Immunol, 2008, 181, 6117-6124; Immunity, 2004, 21, 467-476), however, the link with RORγt has not yet been confirmed in the literature.

This assay is designed to measure levels of IL-17A secreted from antiCD3/CD28 stimulated frozen Peripheral Blood Mononuclear cells (PBMC) isolated from human blood with the aim of identifying inhibitors of IL-17A release.

Assay Solutions
Assay Media Components:
RPMI 1640 (as supplied, for example, by Gibco)—90%
FCS (as supplied, for example, by Invitrogen) (endotoxin tested)—10%
Penicillyn/Streptomycin solution ×1
Preparation: 50 mL Heat Inactivated Australian FBS, 5 mL Glutamax and 5 mL
Penicillin/Streptomycin are aseptically added to 500 mL RPMI in a biosafety cabinet. The Penicllin/Streptomycin 100× stock is supplied by, for example, Gibco (10,000 Units/mL Penicillin, 10,000 ug/mL Streptomycin). Stock L-glutamine 100× (as supplied, for example, by Invitrogen)
Note: To be kept in a fridge (4° C.) for 4 weeks. Warm up in a water bath set at 37° C. prior to use.

Anti-Human IL-17 Detection Antibody Components:
IL-17 detection antibody and Blocking buffer B (supplied, for example, by Mesoscale Discovery) Dulbecco's PBS without $Ca^{2+}$ and $Mg^{2+}$ (supplied, for example, by Gibco)
Note: Prepare detection anti body at final concentration of 1 ug/mL. Solution to be kept refrigerated.

MSD Read Buffer T×2 Components:
Water and MSD Read Buffer T×4 (as supplied, for example, by MSD)
Note: Dilute MSD Read Buffer T×4 in half with water. To be kept at room temperature.

Assay Capacity: 384
Equipment and Materials
MSD Sector Imager 6000 supplied by MesoScale Discovery (MSD)
Multidrop 384 supplied by Thermo Scientific
CyBi-Well, model 7518-00 supplied by CyBio AG
Microplates 384 clear supplied by Greiner
Assay
Protocol Step 1: Assay Plates Preparation Before Adding Cell Suspension
1. Ensure no external endotoxin is present in media and reagents used in the assay.
2. The compounds for screening are dispensed into a master plate at 10 mM top concentration which are serially diluted 1:3 across 11 points in DMSO, then 500 nl is transferred into a 384-well flat-bottomed Greiner plate to which 50 ul of cell suspension is added: for the single shot screening the highest concentration of compound is $10^{-5}$M; for 11 point full curve dose response studies the highest concentration is $10^4$ M.

Controls:
As a low control, DMSO (as supplied, for example, by VWR) (final concentration 1%) in column 6 (16 points).
As a high control, 5-(4-fluorophenyl)-2-ureidothiophene-3-carboxamide (obtainable from, for example, Sigma) at a final concentration of $10^{-4}$ M in DMSO should be used in column 18 (16 points).
If the compounds dispensed earlier than the day of the assay, they should be kept at −20° C.

Protocol Step 2: Day 1: Thawing and Handing of PBMC
1. Thaw PBMC in the vial using water bath (37° C.). Ensure that water does not cover the vial (the level should be lower than the screw cup of the vial)

2. Transfer the contents of the vial into 50 mL Falcon tube.
3. Add 10 mL of Assay Media drop by drop to decrease the concentration of DMSO (as supplied, for example, by VWR) in the freezing media gradually.
4. Spin down the cells in a centrifuge (1000 rpm-5 mins).
5. Decant the supernatant.
6. Re-suspend the cells in 10 mL of Assay Media.
7. Transfer of 0.1 mL of suspension into Cedex counting tube.
8. Add 0.9 mL of media to achieve volume of the suspension for counting up to 1 mL. Count the cells on Cedex using 1:10 dilution factor settings.
9. Make the cell suspension at the concentration $8 \times 10^5$ cells/mL. to give a final number of 40,000 cells/well.

Protocol Step 3: Day 1: Stimulation of PBMC with CD3/CD28 beads
1. Add well mixed CD3/CD28 Dynabeads (as supplied, for example, by Dynal) to achieve ratio bead:cell=2:1 (i.e a dilution of 1 in 20). Mix thoroughly.
2. Dispense the suspension into the 384 Assay Plates using Multidrop (50 ul per well).
If the volume of cell suspension is large, mix the suspension after dispensing into every other plate.
3. Cover the plates with the lids and place them to the humidified incubator (37° C., 5% $CO_2$) for 48 hours.

Protocol Step 4: Day 2: MSD plates preparation
1. Block cytokine capture Mesoscale Discovery MSD plates with 0.1% Block buffer B (provided by Mesoscale Dsicovery) in D-PBS solution using 40 ul per well.
2. Leave the plates covered with lids in the fridge over night.
3. Plates are washed manually using PBS and a multidrop combi. Blocker B buffer is flicked out into a waste pot and 40 ul of PBS is dispensed into the plate using a combi. This is then flicked out manually and the plates tapped on to blue roll to remove as much residual liquid as possible before transferring the cell supernatant.
4 Tap the plates over a paper towel.

Protocol Step 5: Day 3: IL-17 Detection on MSD plates
1. Transfer 10 ul of supernatants from assay plates to the MSD plates using Cybiwell. Ensure that all wells are covered with the solution. Tap the plate gently, if some of the wells are not covered with the supernatant.
2. Cover the plates with adhesive foil (brown stickers) and leave them for 1 hour of incubation on shaker at room temperature (RT).
3. Add 10 ul of MSD IL-17 detecting antibody using multidrop (1 ug/mL in D-PBS without $Ca^{2+}$ and $Mg^{2+}$ (supplied, for example, by Gibco)).
4. Cover the plates with adhesive foil and incubated with shaking for 3 hours at room temperature
5. Plates are washed manually twice using PBS and a multidrop combi as before.
6. Tap the plates over a paper towel.
7. Add 35 ul of MSD Read Buffer T×2 using multidrop.
8. Read plates on MSD MA6000 reader using the 384 well plate protocol as per manufacturer's instructions.

Results

The exemplified compounds of formula (I) were tested in the PBMC assay described above. All exemplified compounds of formula (I), with the exception of P99, P105, P107, P153, P154, P159, P161-165, P168-171, P174-176, P178, P180 and P181 that were not tested and P179 which had a value of <4.0, were found to have a mean pIC50 between 4.0 and 7.0. The exemplified compounds of formula (I) P23, P24, P28, P30, P31, P33, P37, P118, P123, P128, P132, P137, P140, P143, P144, P147, P155 and P160 were found to have a mean pIC50 value of ≥6.0.

Utility

Compounds of formula (I), and pharmaceutically acceptable salts thereof, are modulators of RORγ and can be useful in the treatment of inflammatory, metabolic and autoimmune diseases mediated by RORγ such as asthma, chronic obstructive pulmonary disease (COPD) and bronchitis, allergic diseases, such as allergic rhinitis and atopic dermatitis, cystic fibrosis, lung allograph rejection, multiple sclerosis, rheumatoid arthritis, juvenile Rheumatoid arthritis, Osteoarthritis, ankylosing spondylitis, systemic lupus erythematosus, psoriasis, Hashimoto's disease, pancreatisis, autoimmune diabetes, autoimmune ocular disease, ulcerative colitis, Crohn's disease, inflammatory bowel disease (IBS), inflammatory bowel syndrome (IBD), Sjorgen's syndrome, optic neuritis, type I diabetes, neuromyelitis optica, Myastehnia Gravis, uveitis, Guillain-Barre syndrome, psoriatic arthritis, Graves' disease and scleritis. The use of RORγ modulators for the treatment of the respiratory diseases listed above, such as asthma and COPD is of particular interest.

In a further aspect, the present invention also provides a compound of formula (I), or a pharmaceutically acceptable salt or solvate thereof, for use in therapy.

In a further aspect, the present invention also provides a compound of formula (I), or a pharmaceutically acceptable salt or solvate thereof, for use in the treatment of inflammatory, metabolic and autoimmune diseases mediated by RORγ.

In a further aspect, the present invention provides a compound of formula (I), or a pharmaceutically acceptable salt thereof, for use in the treatment of asthma or chronic obstructive pulmonary disease.

In a further aspect, the present invention is directed to a method of treatment of an inflammatory, metabolic or autoimmune disease mediated by RORγ, which comprises administering to a subject in need thereof, a safe and therapeutically effective amount of a compound of formula (I), or a pharmaceutically acceptable salt thereof.

In yet a further aspect, the present invention is directed to a method of treating chronic obstructive pulmonary disease or asthma, which comprises administering to a subject in need thereof, a safe and therapeutically effective amount of a compound of formula (I), or a pharmaceutically acceptable salt thereof.

As used herein, the term "treatment" refers to prophylaxis of the condition, ameliorating or stabilising the specified condition, reducing or eliminating the symptoms of the condition, slowing or eliminating the progression of the condition, and preventing or delaying reoccurrence of the condition in a previously afflicted patient or subject.

As used herein, the term "therapeutically effective amount" refers to the quantity of a compound of formula (I), or a pharmaceutically acceptable salt thereof, which will elicit the desired biological response in an animal or human body.

As used herein, the term "subject" refers to an animal or human body

Pharmaceutical Development

A compound of formula (I), or a pharmaceutically acceptable salt thereof, will normally, but not necessarily, be formulated into pharmaceutical compositions prior to administration to a patient. Accordingly, in another aspect the invention is directed to pharmaceutical compositions comprising a compound of formula (I), or a pharmaceutically acceptable salt thereof, and one or more pharmaceutically-acceptable excipients.

Pharmaceutical compositions comprising a compound of formula (I), or a pharmaceutically acceptable salt thereof, may be prepared using techniques and methods known to those skilled in the art. Some of the methods commonly used in the art are described in Remington's Pharmaceutical Sciences (Mack Publishing Company).

A pharmaceutical composition of a compound of formula (I), or a pharmaceutically acceptable salt thereof, may be formulated for administration by any appropriate route, for example by the inhaled, nasal, oral (including buccal or sublingual), topical (including buccal, sublingual, transdermal, epicutaneous) or parenteral (subcutaneous, intramuscular, intravenous, intradermal) route. Thus, a pharmaceutical composition of a compound of formula (I), or a pharmaceutically acceptable salt thereof, may be formulated as, for example, a solution or suspension (aqueous or non-aqueous), tablet, capsule, powder, granule, lozenge, lotion, cream, ointment, gel, foam or reconstitutable powder depending on the particular route of administration. Such pharmaceutical compositions may be prepared by any method known in the art of pharmacy, for example by bringing into association the active ingredient with the excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Pharmaceutical compositions of a compound of formula (I) or a pharmaceutically acceptable salt thereof, for topical administration, may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The compositions may also contain compatible conventional carriers, such as cream or ointment bases and ethanol or oleyl alcohol for lotions. Such carriers may be present as from about 1% up to about 98% of the composition. More usually they will form up to about 80% of the composition.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions for topical administration to the lung may include aerosol compositions and dry powder compositions.

Dry powder compositions for topical delivery to the lungs or nose generally contain a powder mix of a compound of formula (I) or a pharmaceutically acceptable salt thereof and a suitable carrier, such as lactose or starch. Dry powder compositions for topical delivery to the lung or nose may, for example, be presented in capsules and cartridges for use in an inhaler or insufflator of, for example, gelatine. Each capsule or cartridge may generally contain between 20 µg-10 mg of the compound of formula (I), or a pharmaceutically acceptable salt thereof. Alternatively, the compounds of formula (I), or pharmaceutically acceptable salts thereof, may be presented without excipients. Packaging of the pharmaceutical composition may be suitable for unit dose or multi-dose delivery. In the case of multi-dose delivery, the composition can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable composition comprising a compound of formula (I), or a pharmaceutically acceptable salt thereof, preferably combined with a carrier, such as lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of compound of formula (I), or a pharmaceutically acceptable salt thereof, may be size reduced by conventional means eg by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I), or a pharmaceutically acceptable salt thereof, as medicament in a liquid solvent with a flowing liquid antisolvent for said medicament (eg as described in International Patent Application PCT/GB99/04368). Alternatively, the particles may be prepared by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04237). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Aerosol compositions may be developed, with the use of a suitable liquefied propellant, for delivery from pressurised packs, such as a metered dose inhaler. Aerosol compositions can be either a suspension or a solution and generally contain the compound of formula (I), or a pharmaceutically acceptable salt thereof, and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants eg oleic acid or lecithin and cosolvents eg ethanol. Aerosol compositions will generally be retained in a pressurised canister (eg an aluminium canister) closed with a valve (eg a metering valve) and fitted into an actuator with a mouthpiece. Aerosol compositions may also include aqueous solutions or suspensions that are delivered to the nose or lungs by nebulisation.

Pharmaceutical compositions for topical administration to the nose may also be developed for delivery by nasal spray or as nasal droplets. Pharmaceutical compositions for nasal administration may be developed in such a way to allow the medicament(s) to be delivered to all appropriate areas of the nasal cavities (the target tissue). Moreover, a pharmaceutical composition may be developed for nasal administration, which permits the medicament(s) to remain in contact with the target tissue for an increased period of time.

A suitable dosing regimen for a pharmaceutical composition administered topically to the nose by use of a nasal spray may be for the patient to inhale slowly through the nose subsequent to the nasal cavity being cleared. During inhalation, the composition may be administered to one nostril while the other is manually compressed. This procedure may then be repeated for the other nostril. Generally, one or two sprays per nostril may be administered by the above procedure up to two or three times each day. Typically, each spray to the nostril may deliver from about 25 to about 100 μL of the pharmaceutical composition.

Pharmaceutical compositions for topical administration to the nose by nasal spray or as nasal drops may be prepared as a solution or suspension. The solution or suspension may be aqueous or non-aqueous based, and may contain one or more pharmaceutically acceptable excipients, such as suspending agents, for example carboxymethylcellulose, methylcellulose, veegum, tragacanth, bentonite and polyethylene glycols; preservatives, for example chelating agents (e.g EDTA), quaternary ammonium compounds (e.e benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid) and other anti-microbial agents such as chlorhexidine, chlorocresol, sorbic acid and its salts (e.g. potassium sorbate), and polymyxin; isotonicity adjusting agents, for example sodium chloride, dextrose, xylitol and calcium chloride; buffering agents, wetting agents, for example fatty alcohols, esters and ethers, such as polyoxyethylene (20) sorbitan monooleate (polysorbate 80); anti-oxidants, sweetening agents and taste-masking agents.

It should be understood that in addition to the ingredients particularly mentioned above, the pharmaceutical compositions may include other agents conventional in the art having regard to the type of formulation in question.

A compound of formula (I), or a pharmaceutically acceptable salt thereof, may also be used in combination with one or more other therapeutic agents, selected from the group consisting of $\beta_2$-adrenoreceptor agonists, anti-inflammatory agents (e.g. corticosteroids and NSAID's) and anticholinergic agents.

$\beta_2$-adrenoreceptor agonists that may be used in combination with a compound of formula (I), or a pharmaceutically acceptable salt thereof, include, for example, salmeterol, salbutamol, formoterol, and salts thereof, for example the xinafoate salt of salmeterol, the sulfate salt of salbutamol or the fumarate salt of formoterol). Further $\beta_2$-adrenoreceptor agonists include those described in WO03/024439, such as 4-{(1R)-2-[(6-{2-[(2,6-dichlorobenzyl)oxy]ethoxy}hexyl) amino]-1-hydroxyethyl}-2-(hydroxymethyl)phenol and its pharmaceutically acceptable salts, such as triphenylacetate.

Corticosteroids that may be used in combination with a compound of formula (I), or a pharmaceutically acceptable salt thereof, include, for example, fluticasone propionate and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

Anticholinergic agents may also be used in combination with a compound of formula (I), or a pharmaceutically acceptable salt thereof. Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Antimuscarinic compounds for administration via inhalation include, for example, ipratropium (for example, as the bromide, CAS 22254-24-6, sold under the name Atrovent), tiotropium (for example, as the bromide, CAS 136310-93-5, sold under the name Spiriva), (3-endo)-3-(2-cyano-2,2-diphenylethyl)-8,8-dimethyl-8-azoniabicyclo[3.2.1]octane bromide, and 4-[hydroxy(diphenyl)methyl]-1-{2-[(phenylmethyl)oxy]ethyl}-1-azoniabicyclo[2.2.2]octane bromide.

It will be clear to a person skilled in the art that, where appropriate, the other therapeutic agent(s) may be used in the form of pharmaceutically acceptable salts, or prodrugs, or as esters (e.g lower alkyl esters), or as solvates (e.g. hydrates) to optimise the activity and/or stability and/or physical characteristics (e.g. solubility) of the therapeutic agent. It will be clear also that, where appropriate, the therapeutic agent(s) may be used in optically pure form.

The invention thus provides in a further aspect a combination comprising a compound of formula (I), or a pharmaceutically acceptable salt thereof, and one or more other therapeutic agents.

The invention claimed is:

1. A compound of formula (I), or a pharmaceutically acceptable salt thereof:

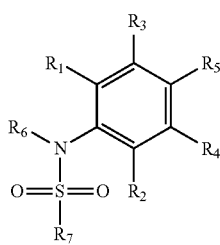

(I)

wherein
$R_1$ is $CH_3$ or halo;
$R_2$, $R_3$ and $R_4$ are H;
$R_5$ is $CH_3$ or halo;
$R_6$ is selected from the group consisting of $C_{3-5}$alkyl and $-CH_2-C_{3-4}$cycloalkyl;

$R_7$ is selected from the group consisting of

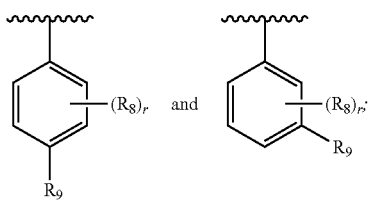

$R_8$ is selected from the group consisting of $C_{1-3}$alkyl, $C_{1-3}$alkoxy, $CH_2CN$, $CH_2OH$, OH, CN and halo;
$R_9$ is the group $-(CHR_{10})_s-(X)_t-(CHR_{10})_u-R_{11}$;
each $R_{10}$ is independently selected from the group consisting of H, OH or $CH_2OH$;
$R_{11}$ is an isoxazole;
X is $CH_2$, NH, O;
r is 0, 1 or 2;
s is 0, 1 or 2;
t is 0 or 1;
u is 0, 1 or 2;
with the proviso that no more than two $R_{10}$ groups represent OH or $CH_2OH$.

2. A compound according to claim 1, or a pharmaceutically acceptable salt thereof, wherein $R_1$ and $R_5$ are $CH_3$.

3. A compound according to claim 1, or a pharmaceutically acceptable salt thereof, wherein $R_6$ is isobutyl.

4. A compound according to claim 2, or a pharmaceutically acceptable salt thereof, wherein $R_6$ is isobutyl.

5. A compound according to claim 1, or a pharmaceutically acceptable salt thereof, wherein $R_7$ is:

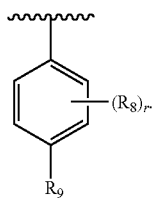

6. A compound according to claim 1, or a pharmaceutically acceptable salt thereof, wherein r is 1 and $R_8$ is $CH_2OH$.

7. A compound according to claim 1, or a pharmaceutically acceptable salt thereof, wherein $R_1$ and $R_5$ are $CH_3$, $R_6$ is isobutyl, r is 1 and $R_8$ is $CH_2OH$.

8. A compound according to claim 1, or a pharmaceutically acceptable salt thereof, wherein s is 0.

9. A compound according to claim 1, or a pharmaceutically acceptable salt thereof, wherein t is 1 and X is O.

10. A compound according to claim 1, or a pharmaceutically acceptable salt thereof, wherein each $R_{10}$ is H.

11. A compound according to claim 1, or a pharmaceutically acceptable salt thereof, wherein $R_{11}$ is 3,5-dimethylisoxazole, of formula:

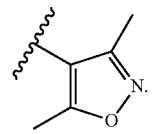

12. A compound according to claim 1, or a pharmaceutically acceptable salt thereof, wherein $R_1$ and $R_5$ are $CH_3$, $R_6$ is isobutyl, r is 1, $R_8$ is $CH_2OH$, wherein t is 1, and X is O.

13. A compound according to claim 1, or a pharmaceutically acceptable salt thereof, wherein $R_1$ and $R_5$ are $CH_3$, $R_6$ is isobutyl, r is 1, $R_8$ is $CH_2OH$, wherein t is 1, and X is O, each $R_{10}$ is H, and $R_{11}$ is 3,5-dimethylisoxazole, of formula:

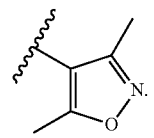

14. A compound according to claim 1, or a pharmaceutically acceptable salt thereof, which is selected from the group consisting of:

N-(4-butyl-2-methylphenyl)-4-{[(3,5-dimethyl-4-isoxazolyl)methyl]oxy}-N-(2-methylpropyl)benzenesulfonamide;

4-((3,5-dimethylisoxazol-4-yl)methoxy)-N-(2,4-dimethylphenyl)-N-isobutylbenzenesulfonamide;

4-{[(3,5-dimethyl-4-isoxazolyl)methyl]oxy}-N-(4-fluoro-2-methylphenyl)-N-(2-methylpropyl)benzenesulfonamide;

N-(2,4-difluorophenyl)-4-{[(3,5-dimethyl-4-isoxazolyl)methyl]oxy}-N-(2-methylpropyl)benzenesulfonamide;

N-(4-butylphenyl)-4-{[(3,5-dimethyl-4-isoxazolyl)methyl]oxy}-N-(2-methylpropyl)benzenesulfonamide;

4-{[(3,5-dimethyl-4-isoxazolyl)methyl]oxy}-N-[4-(1-methylethyl)phenyl]-N-(2-methylpropyl)benzenesulfonamide;

4-{[(3,5-dimethyl-4-isoxazolyl)methyl]oxy}-N-(2-fluoro-4-methylphenyl)-N-(2-methylpropyl)benzenesulfonamide;

N-(4-chlorophenyl)-4-((3,5-dimethylisoxazol-4-yl)methoxy)-N-isobutylbenzenesulfonamide;

4-((3,5-dimethylisoxazol-4-yl)methoxy)-N-isobutyl-N-(4-propylphenyl)benzenesulfonamide;

4-((3,5-dimethylisoxazol-4-yl)methoxy)-N-isobutyl-N-(3-(trifluoromethyl)phenyl)benzenesulfonamide;

4-((3,5-dimethylisoxazol-4-yl)methoxy)-N-isobutyl-N-(2-methyl-5-(trifluoromethyl)phenyl)benzenesulfonamide;

4-((3,5-dimethylisoxazol-4-yl)methoxy)-N-isobutyl-N-phenylbenzenesulfonamide;

4-((3,5-dimethylisoxazol-4-yl)methoxy)-N-(2-ethylphenyl)-N-propylbenzenesulfonamide;

4-{[(3,5-dimethyl-4-isoxazolyl)methyl]oxy}-N-(3-methylphenyl)-N-(2-methylpropyl)benzenesulfonamide;

4-{[(3,5-dimethyl-4-isoxazolyl)methyl]oxy}-N-(2,5-dimethylphenyl)-N-(2-methylpropyl)benzenesulfonamide;

4-{[(3,5-dimethyl-4-isoxazolyl)methyl]oxy}-N-(3-ethylphenyl)-N-(2-methylpropyl)benzenesulfonamide;

N-(5-chloro-2-fluorophenyl)-4-{[(3,5-dimethyl-4-isoxazolyl)methyl]oxy}-N-(2-methylpropyl)benzenesulfonamide;

N-(2-chloro-5-fluorophenyl)-4-{[(3,5-dimethyl-4-isoxazolyl)methyl]oxy}-N-(2-methylpropyl)benzenesulfonamide;

4-{[(3,5-dimethyl-4-isoxazolyl)methyl]oxy}-N-(4-methylphenyl)-N-(2-methylpropyl)benzenesulfonamide;

N-(cyclopropylmethyl)-4-{[(3,5-dimethyl-4-isoxazolyl)methyl]oxy}-N-(2,4-dimethylphenyl)benzenesulfonamide;

4-((3,5-dimethylisoxazol-4-yl)methoxy)-N-(4-hydroxy-2-methylphenyl)-N-isobutylbenzenesulfonamide;

4-((3,5-dimethylisoxazol-4-yl)methoxy)-N-phenyl-N-propylbenzenesulfonamide;

4-{[(3,5-dimethyl-4-isoxazolyl)methyl]oxy}-N-[3-(methyloxy)phenyl]-N-(2-methylpropyl)benzenesulfonamide;

N-[4-(cyclopropylmethyl)-2,6-dimethylphenyl]-4-{[(3,5-dimethyl-4-isoxazolyl)methyl]oxy}-N-(2-methylpropyl)benzenesulfonamide;

N-(2,5-difluorophenyl)-4-{[(3,5-dimethyl-4-isoxazolyl)methyl]oxy}-N-(2-methylpropyl)benzenesulfonamide;

N-(3,5-dichlorophenyl)-4-{[(3,5-dimethyl-4-isoxazolyl)methyl]oxy}benzenesulfonamide;

N-(2,5-dichlorophenyl)-4-{[(3,5-dimethyl-4-isoxazolyl)methyl]oxy}-N-(2-methylpropyl)benzenesulfonamide;

N-(3,4-dichlorophenyl)-4-{[(3,5-dimethyl-4-isoxazolyl)methyl]oxy}-N-(2-methylpropyl)benzenesulfonamide;

N-(3,5-difluorophenyl)-4-{[(3,5-dimethyl-4-isoxazolyl)methyl]oxy}-N-(2-methylpropyl)benzenesulfonamide;

4-{[(3,5-dimethyl-4-isoxazolyl)methyl]oxy}-N-(3,4-dimethylphenyl)-N-(2-methylpropyl)benzenesulfonamide;

4-{[(3,5-dimethyl-4-isoxazolyl)methyl]oxy}-N-(3-fluoro-5-methylphenyl)-N-(2-methylpropyl)benzenesulfonamide;

4-{[(3,5-dimethyl-4-isoxazolyl)methyl]oxy}-N-(3,5-dimethylphenyl)-N-(2-methylpropyl)benzenesulfonamide;

4-{[(3,5-dimethyl-4-isoxazolyl)methyl]oxy}-N-[2-methyl-5-(methyloxy)phenyl]-N-(2-methylpropyl)benzenesulfonamide;

4-{[(3,5-dimethyl-4-isoxazolyl)methyl]oxy}-N-(5-fluoro-2-methylphenyl)-N-(2-methylpropyl)benzenesulfonamide;

N-(3-chlorophenyl)-4-{[(3,5-dimethyl-4-isoxazolyl)methyl]oxy}-N-(2-methylpropyl)benzenesulfonamide;

4-((3,5-dimethylisoxazol-4-yl)methoxy)-N-isobutyl-N-(5-isopropyl-2-methylphenyl)benzenesulfonamide;

3-((3,5-dimethylisoxazol-4-yl)methoxy)-N-(2,4-dimethylphenyl)-N-isobutylbenzenesulfonamide;

4-((3,5-dimethylisoxazol-4-yl)methoxy)-N-isobutyl-N-(o-tolyl)benzenesulfonamide;

4-(2-(3,5-dimethylisoxazol-4-yl)ethoxy)-N-(2,4-dimethylphenyl)-N-isobutylbenzenesulfonamide;

N-(4-bromo-2-methylphenyl)-4-((3,5-dimethylisoxazol-4-yl)methoxy)-N-isobutylbenzenesulfonamide;

4-((3,5-dimethylisoxazol-4-yl)methoxy)-N-(4-(2-hydroxypropan-2-yl)-2-methylphenyl)-N-isobutylbenzenesulfonamide;

4-((3,5-dimethylisoxazol-4-yl)methoxy)-N-(4-(2-hydroxyethoxy)-2-methylphenyl)-N-isobutylbenzenesulfonamide;

4-((3,5-dimethylisoxazol-4-yl)methoxy)-N-(4-(hydroxymethyl)-2-methylphenyl)-N-isobutylbenzenesulfonamide;

4-((3,5-dimethylisoxazol-4-yl)methoxy)-N-(4-(3-hydroxypropyl)phenyl)-N-isobutylbenzenesulfonamide;

4-((3,5-dimethylisoxazol-4-yl)methoxy)-N-(4-ethylphenyl)-N-isobutylbenzenesulfonamide;

N-(2,6-difluorophenyl)-4-{[(3,5-dimethyl-4-isoxazolyl)methyl]oxy}-N-(2-methylpropyl)benzenesulfonamide;

N-(4-(1,3-dihydroxypropan-2-yl)phenyl)-4-(((3,5-dimethylisoxazol-4-yl)oxy)methyl)-N-isobutylbenzenesulfonamide.

15. A pharmaceutical composition comprising a) a compound according to claim 1, or a pharmaceutically acceptable salt thereof, and b) one or more pharmaceutically acceptable excipients.

16. A compound according to claim 1, or a pharmaceutically acceptable salt thereof, which is 4-{[(3,5-dimethyl-4-isoxazolyl)methyl]oxy}-N-(4-fluoro-2-methylphenyl)-N-(2-methylpropyl)benzenesulfonamide.

17. A pharmaceutical composition comprising a) a compound according to claim 14, or a pharmaceutically acceptable salt thereof, and b) one or more pharmaceutically acceptable excipients.

18. A pharmaceutical composition comprising a) a compound according to claim 16, or a pharmaceutically acceptable salt thereof, and b) one or more pharmaceutically acceptable excipients.

* * * * *

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence

```
<220> FEATURE:
<223> OTHER INFORMATION: Amino acid sequence identified using molecular
      biology techniques.
<220> FEATURE:
<221> NAME/KEY: VARIANT
<222> LOCATION: 2, 3
<223> OTHER INFORMATION: Xaa = Any Amino Acid

<400> SEQUENCE: 1

Leu Xaa Xaa Leu Leu
1               5

<210> SEQ ID NO 2
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Met Lys Lys His His His His His His Leu Val Pro Arg Gly Ser
1               5                   10                  15

<210> SEQ ID NO 3
<211> LENGTH: 25
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Cys Pro Ser Ser His Ser Ser Leu Thr Glu Arg His Lys Ile Leu His
1               5                   10                  15

Arg Leu Leu Gln Glu Gly Ser Pro Ser
            20                  25
```